(12) United States Patent
Zhu

(10) Patent No.: US 11,918,593 B2
(45) Date of Patent: Mar. 5, 2024

(54) PHOSPHATE DERIVATIVES AND USE THEREOF

(71) Applicant: Shanghai Shengyue Pharmaceutical Technology Co., Ltd., Shanghai (CN)

(72) Inventor: Qing Zhu, Hubei (CN)

(73) Assignee: Shanghai Shengyue Pharmaceutical Technology Co., Ltd., Shanghai (CN)

( * ) Notice: Subject to any disclaimer, the term of this patent is extended or adjusted under 35 U.S.C. 154(b) by 141 days.

(21) Appl. No.: 17/044,173

(22) PCT Filed: Mar. 25, 2019

(86) PCT No.: PCT/CN2019/079492
§ 371 (c)(1),
(2) Date: Sep. 30, 2020

(87) PCT Pub. No.: WO2019/184866
PCT Pub. Date: Oct. 3, 2019

(65) Prior Publication Data
US 2021/0030773 A1    Feb. 4, 2021

(30) Foreign Application Priority Data
Mar. 30, 2018  (CN) .......................... 201810275072.5

(51) Int. Cl.
| A61K 31/675 | (2006.01) |
| A61K 31/663 | (2006.01) |
| C07F 9/38 | (2006.01) |
| C07F 9/6558 | (2006.01) |

(52) U.S. Cl.
CPC .......... *A61K 31/675* (2013.01); *A61K 31/663* (2013.01); *C07F 9/3873* (2013.01); *C07F 9/65583* (2013.01)

(58) Field of Classification Search
CPC ... A61K 31/675; A61K 31/663; C07F 9/3873; C07F 9/65583
USPC ........................................................ 514/89
See application file for complete search history.

(56) References Cited

U.S. PATENT DOCUMENTS

| 2,917,528 A | 12/1959 | Ramsey et al. |
| 2,964,549 A | 12/1960 | Ramsey et al. |
| 2008/0161592 A1* | 7/2008 | Blaskovich ............. A61P 25/00 562/15 |

FOREIGN PATENT DOCUMENTS

| CN | 102093416 A | 6/2011 |
| CN | 102093416 A | 6/2011 |
| CN | 104755425 A | 7/2015 |
| CN | 104755425 A | 7/2015 |

OTHER PUBLICATIONS

Rawls et al., Fragment-base discovery of selective inhibitors of the Mycobacterium tuberculosis protein tyrosine phosphatase PtpA, 2009, Bioorganic & Medicinal Chemistry Letters, 19, 2009, 6851-6854 (Year: 2009).*
Holmes et al., Discovery and structure-activity relationships of novel sulfonamides as potent PTP1B inhibitors, 2005, Bioorganic & Medicinal Chemistry Letters, 15, 4336-4341 (Year: 2005).*
Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
International Search Report dated Jul. 1, 2019 in PCT/CN2019/079492.
Written Opinion dated Jul. 1, 2019 in PCT/CN2019/079492.

* cited by examiner

*Primary Examiner* — Kristin A Vajda
(74) *Attorney, Agent, or Firm* — Ice Miller LLP

(57) ABSTRACT

The present invention discloses a compound with the following formula (I), or a tautomer, mesomer, racemate, enantiomer, and diastereoisomer thereof, or a mixture form thereof, or a pharmaceutically acceptable salt thereof, or a prodrug molecule thereof, wherein D is selected from:

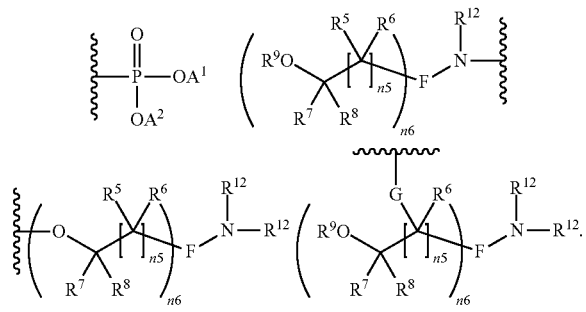

invention further discloses the use of the compound in the preparation of drugs for preventing and/or treating cancers, and the use of the compound in the preparation of drugs for inhibiting cancer metastasis. The compound of the present invention can effectively inhibit the proliferation and metastasis of cancer cells by adjusting the acidity of a tumor microenvironment to achieve a better effect in clinical cancer treatment, and has broad application prospects.

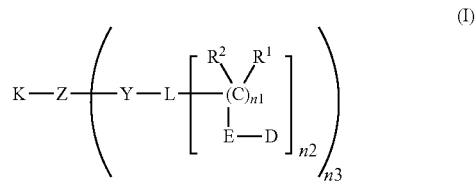

(I)

13 Claims, 1 Drawing Sheet

PHOSPHATE DERIVATIVES AND USE THEREOF

CROSS-REFERENCE TO RELATED APPLICATION

This application is a Section 371 of International Application No. PCT/CN2019/079492 filed Mar. 25, 2019, which was published in the Chinese language Oct. 3, 2019, under International Publication No. WO 2019/184866 A1, which claims priority under 35 U.S.C. § 119(b) to Chinese Patent Application No. 201810275072.5 filed Mar. 30, 2018, the disclosures of which are incorporated herein by reference in their entireties.

FIELD OF THE INVENTION

The present invention relates to the technical field of medicines, and in particular to phosphate derivatives and uses thereof in inhibiting tumor proliferation and metastasis.

BACKGROUND OF THE INVENTION

The micro-environment of solid tumor includes three characters, low extracellular pH, hypoxia, high absorptivity of glucose. These three are closely relevant, and mutually synergistic, to promote tumor occurrence, proliferation, invasion, and metastasis. Glycometabolism were processed via two pathways, mitochondria oxidative phosphorylation and glycolysis. The normal cell metabolite through aerobic circulation, mitochondria oxidative phosphorylation, while tumor cell via glycolysis (anaerobic and aerobic glycolysis). Malignant tumor takes in glycose extremely high, up to 12 times comparing to normal cell, and positron emission tomography PET scan utilized this principle, applicating $2-^{18}F$-FDG ([18-F]-fluorodeoxyglucose)) to image the tumor (*Ann Surg* 2005; 241 (2):286-94; Schwartz D L, et al.). The overquick growth of cancer cell caused the anaerobic condition, which chased the cancer cell to shut down the pathway of mitochondria oxidative phosphorylation, and open up the anaerobic glycosis. The glycometabolism to the pyruvic acid was not able to proceed via TCA of mitochondria oxidative phosphorylation, instead of lactic dehydrogenase (LDH), and the lactic was produced and eliminated out of cell. The anaerobic environment automatically promoted the glycolysis, and the final production of glycolysis was lactate. This kind of abnormal glycolysis of cancel cell directly created the acidic tumor microenvironment. The acidic environment accelerated tumor proliferation dramatically, and promoted the invasion of cancel cell to normal cells, meanwhile increased cancel cell capability of adaptation and modulation to this wicked environment. On the other hand, the anaerobic acidic microenvironment was tightly but negatively associated to the drug resistance.

The ambitus microenvironment of malignant tumor had a pH (pHe) of 6.5-6.9, the core could reach 6.2, comparably, the normal cell pH 7.3-7.5. The saliva of normal person was of pH 6.5-7.4, but cancer patient lower to pH 4.5-5.7.

The acidic microenvironment of malignant tumor was generated mainly by below aspects. Warguru effect caused the aggregation of lactic acid, the anoxia drove the carbonic anhydrase and proton transporter. Both aspects co-worked and promoted the excellular pH value decreased. Tumor cell took up a large amount of glucose, highly-efficiently turned the glucose to big volume of lactic acid, which was transported to the excellular microenvironment by mono carboxylic acid transporter MCT. The intracellular generated $CO_2$ was released to the excellular via diffusion, due to the anoxia, hypoxia-inducible factor 1 (HIF-1) induced the cancer cell to highly express CA-IX, and promote $CO_2$ with $H_2O$ to generate form carbonic acid. Therefore, the acidic microenvironment of malignant tumor was generated mainly by glycosis and hypoxia.

Tumor cell itself were adapt to the acidic micro-environment, via a mechanism of autophage, or upregulation of transporter and so on. Through cancer adaptive mechanism, the cancer cell pump out the proton out of the cell, and kept inner cell as a basic environment. In this process the acidic environment was closely related to drug resistance, through Na/H exchanger (NHE), Na/K ATPase, H-ATPases (vacuolar-H ATPase, V-ATPase), H/C1 co-transporter and monocarboxylate transporter (MCT), upregulation of VEGF and so on.

The acidic microenvironment of cancer was the greatest weapon to its invasion and metastasis. This acidity stimulated cancer cell itself to produce growth factor, grow new blood vessel, control apoptosis, proliferate unlimitedly, and immuno-escape. From the occurrence of cancer to all steps of cancer progress, the acidic environment was playing an important role as important pushing hands. (*Cancer Res* 2006; 66(10):521 6-23).

An acidic pHe, on the other hand, induces significant toxicity in normal cells by reducing proliferation [Id.] and promoting apoptosis via a p53-dependent pathway [Park H J, et al., Acidic environment causes apoptosis by increasing caspase activity. *Brit J Cancer* 1999; 80(1 2):1 892-7] initiated by increasing caspase activity [Williams A C, et al., An acidic environment leads to p53 dependent induction of apoptosis in human adenoma and carcinoma cell lines: implications for clonal selection during colorectal carcinogenesis. *Oncogene* 1999; 1 8(21):31 99-204]. In addition, an acidic pHe in normal tissues increases degradation of the extracellular matrix due to the production and release of proteolytic enzymes [Rozhin J, et al., *Cancer Res* 1994; 54(24):651 7-25], promotes angiogenesis through release of VEGF [Shi Q, et al., *Oncogene* 2001; 20(28):3751-6], and limits immune response to tumor antigens [Lardner A. The effects of extracellular pH on immune function. *J Leukocyte Biol* 2001; 69(4):522-30].

Because of the importance of TME to tumor, many scientists and researchers performed a number of studies. Rorbert Gillies proved the oral or IP sodium bicarbonate increased the tumor pHe by Magnetic Resonance Spectrum, and inhibited spontaneous metastasis, and tumor proliferation (Cancer Research 2009, 69 (6), 2260.). An acidic pHe, on the other hand, induces significant toxicity in normal cells by reducing proliferation [Id.] and promoting apoptosis via a p53-dependent pathway [Park H J, et al., Acidic environment causes apoptosis by increasing caspase activity. *Brit J Cancer* 1999; 80(1 2):1 892-7] initiated by increasing caspase activity [Williams A C, et al., An acidic environment leads to p53 dependent induction of apoptosis in human adenoma and carcinoma cell lines: implications for clonal selection during colorectal carcinogenesis. *Oncogene* 1999; 1 8(21):31 99-204]. In addition, an acidic pHe in normal tissues increases degradation of the extracellular matrix due to the production and release of proteolytic enzymes [Rozhin J, et al., *Cancer Res* 1994; 54(24):651 7-25], promotes angiogenesis through release of VEGF [Shi Q, et al., *Oncogene* 2001; 20(28):3751-6], and limits immune response to tumor antigens [Lardner A. The effects of extracellular pH on immune function. *J Leukocyte Biol* 2001; 69(4):522-30].

Cancer metastasis was the primary reason of clinical treatment failure. Over 80% of cancer patients died of cancer metastasis. The accumulation of lactic acid in solid tumor not only reflected the grade malignancy, also was closely related to its farther metastasis. Cancer metastasis meant that lymph-vessel, the cancer cell departed from the original organ, and invaded lymph-vessel, blood vessel, body cavity, and migrate to other organ to regrow, and formed the same type of cancer as the original cancer. The benign tumor did not migrate, and only the malignant tumor did. The general migration pathways included lymphatic metastasis, blood route metastasis, cultivate metastasis. In the metastasis, lactic acid mediated the process. Lactic acid was able to pass MCT1 and enter endothelial cells, and gave rise to the degradation and phosphorylation of IκBα, and further irritate autocrine transcription factor κB/IL-8 pathway, and generate the migration and blood vessel formation. The research found that in human colon cancer and breast cancer xenograft model, the lactic acid transported by MCT4, and stimulated IL-8 dependent cancer cell to grow and generate blood vessel. And the tumor metastasis was realized. Lactic acid mediated the body immune response to cancer cell, and resulted the diffusion of cancer cell. Research turned out acidic acid not only existed in every step, but also involved every step of cancer development.

Dr. Robert Gillies Florida H. LEE MOFFITT Cancer Center, studied the anticancer and inhibiting cancer metastasis using sodium bicarbonate, imidazole and its derivatives, Tris, Lysine and on with buffering capability to buffer the tumor acidic micro environment, and reported the definite results. All these buffers were effective to inhibit cancer proliferation and metastasis. Quite impressively, Arizona University did the clinical trial using sodium bicarbonate, and tried to prove this concept in clinical.

These findings have been synthesized into the acid-mediated tumor invasion model, which proposes that intratumoral acidosis results in the flow of H+ ions along concentration gradients into normal tissue adjacent to the tumor. This produces a peritumoral ring of dead and dying cells and a degraded extracellular matrix into which the still viable malignant cells invade [Gatenby R A, et al., A reaction-diffusion model of cancer invasion. *Cancer Res* 1996; 56(24):5745-53; Gatenby R A, et al., Acid-mediated tumor invasion: a multidisciplinary study. *Cancer Res* 2006; 66(1 0):521 6-23]. The model is supported by experimental evidence demonstrating a peritumoral acid gradient associated with normal cell apoptosis and extracellular matrix degradation.

Currently a number of studies and experimental evidences showed that increasing pH value of tumor microenvironment effectively inhibit the cancer proliferation and metastasis. Therefore, the acidic microenvironment of solid tumor is a very potential target of treating cancer, especially for cancer metastasis, and was sorted into the frontier of the immuno-oncology.

Therefore, the biomedicine field is in urgent needs of modulator to regulate the tumor acidic microenvironment, especially the small molecules with high pH value and buffering capability.

Definitions

The term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation or metastasis of the tumor. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer. As used herein, "treatment" refers to obtaining beneficial or desired clinical results. Beneficial desired clinical results include, but are not limited to, any one or more of alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total). The methods of the invention contemplate any one or more of these aspects of treatment. A "subject in need of treatment" is a mammal with cancer that is life-threatening or that impairs health or shortens the lifespan of the mammal.

A "pharmaceutically acceptable" component is one that is suitable for use with humans and/or animals without undue adverse side effects (such as toxicity, irritation, and allergic response) commensurate with a reasonable benefit/risk ratio.

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "consisting of" shall mean excluding more than trace elements of other components or steps.

As used herein, the term "pretreating", or "pretreatment", is intended to mean that a first treatment is administered prior to, or in conjunction with, a second treatment. In other words, the pretreatment may be performed before another, later treatment, thus allowing the pretreatment time to take effect. Alternatively, the pretreatment may be performed or administered simultaneously with a second treatment without a temporal delay.

SUMMARY OF THE INVENTION

The technical problem to be solved for the invention is to provide a small molecule which can effectively increase the pH value of the tumor microenvironment. The present invention provides a novel type of phosphate derivatives that have a pH value over 8 with monodentate or multidentate base function groups, and it can modulate the acidity of the tumor microenvironment, effectively inhibit cancer proliferation and metastasis, to get better therapeutic effect on cancers in clinic.

In order to solve the above technical problem, the present invention is implemented by the following technical solutions.

In one aspect, the present invention provides a compound with a formula (I),

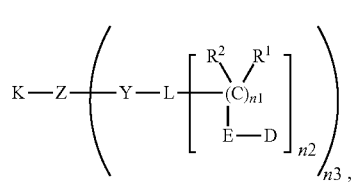

(I)

or a tautomer, mesomer, racemate, enantiomer, and diastereoisomer thereof, or a mixture form thereof, or a pharmaceutically acceptable salt thereof, or a prodrug molecule thereof, wherein L is selected from a group consisting of $C_1$-$C_{10}$ alkyl, cycloalkyl, cycloalkylalkyl, alkylcycloalkyl, aryl, arylalkyl, alkylaryl, heteroaryl, heteroarylalkyl, alkylheteroaryl, alkenyl, alkynyl, a $C_3$-$C_{15}$ linear or branched chain containing an N, O, or S atom, a linear or branched chain consisting of repeating units of $C_1$-$C_{15}$ linear or branched chains containing N, or O, or S atoms, cascade bisaryl, cascade bisheteroaryl, cascade aryl and heteroaryl, and bisaryl and bisheteroaryl linked by N, O, S or

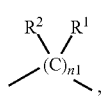

wherein the alkyl, the cycloalkyl, the heterocyclyl, the aryl or the heteroaryl may be each independently substituted by one or more substituents selected from a group consisting of hydroxyl, halogen, alkyl, alkoxyl, cycloalkyl, heterocyclyl, aryl, and heteroaryl;

Y and Z are independently selected from a group consisting of NR1, O, S,

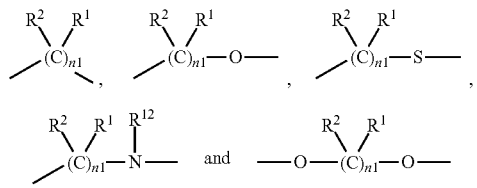

respectively, or are null;

D is selected from a group consisting of

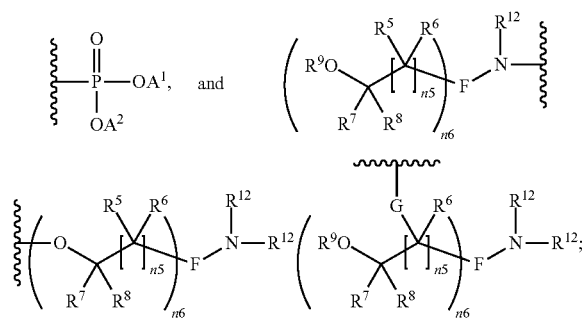

when D is selected as

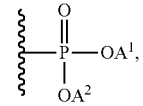

K is selected from

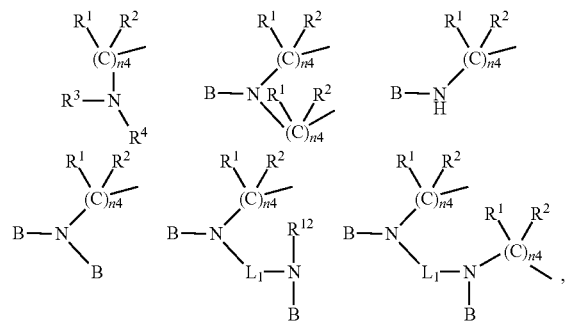

with B selected from a group consisting of

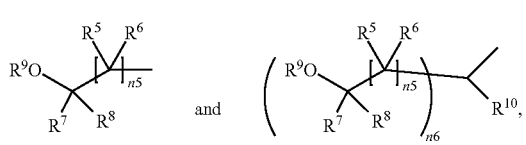

and preferably being trihydroxymethylmethyl;
when D is selected from

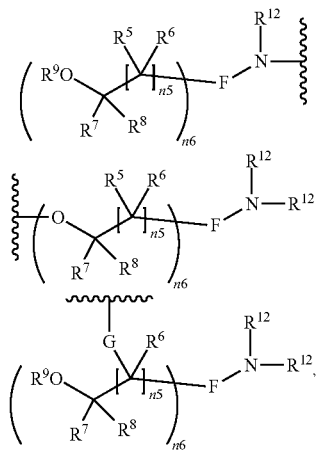

K is selected as

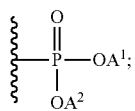

F is $CR^{10}$ or null;
G is selected from a group consisting of

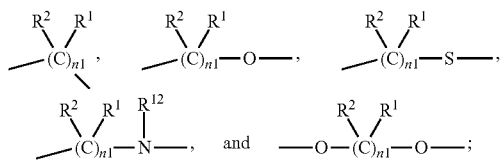

$R^1$ and $R^2$ are each independently selected from a group consisting of hydrogen, halogen, alkyl, cycloalkyl, hydroxyalkane, alkoxylalkyl, alkoxylcycloalkyl, cycloalkylalkyl, alkylcycloalkyl, alkenyl, alkynyl, amino, hydroxyl, mercapto, carboxyl, alkoxyl, cycloalkoxyl, haloalkyl, cyano, thioalkyl, sulfo, sulfonyl, sulfinyl, phosphate, alkylphosphonate, arylphosphate, and arylphosphonate, wherein the alkyl, the cycloalkyl, the heterocyclyl, the aryl, or the heteroaryl may be each independently substituted by one or more substituents selected from a group consisting of hydroxyl, halogen, alkyl, alkoxyl, cycloalkyl, heterocyclyl, aryl, and heteroaryl, or may be null;

$R^3$ and $R^4$ are each independently selected from a group consisting of hydrogen, alkyl, cycloalkyl, cycloalkylalkyl, alkylcycloalkyl, aryl, arylalkyl, alkylaryl, heteroaryl, heteroarylalkyl, alkylheteroaryl, heterocyclyl, heterocyclylalkyl, alkylheterocyclyl, alkenylalkyl, and alkynylalkyl, wherein the alkyl, the cycloalkyl, the cycloalkylalkyl, the alkylcycloalkyl, the aryl, the arylalkyl, the alkylaryl, the heteroaryl, the heteroarylalkyl, the alkylheteroaryl, the heterocyclyl, the heterocyclylalkyl, the alkylheterocyclyl, the alkenylalkyl, or the alkynylalkyl is not substituted or is substituted by one or more substituents, each of which is selected from a group consisting of alkyl, cycloalkyl, cycloalkylalkyl, alkylcycloalkyl, aryl, arylalkyl, alkylaryl, heteroaryl, heteroarylalkyl, alkylheteroaryl, heterocyclyl, heterocyclylalkyl, alkylheterocyclyl, alkenyl, alkynyl, amino, hydroxyl, mercapto, carboxyl, alkoxyl, cycloalkoxyl, haloalkyl, alkoxycarbonyl, acyloxy, amido, ureido, alkylsulfonyl, arylsulfonyl, haloalkyl, halogen, cyano, nitro, nitroso, thiocyano, isothiocyano, thioalkyl, sulfo, phosphate, phosphonate, alkylphosphate, alkylphosphonate, arylphosphate, and arylphosphonate;

or $R^3$ and $R^4$ together with a nitrogen atom for linking $R^3$ and $R^4$ form heterocyclyl, which is a monocyclic ring, a bicyclic ring or a tricyclic ring, or a fused ring, a bridge ring or a spiro-ring, wherein the heterocyclyl includes at least one N atom or one, two or three heteroatoms optionally selected from N, S and O, and is not substituted or is optionally substituted by one or more substituents, each of which is independently selected from a group consisting of alkyl, cycloalkyl, cycloalkylalkyl, alkylcycloalkyl, aryl, arylalkyl, alkylaryl, heteroaryl, heteroarylalkyl, alkylheteroaryl, heterocyclyl, heterocyclylalkyl, alkylheterocyclyl, alkenyl, alkynyl, amino, hydroxyl, mercapto, carboxyl, alkoxyl, cycloalkoxyl, haloalkyl, alkoxycarbonyl, acyloxy, amido, ureido, alkylsulfonyl, arylsulfonyl, haloalkyl, halogen, cyano, nitro, nitroso, thiocyano, isothiocyano, thioalkyl, sulfo, phosphate, phosphonate, alkylphosphate, alkylphosphonate, arylphosphate, and arylphosphonate, which are used as a substituent alone or in a free combination thereof;

$A^1$ and $A^2$ are each independently selected from a group consisting of H, Li, Na, K, Cs, and a corresponding positive ion thereof, or $A^1$ and $A^2$ form Ca, Mg, Al, Sc, Ti, Cr, Co, Fe, Ni, Cu, Zn, Cd, Hg, and a corresponding positive ion thereof, collectively;

E is selected from a group consisting of oxygen and $C(R^1R^2)$;

$R^5$ and $R^6$ are each independently selected from a group consisting of a hydrogen atom, halogen, alkyl, alkoxyalkyl, cycloalkyl, alkoxycycloalkyl, hydroxyalkyl, hydroxycycloalkyl, heterocyclyl, aryl and heteroaryl, wherein the alkyl, the cycloalkyl, the heterocyclyl, the aryl or the heteroaryl may be each independently substituted by one or more substituents selected from a group consisting of hydroxyl, halogen, alkyl, alkoxyl, cycloalkyl, heterocyclyl, aryl, and heteroaryl; or $R^5$ and $R^6$ may form a 3-membered to 8-membered ring, which may contain 1 to 2 heteroatoms of O, N and/or S;

$R^7$ and $R^8$ are each independently selected from a group consisting of a hydrogen atom, alkyl, hydroxyalkyl, cycloalkyl, alkoxyalkyl, alkoxycycloalkyl, heterocyclyl, aryl and heteroaryl, wherein the alkyl, the cycloalkyl, the heterocyclyl, the aryl or the heteroaryl may be each independently substituted by one or more substituents selected from a group consisting of hydroxyl, halogen, alkyl, alkoxy, cycloalkyl, heterocyclyl, aryl and heteroaryl;

$R^9$ is selected from a group consisting of a hydrogen atom, halogen, alkane, alkoxylalkyl, cycloalkyl, alkoxylcycloalkyl, hydroxyalkyl, hydroxycycloalkyl, heterocyclyl, aryl, heteroaryl and acyl, wherein the alkane, the alkoxylalkyl, the cycloalkyl, alkoxylcycloalkyl, hydroxyalkyl, hydroxycycloalkyl, heterocyclyl, aryl, heteroaryl and acyl may be each independently substituted by one or more substituents selected from a group consisting of hydroxyl, halogen, alkyl, alkoxy, cycloalkyl, heterocyclyl, aryl, and heteroaryl;

$R^{10}$ is selected from a group consisting of a hydrogen atom, halogen, alkane, cycloalkyl, heterocyclyl, aryl, and heteroaryl, or is null, wherein the alkane, the cycloalkyl, the heterocyclyl, the aryl, or the heteroaryl may be each independently substituted by one or more substituents selected from a group consisting of hydroxyl, halogen, alkyl, alkoxy, cycloalkyl, heterocyclyl, aryl, and heteroaryl;

$R^{12}$ is selected from a group consisting of a hydrogen atom, alkane, alkoxylalkyl, cycloalkyl, alkoxylcycloalkyl, hydroxyalkyl, hydroxycycloalkyl, heterocyclyl, aryl, heteroaryl, heterocyclylalkyl, arylalkyl and heteroarylalkyl, wherein the alkane, the alkoxylalkyl, the cycloalkyl, the alkoxylcycloalkyl, the hydroxyalkyl, the hydroxycycloalkyl, the heterocyclyl, the aryl, the heteroaryl, the heterocyclylalkyl, the arylalkyl and the heteroarylalkyl may be each independently substituted by one or more substituents selected from a group consisting of hydroxyl, halogen, alkyl, alkoxy, cycloalkyl, heterocyclyl, aryl and heteroaryl;

n1 is selected from a group consisting of 0, 1, 2, 3, 4, 5, 6, 7, and 8;

n2 is selected from a group consisting of 1, 2, 3, 4, 5, and 6;

n3 is selected from a group consisting of 1, 2, and 3;

n4 is selected from a group consisting of 0, 1, 2, 3, and 4;

n5 is selected from a group consisting of 0, 1, 2, and 3; and n6 is selected from a group consisting of 1, 2, and 3.

Preferably, the compound may be a compound shown in a formula (II),

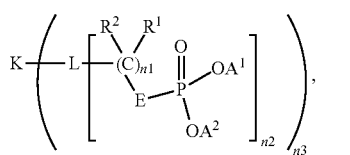

(II)

or a tautomer, mesomer, racemate, enantiomer, and diastereoisomer thereof, or a mixture form thereof, or a pharmaceutically acceptable salt thereof, or a prodrug molecule thereof, wherein L is selected from a group consisting of C1-C10 alkyl, cycloalkyl, cycloalkylalkyl, alkylcycloalkyl, aryl, arylalkyl, alkylaryl, heteroaryl, heteroarylalkyl, alkylheteroaryl, alkenyl, alkynyl, a C3-C15 linear or branched chain containing an N, O, or S atom, a linear or branched chain consisting of repeating units of C1-C15 linear or branched chains containing N, or O, or S atoms, cascade bisaryl, cascade bisheteroaryl, cascade aryl and heteroaryl, and bisaryl and bisheteroaryl linked by N, O, S or

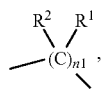

wherein the alkyl, the cycloalkyl, the heterocyclyl, the aryl or the heteroaryl may be each independently substituted by one or more substituents selected from a group consisting of hydroxyl, halogen, alkyl, alkoxyl, cycloalkyl, heterocyclyl, aryl, and heteroaryl, and preferably one or more substituents selected from a group consisting of phenyl and naphthyl;

$R^1$ and $R^2$ are each independently selected from a group consisting of hydrogen, halogen, alkyl, cycloalkyl, hydroxyalkane, alkoxylalkyl, alkoxylcycloalkyl, cycloalkylalkyl, alkylcycloalkyl, alkenyl, alkynyl, amino, hydroxyl, mercapto, carboxyl, alkoxyl, cycloalkoxyl, haloalkyl, cyano, thioalkyl, sulfo, sulfonyl, sulfinyl, phosphate, alkylphosphonate, arylphosphate, and arylphosphonate, wherein the alkyl, the cycloalkyl, the heterocyclyl, the aryl, or the heteroaryl may be each independently substituted by one or more substituents selected from a group consisting of hydroxyl, halogen, alkyl, alkoxyl, cycloalkyl, heterocyclyl, aryl, and heteroaryl;

K is selected from a group consisting of

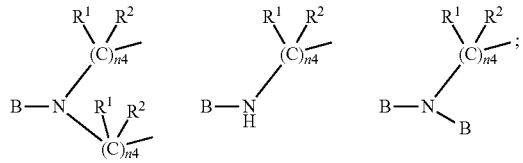

B is selected from a group consisting of

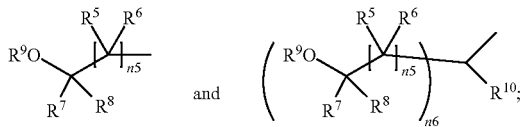

$A^1$ and $A^2$ are each independently selected from a group consisting of H, Li, Na, K, Cs, and a corresponding positive ion thereof, or $A^1$ and $A^2$ form Ca, Mg, Al, Sc, Ti, Cr, Co, Fe, Ni, Cu, Zn, Cd, Hg, and a corresponding positive ion thereof, collectively;

E is selected from a group consisting of $C(R^1R^2)$;

$R^5$ and $R^6$ are each independently selected from a group consisting of a hydrogen atom, halogen, alkyl, alkoxyalkyl, cycloalkyl, alkoxycycloalkyl, heterocyclyl, aryl and heteroaryl, wherein the alkyl, the cycloalkyl, the heterocyclyl, the aryl or the heteroaryl may be each independently substituted by one or more substituents selected from a group consisting of hydroxyl, halogen, alkyl, alkoxyl, cycloalkyl, heterocyclyl, aryl, and heteroaryl; or $R^5$ and $R^6$ may form a 3-membered to 8-membered ring, which may contain 1 to 2 heteroatoms of O, N and/or S;

$R^7$ and $R^8$ are each independently selected from a group consisting of a hydrogen atom, alkyl, hydroxyalkyl, cycloalkyl, alkoxyalkyl, alkoxycycloalkyl, heterocyclyl, aryl and heteroaryl, wherein the alkyl, the cycloalkyl, the heterocyclyl, the aryl or the heteroaryl may be each independently substituted by one or more substituents selected from a group consisting of hydroxyl, halogen, alkyl, alkoxy, cycloalkyl, heterocyclyl, aryl and heteroaryl;

$R^9$ is selected from a group consisting of a hydrogen atom, alkyl, cycloalkyl, heterocyclyl, aryl, and heteroaryl, wherein the alkyl, the cycloalkyl, the heterocyclyl, the aryl, or the heteroaryl may be each independently substituted by one or more substituents selected from a group consisting of hydroxyl, halogen, alkyl, alkoxy, cycloalkyl, heterocyclyl, aryl, and heteroaryl;

$R^{10}$ is selected from a group consisting of a hydrogen atom, halogen, alkyl, cycloalkyl, heterocyclyl, aryl, and heteroaryl, or is null, wherein the alkyl, the cycloalkyl, the heterocyclyl, the aryl, or the heteroaryl may be each independently substituted by one or more substituents selected from a group consisting of hydroxyl, halogen, alkyl, alkoxy, cycloalkyl, heterocyclyl, aryl, and heteroaryl;

n1 is selected from a group consisting of 0, 1, 2, 3, 4, 5, 6, 7, and 8;

n2 is selected from a group consisting of 1, 2, 3, 4, 5, and 6;

n3 is selected from a group consisting of 1, 2, and 3;

n4 is selected from a group consisting of 0, 1, 2, 3, and 4;

n5 is selected from a group consisting of 0, 1, 2, and 3;

and n6 is selected from a group consisting of 1, 2, and 3.

Preferably, the compound may be a compound shown in a formula (II),

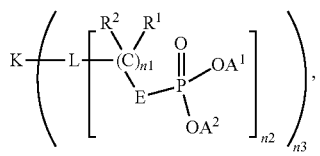
(II)

or a tautomer, mesomer, racemate, enantiomer, and diastereoisomer thereof, or a mixture form thereof, or a pharmaceutically acceptable salt thereof, or a prodrug molecule thereof, wherein

K

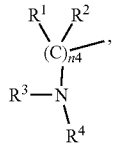

or E is an oxygen atom;

$R^3$ and $R^4$ are each independently selected from a group consisting of hydrogen, alkyl, cycloalkyl, cycloalkylalkyl, alkylcycloalkyl, aryl, arylalkyl, alkylaryl, heteroaryl, heteroarylalkyl, alkylheteroaryl, heterocyclyl, heterocyclylalkyl, alkylheterocyclyl, alkenylalkyl, and alkynylalkyl, wherein the alkyl, the cycloalkyl, the cycloalkylalkyl, the alkylcycloalkyl, the aryl, the arylalkyl, the alkylaryl, the heteroaryl, the heteroarylalkyl, the alkylheteroaryl, the heterocyclyl, the heterocyclylalkyl, the alkylheterocyclyl, the alkenylalkyl, or the alkynylalkyl is not substituted or is substituted by one or more substituents, each of which is selected from a group consisting of alkyl, cycloalkyl, cycloalkylalkyl, alkylcycloalkyl, aryl, arylalkyl, alkylaryl, heteroaryl, heteroarylalkyl, alkylheteroaryl, heterocyclyl, heterocyclylalkyl, alkylheterocyclyl, alkenyl, alkynyl, amino, hydroxyl, mercapto, carboxyl, alkoxyl, cycloalkoxyl, haloalkyl, alkoxycarbonyl, acyloxy, amido, ureido, alkylsulfonyl, arylsulfonyl, haloalkyl, halogen, cyano, nitro, nitroso, thiocyano, isothiocyano, thioalkyl, sulfo, phosphate, phosphonate, alkylphosphate, alkylphosphonate, arylphosphate, and arylphosphonate;

or $R^3$ and $R^4$ together with a nitrogen atom for linking $R^3$ and $R^4$ form heterocyclyl, which is a monocyclic ring, a bicyclic ring or a tricyclic ring, or a fused ring, a bridge ring or a spiro-ring, wherein the heterocyclyl includes at least one N atom or one, two or three heteroatoms optionally selected from N, S and O, and is not substituted or is optionally substituted by one or more substituents, each of which is independently selected from a group consisting of alkyl, cycloalkyl, cycloalkylalkyl, alkylcycloalkyl, aryl, arylalkyl, alkylaryl, heteroaryl, heteroarylalkyl, alkylheteroaryl, heterocyclyl, heterocyclylalkyl, alkylheterocyclyl, alkenyl, alkynyl, amino, hydroxyl, mercapto, carboxyl, alkoxyl, cycloalkoxyl, haloalkyl, alkoxycarbonyl, acyloxy, amido, ureido, alkylsulfonyl, arylsulfonyl, haloalkyl, halogen, cyano, nitro, nitroso, thiocyano, isothiocyano, thioalkyl, sulfo, phosphate, phosphonate, alkylphosphate, alkylphosphonate, arylphosphate, and arylphosphonate, which are used as a substituent alone or in a free combination thereof.

Preferably, the compound may be a compound shown in a formula (III),

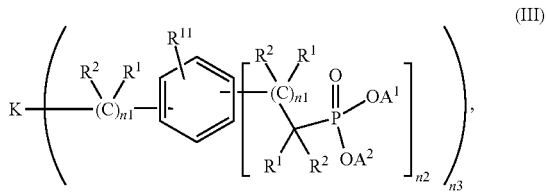
(III)

or a tautomer, mesomer, racemate, enantiomer, and diastereoisomer thereof, or a mixture form thereof, or a pharmaceutically acceptable salt thereof, or a prodrug molecule thereof, wherein $R^{11}$ is selected from a group consisting of hydrogen, halogen, C1-C6 alkyl, C3-C8 cycloalkyl, hydroxyalkane, alkoxylalkyl, alkoxylcycloalkyl, cycloalkylalkyl, alkylcycloalkyl, alkenyl, alkynyl, amino, hydroxyl, alkoxyl, cycloalkoxyl, haloalkyl, cyano, thioalkyl, sulfo, sulfonyl, sulfinyl, aryl or heteroaryl, wherein the alkyl, the cycloalkyl, the heterocyclyl, the aryl, or the heteroaryl may be each independently substituted by one or more substituents selected from a group consisting of hydroxyl, halogen, alkyl, alkoxyl, cycloalkyl, heterocyclyl, aryl, and heteroaryl.

Preferably, the compound may be a compound shown in a formula (IV),

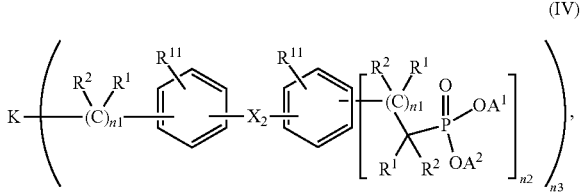
(IV)

or a tautomer, mesomer, racemate, enantiomer, and diastereoisomer thereof, or a mixture form thereof, or a pharmaceutically acceptable salt thereof, or a prodrug molecule thereof, wherein $X_2$ is selected from a group consisting of NR1, O, S,

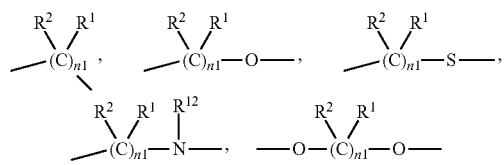

and a single bond, and a direct link between aryl and aryl is indicated when X is the single bond; and $R^{11}$ is selected from a group consisting of hydrogen, halogen, C1-C6 alkyl, C3-C8 cycloalkyl, hydroxyalkane, alkoxylalkyl, alkoxylcycloalkyl, cycloalkylalkyl, alkylcycloalkyl, alkenyl, alkynyl, amino, hydroxyl, alkoxyl, cycloalkoxyl, haloalkyl, cyano, thioalkyl, sulfo, sulfonyl, sulfinyl, aryl or heteroaryl, wherein the alkyl, the cycloalkyl, the heterocyclyl, the aryl, or the heteroaryl may be each independently substituted by one or more substituents selected from a group consisting of hydroxyl, halogen, alkyl, alkoxyl, cycloalkyl, heterocyclyl, aryl, and heteroaryl.

Preferably, the compound with the formula (I) includes the compounds with the following specific structures:

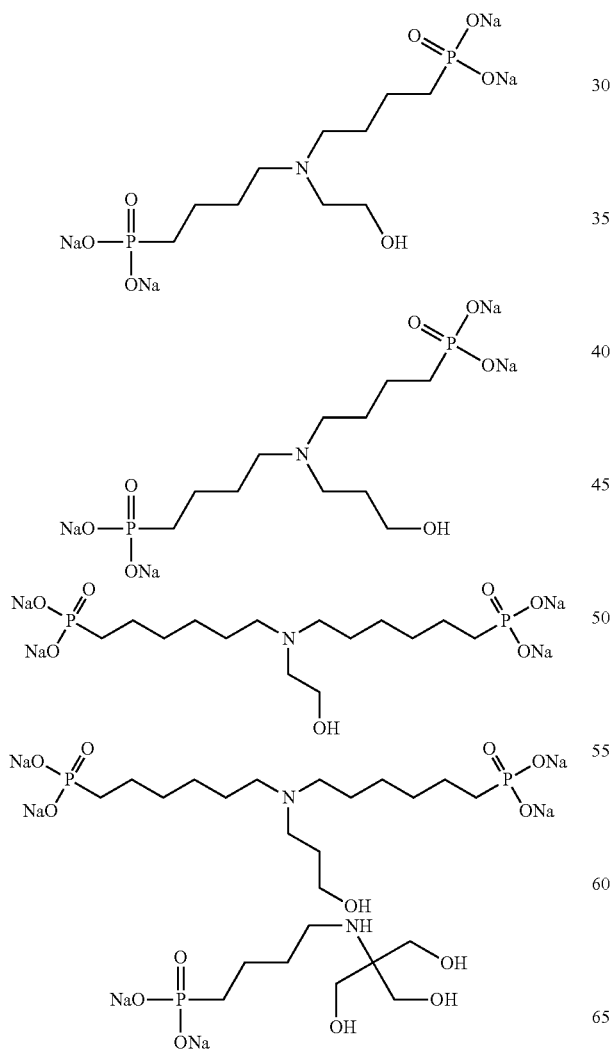

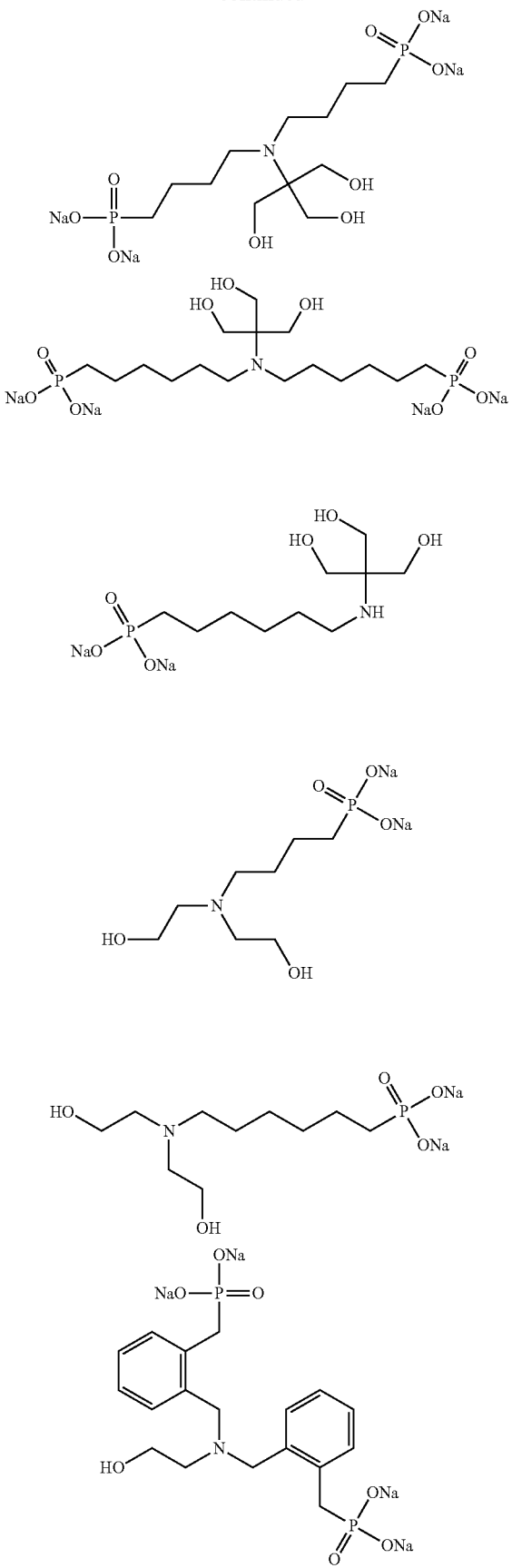

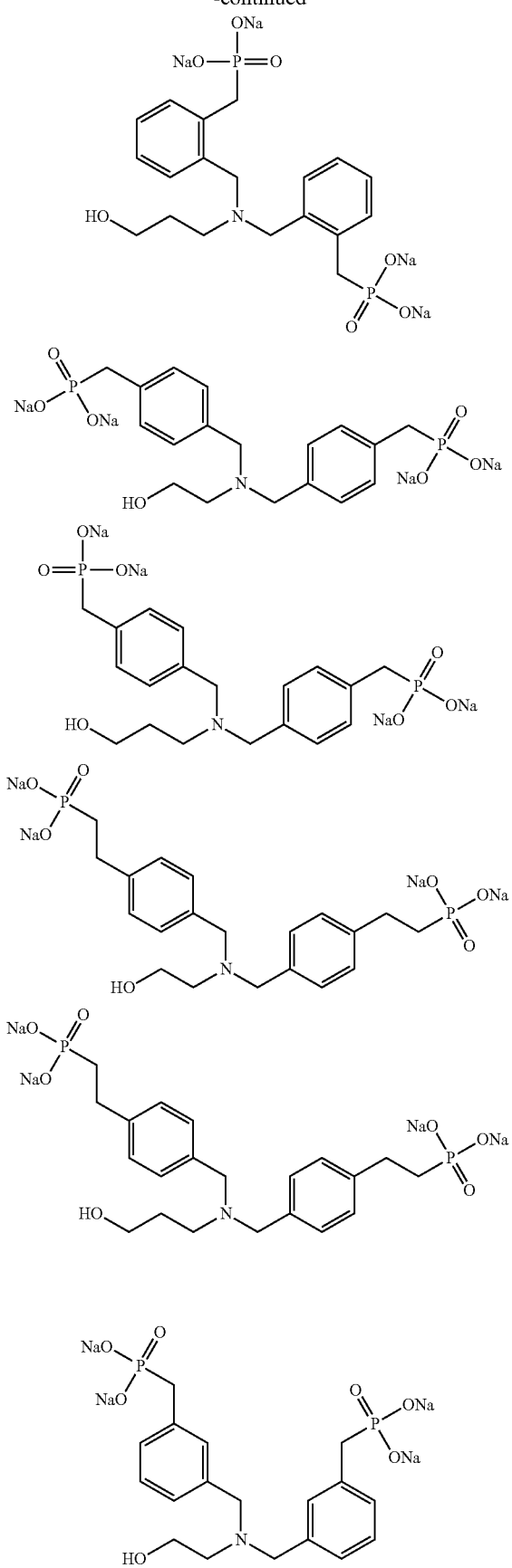
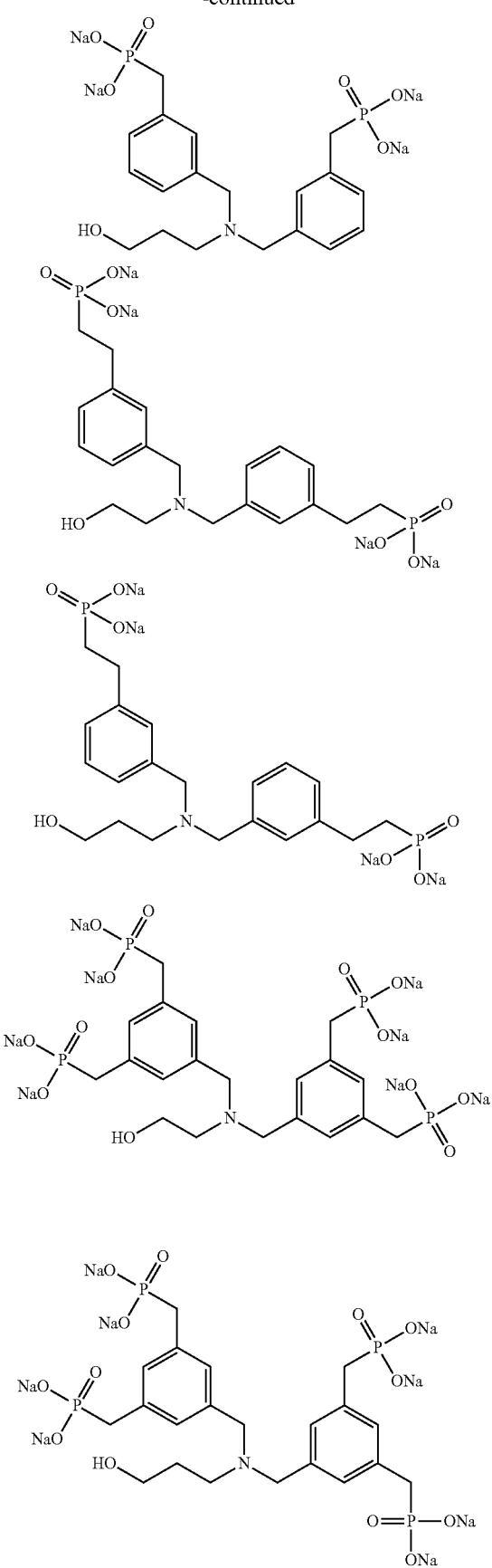

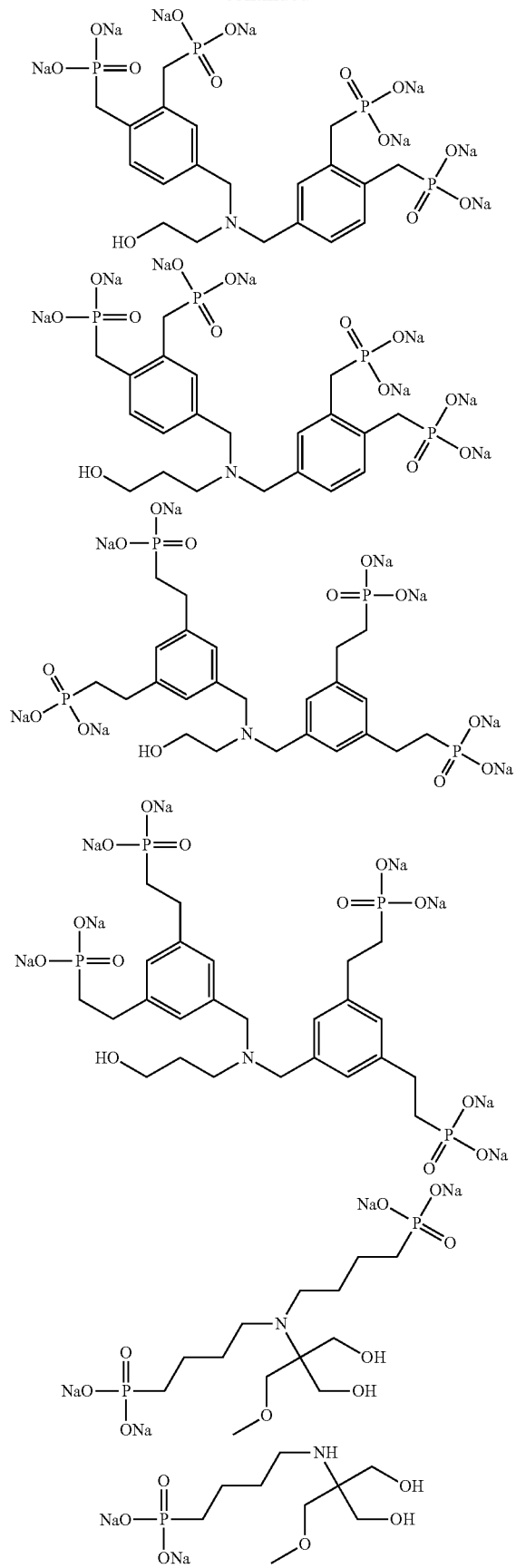
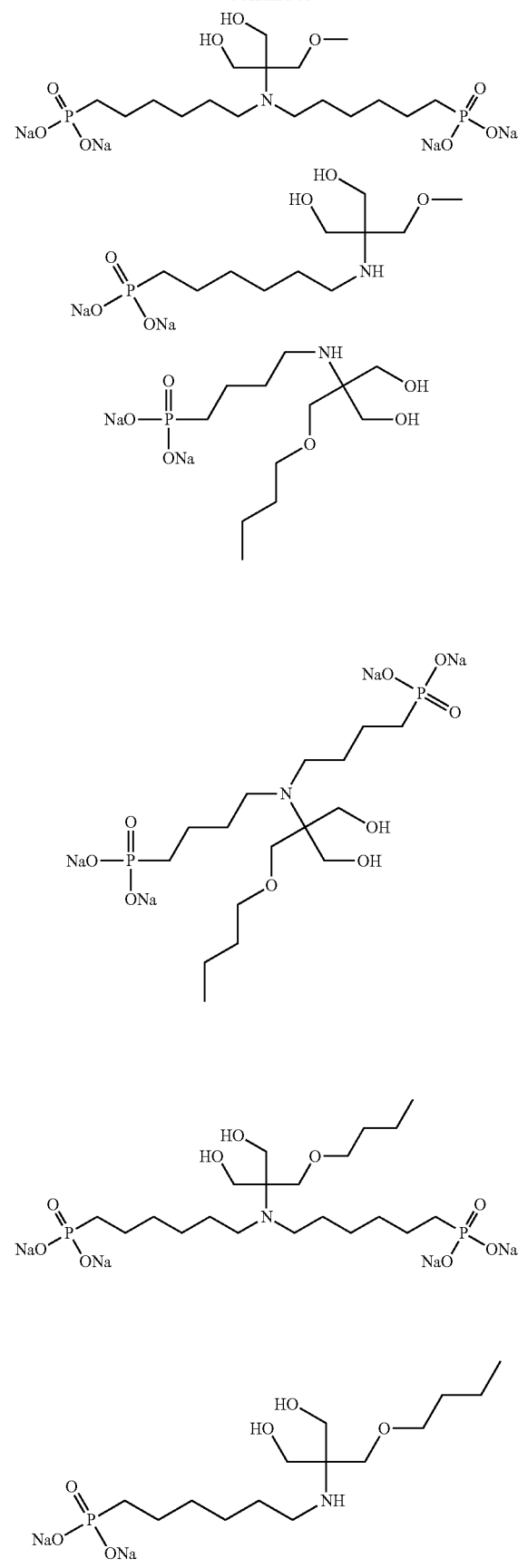

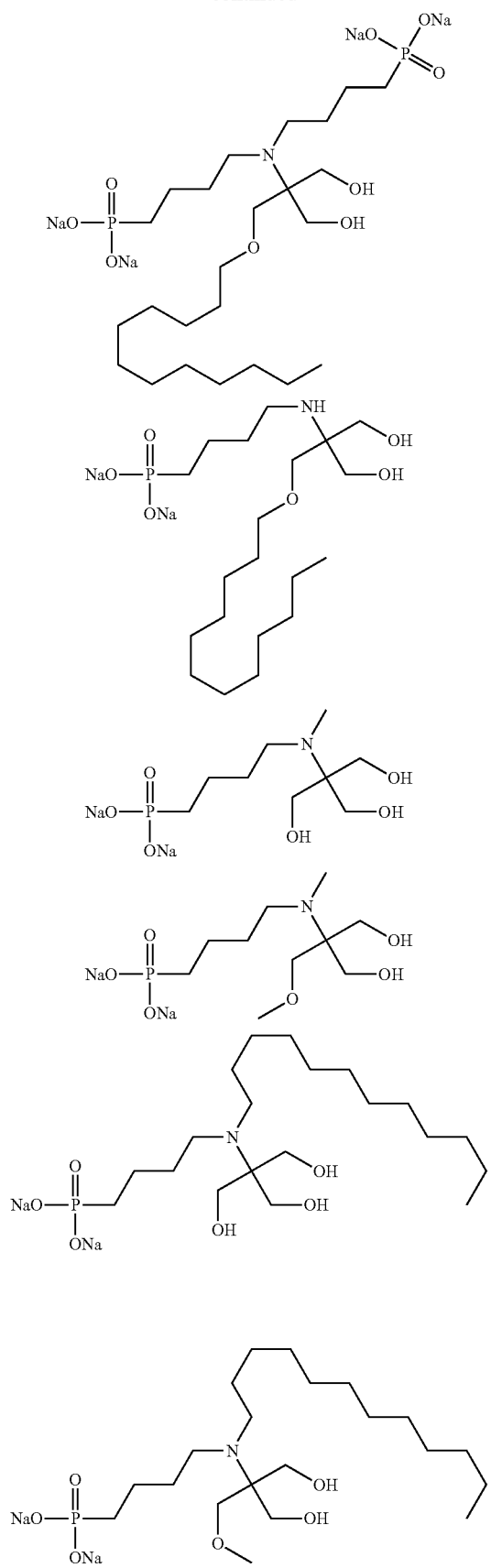
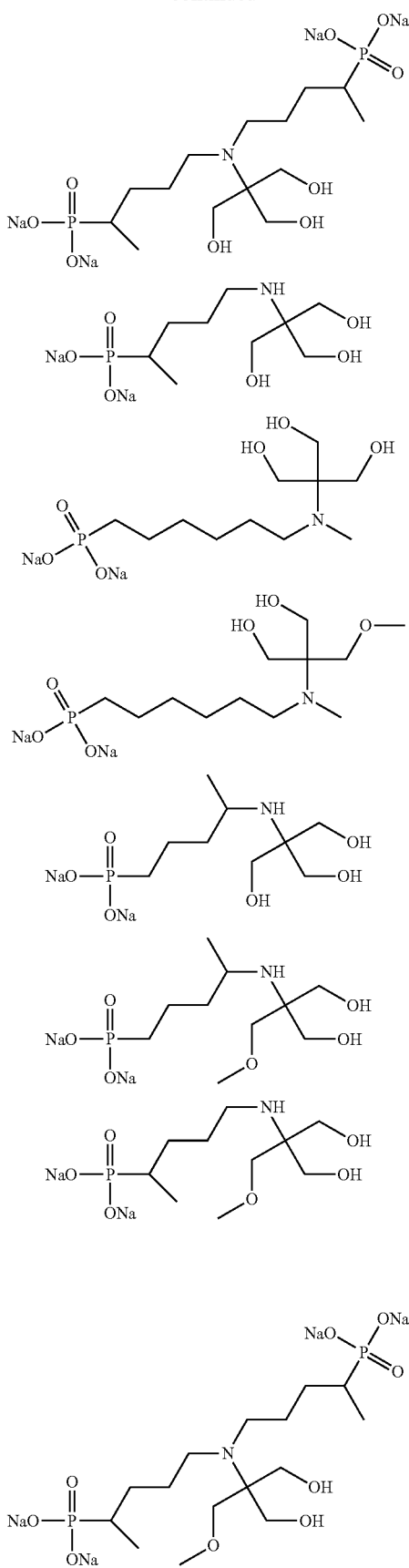

21
-continued
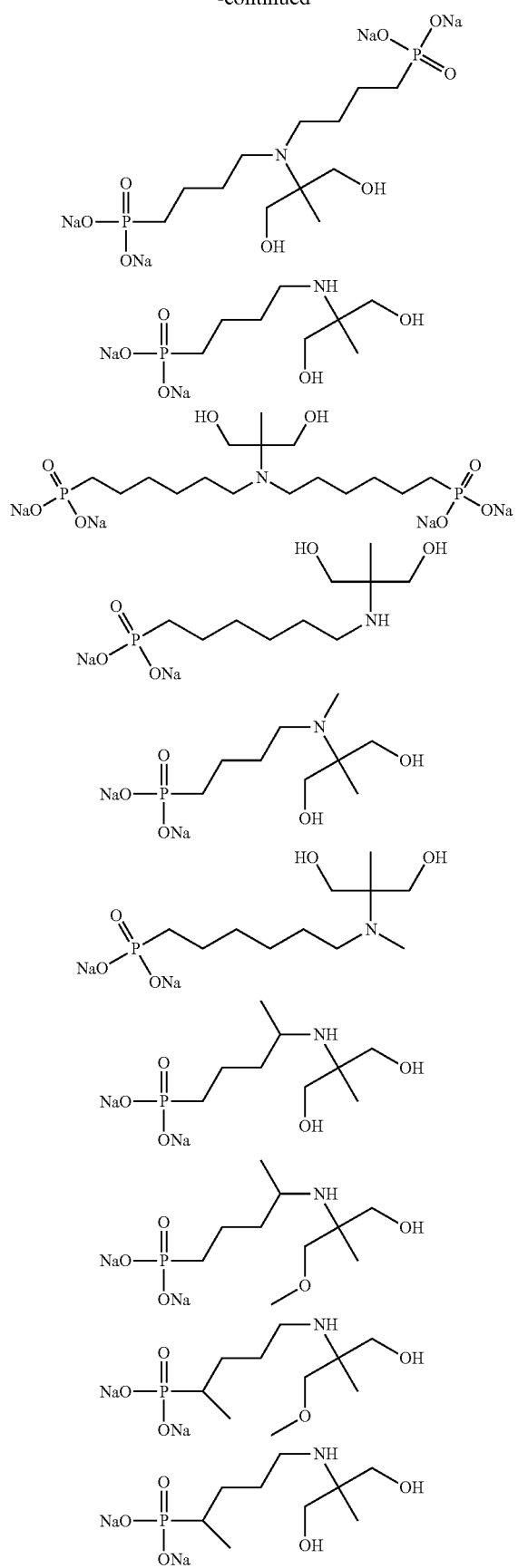
22
-continued
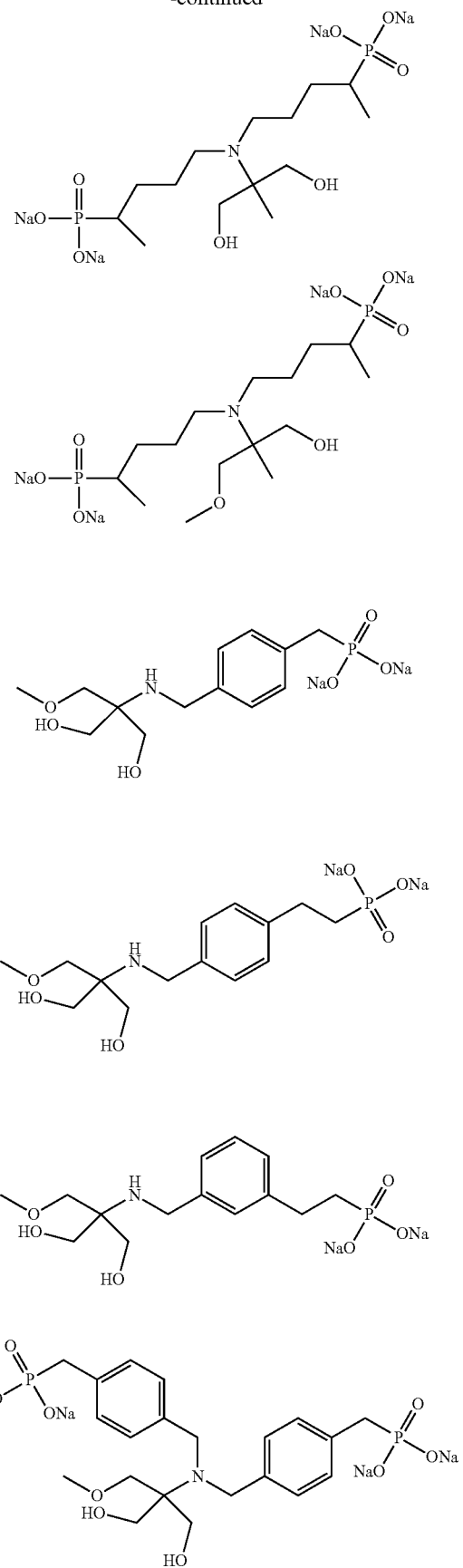

23
-continued
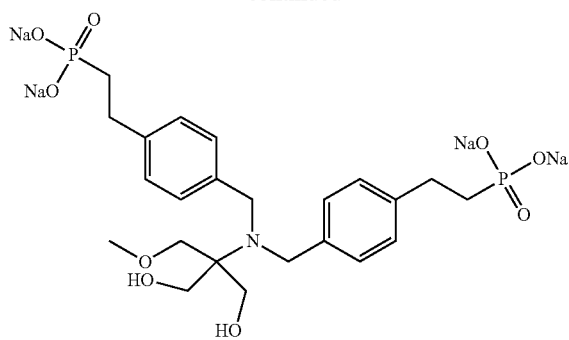
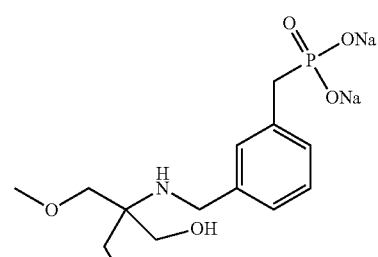
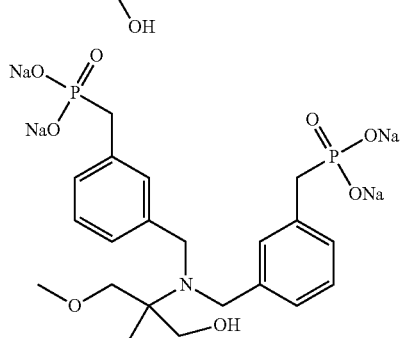
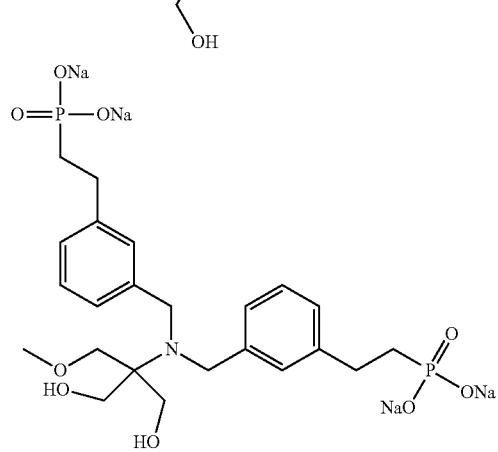
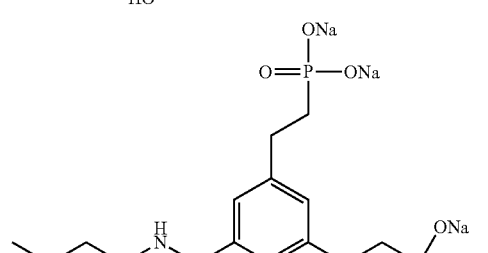
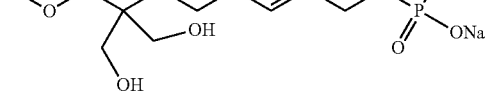
24
-continued
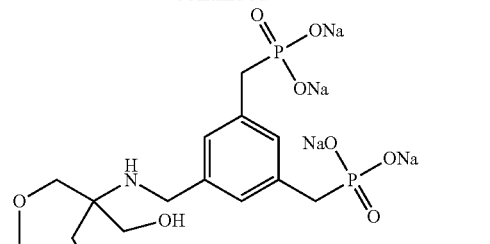
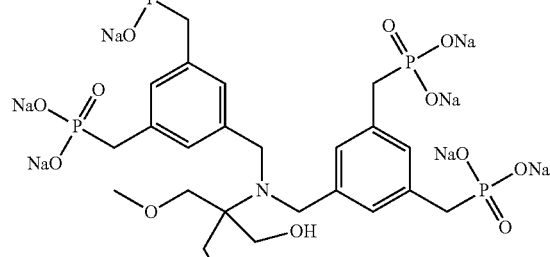
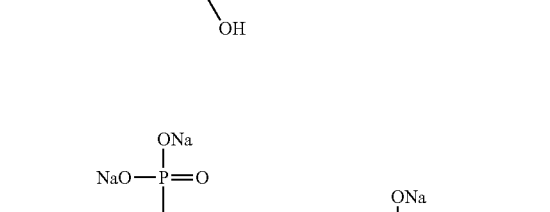
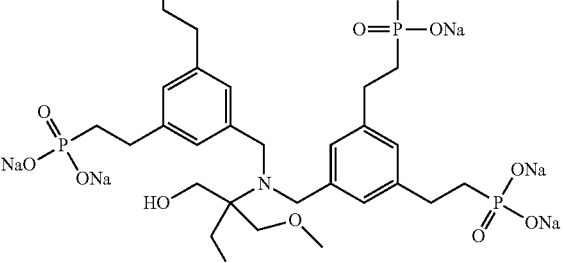
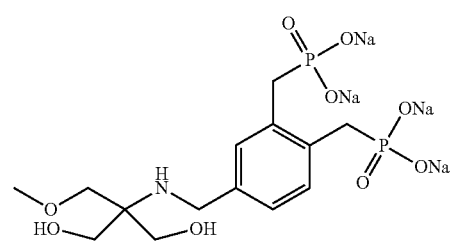
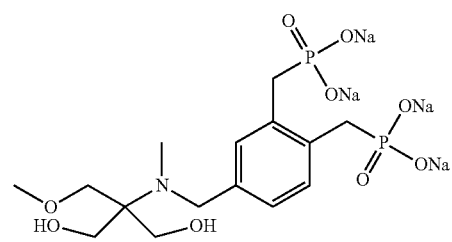

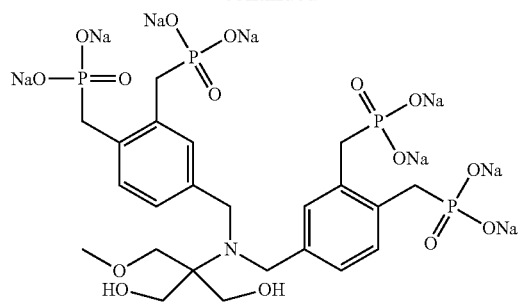
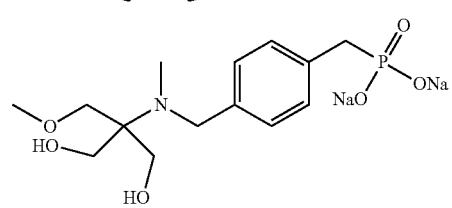
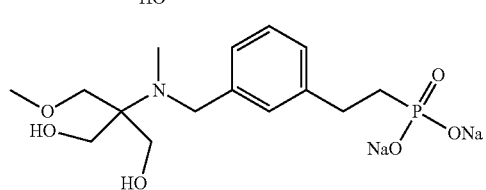
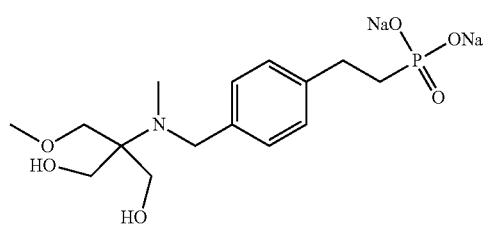
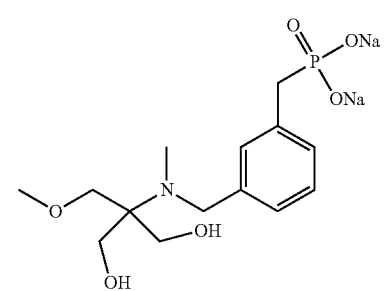
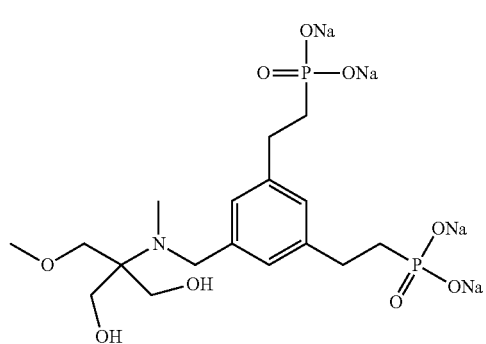
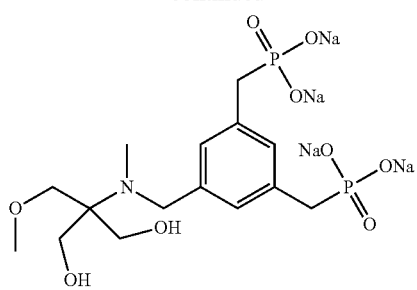
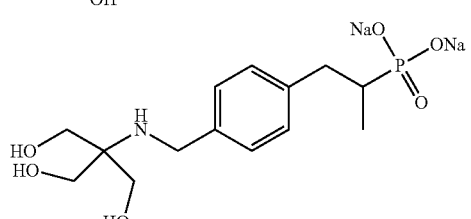
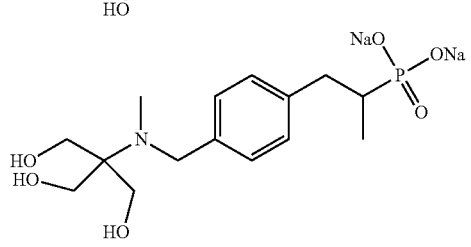
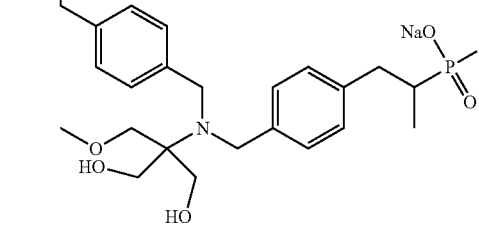
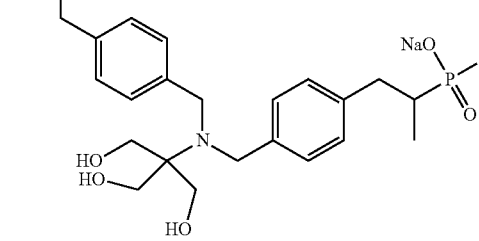
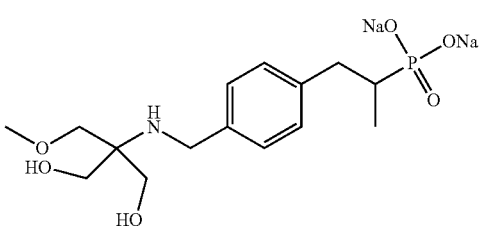

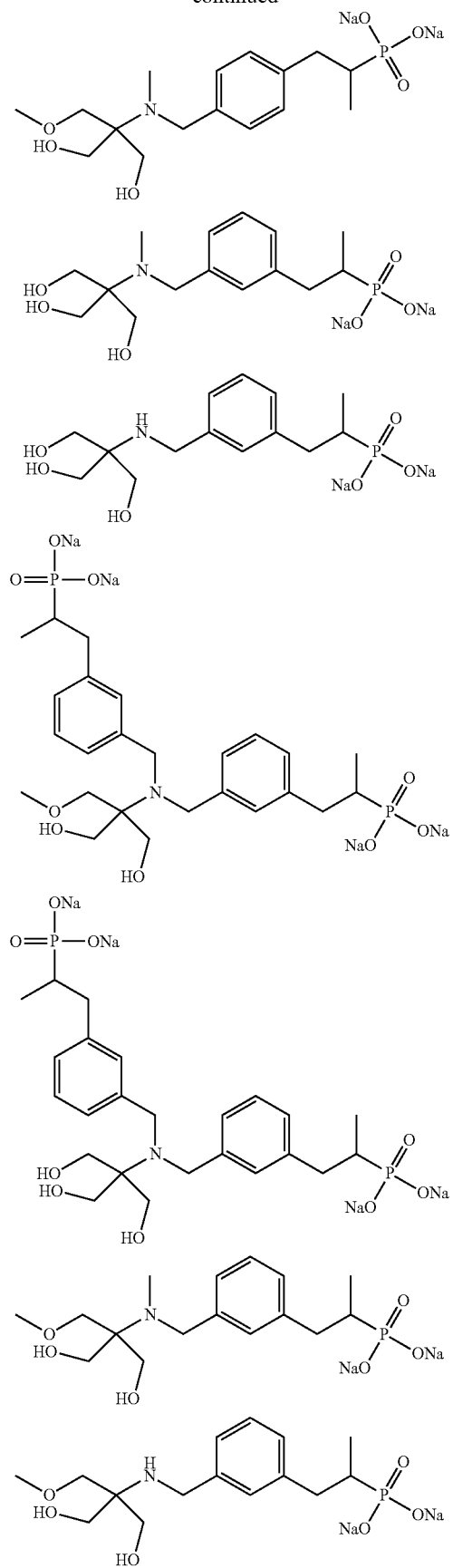
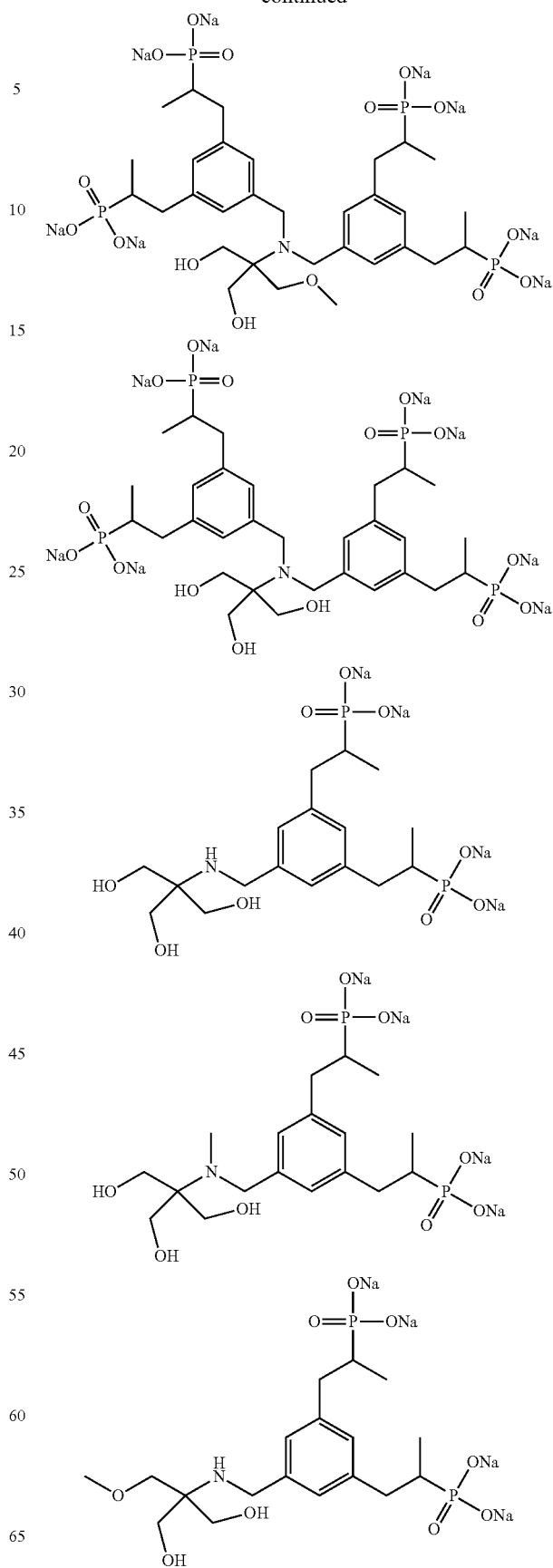

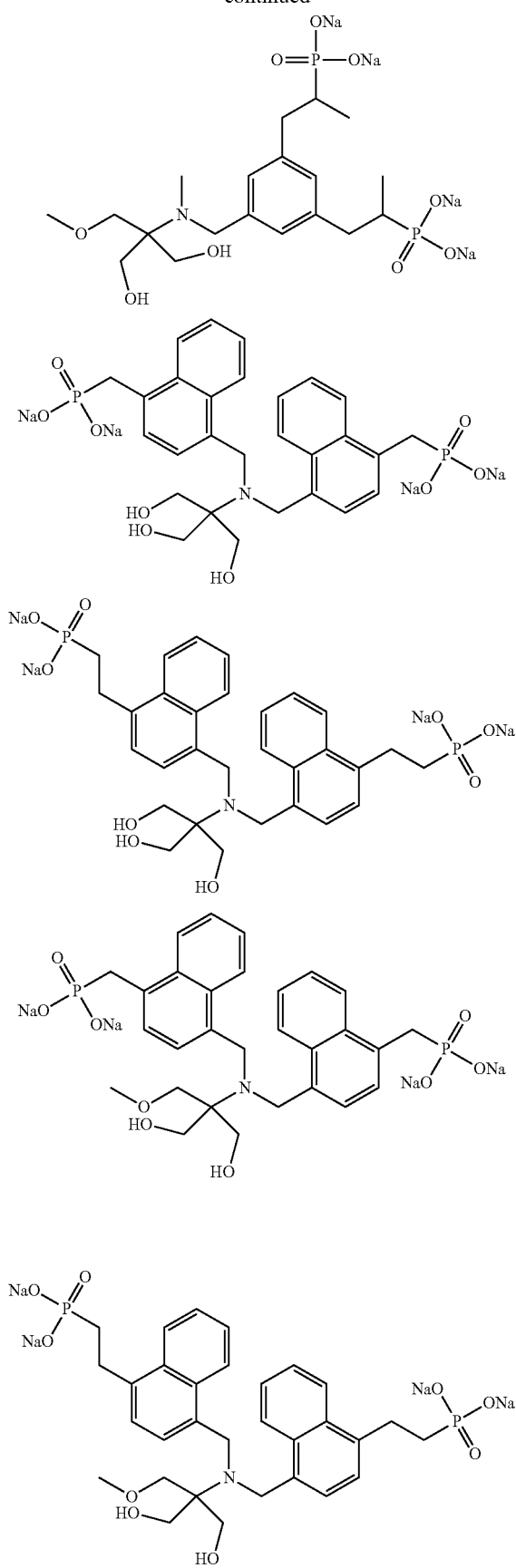
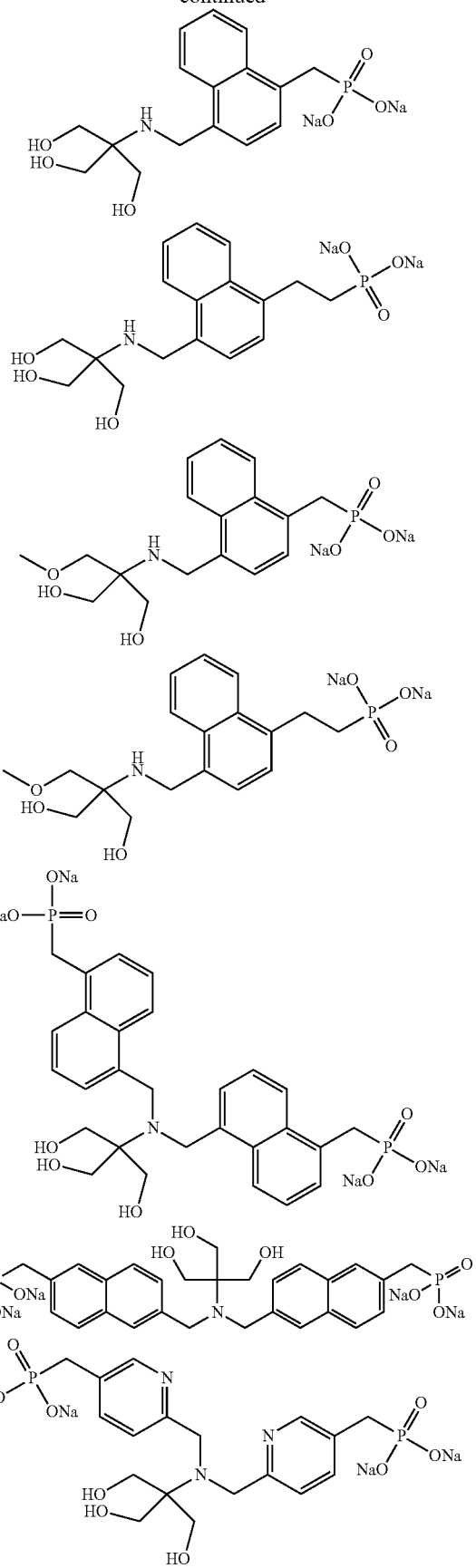

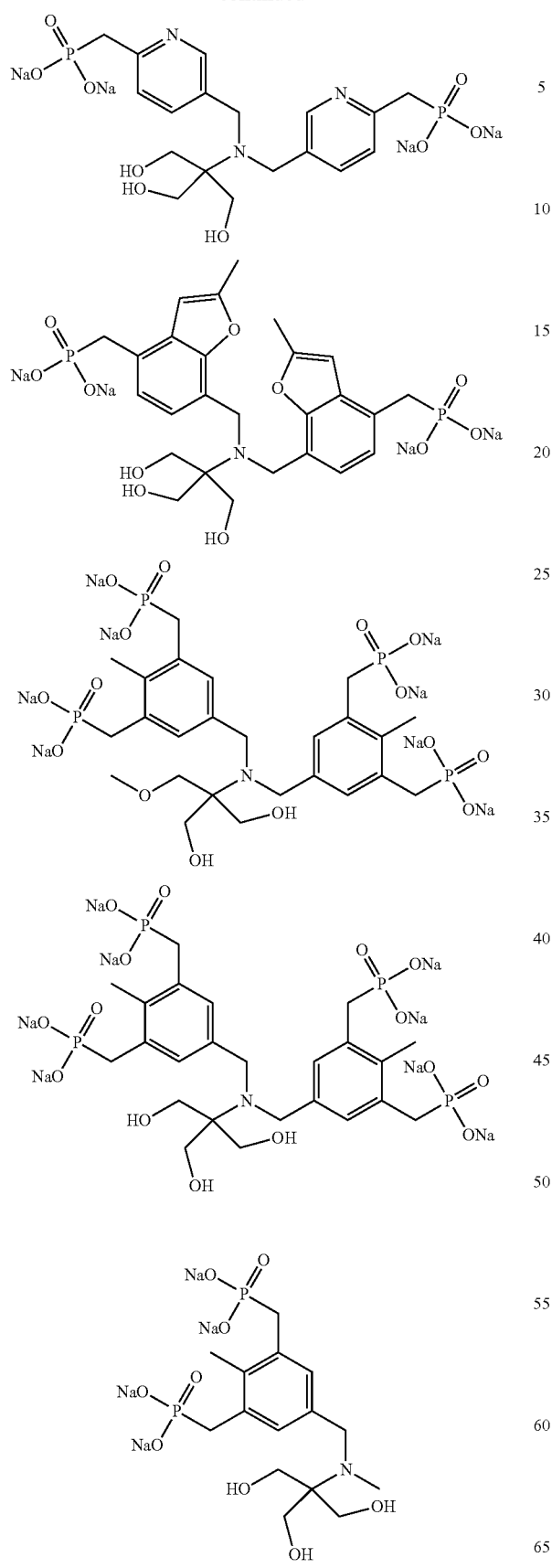
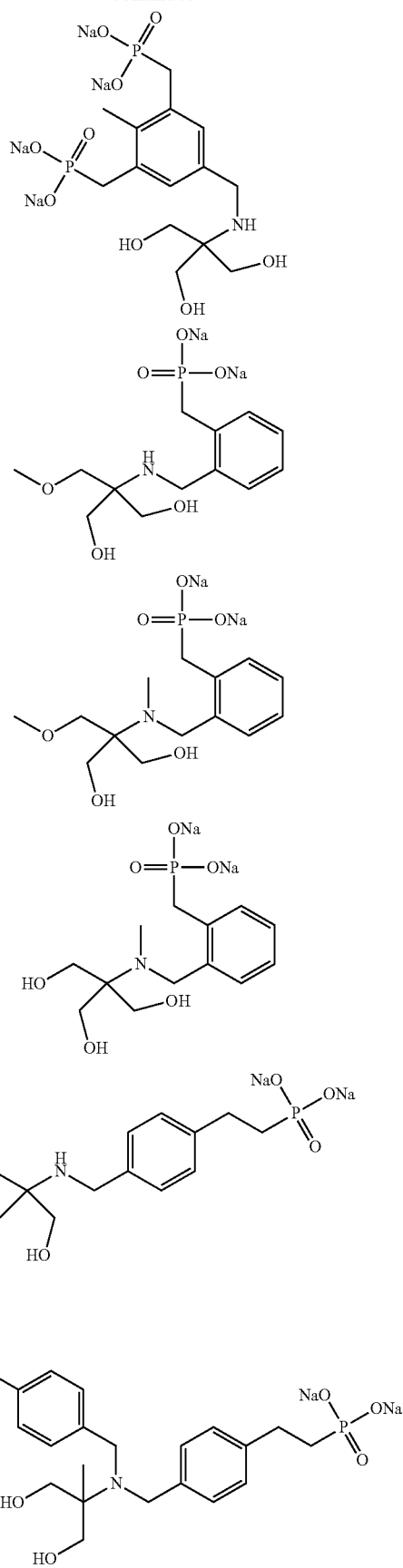

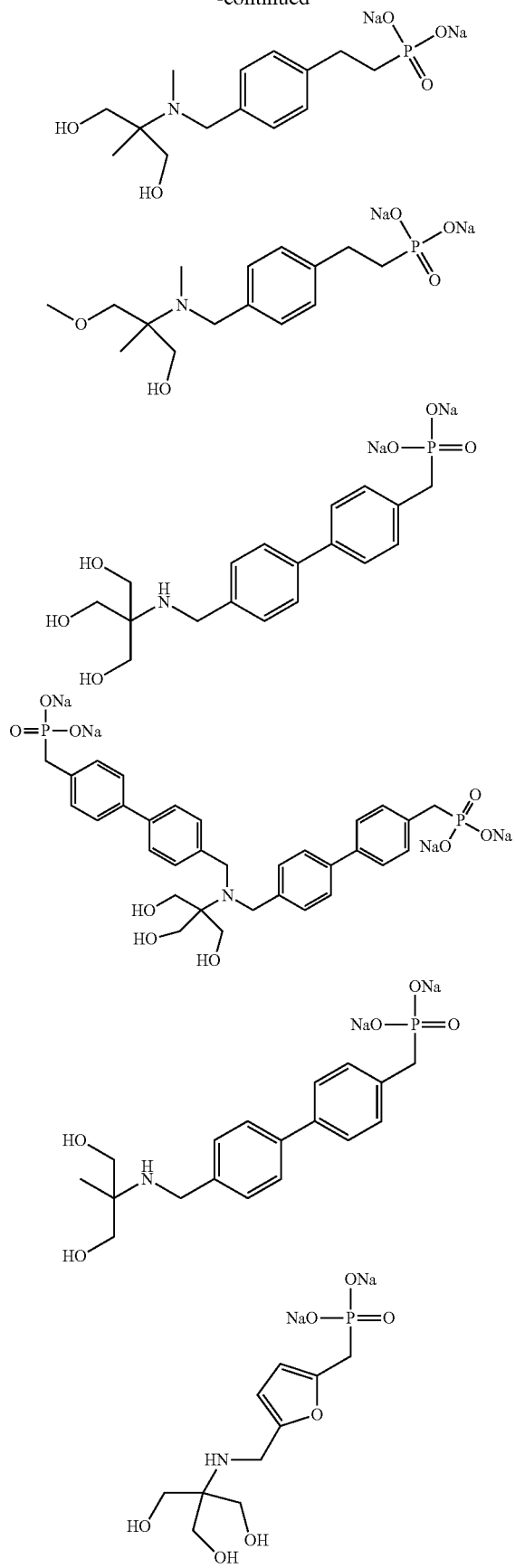

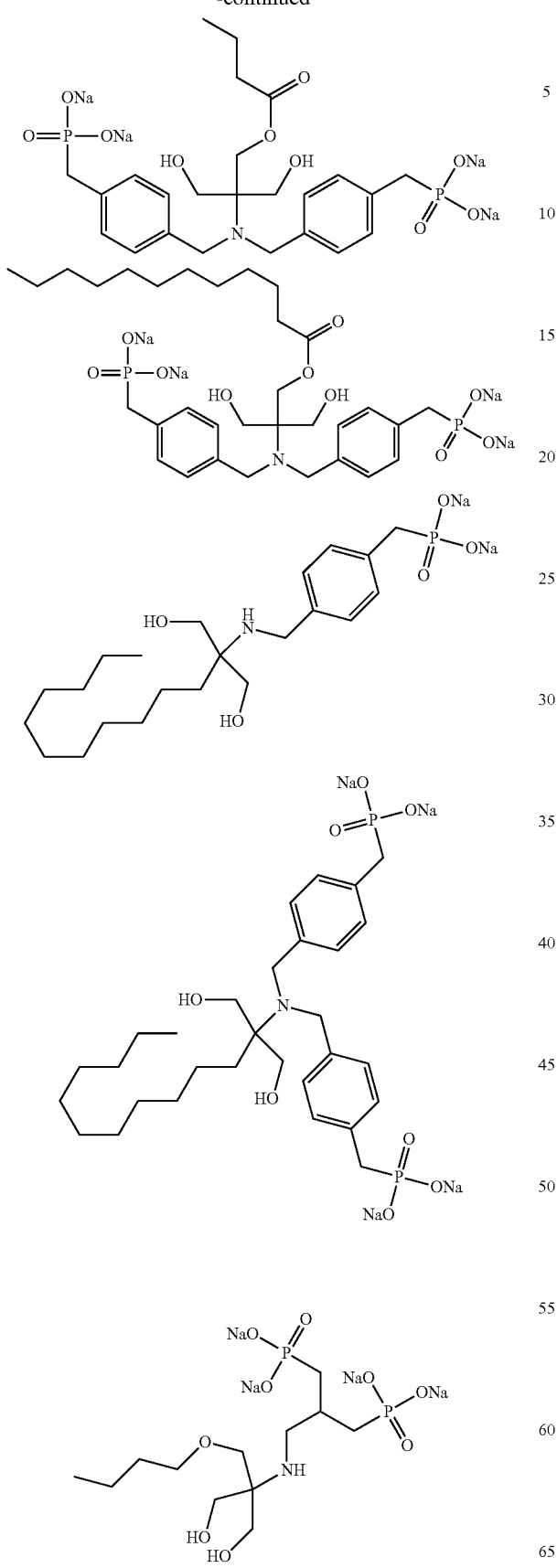
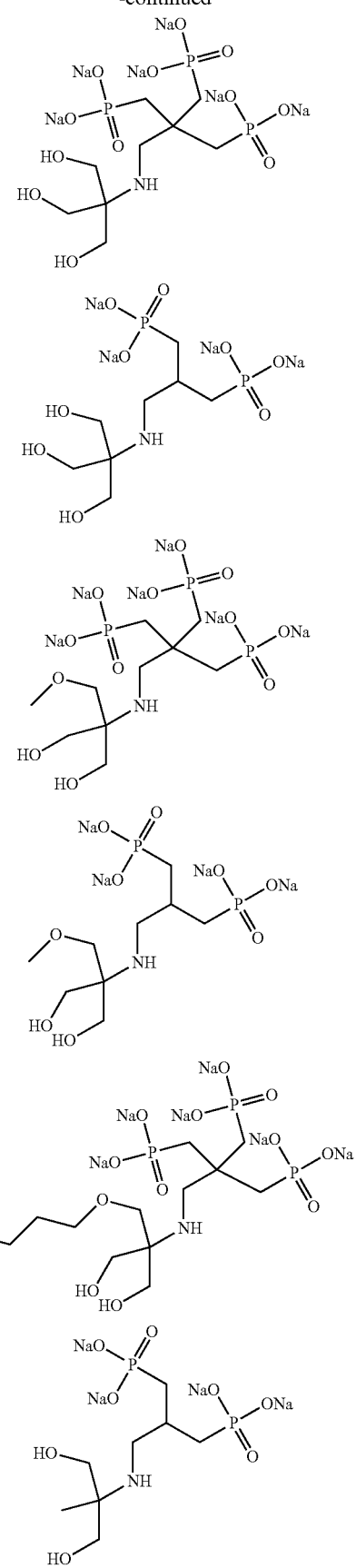

-continued
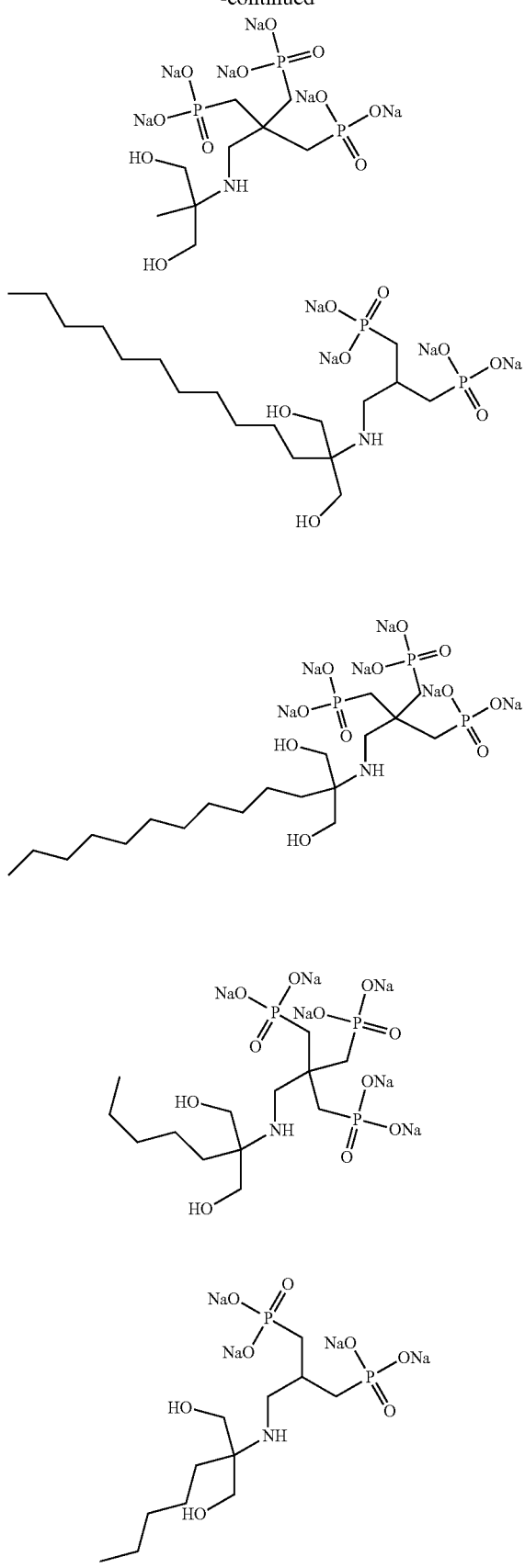
-continued
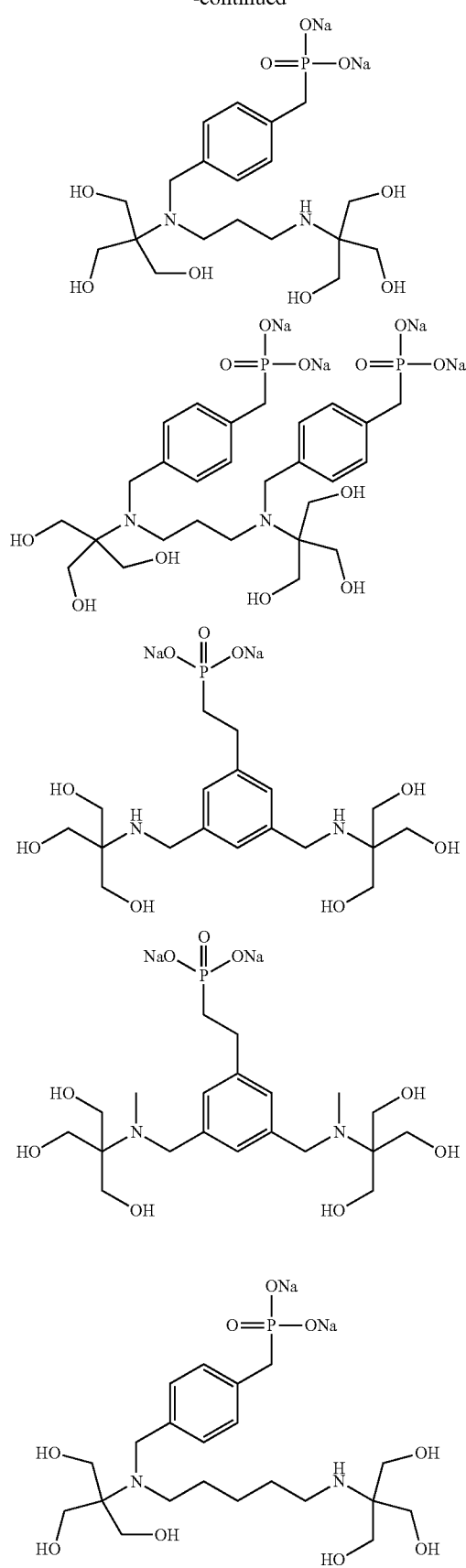

-continued
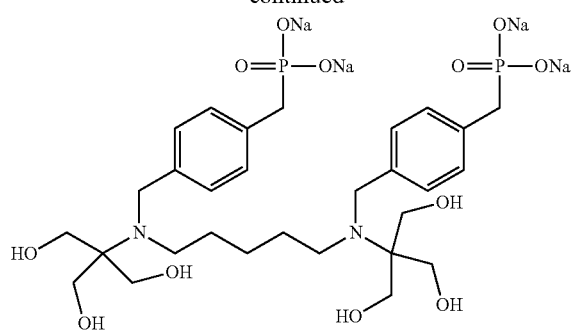
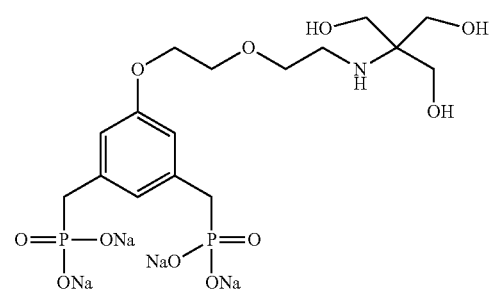
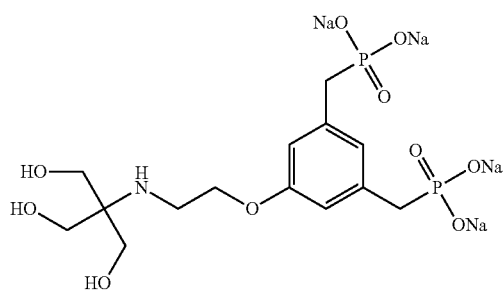
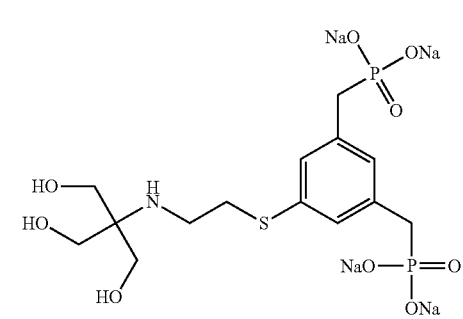
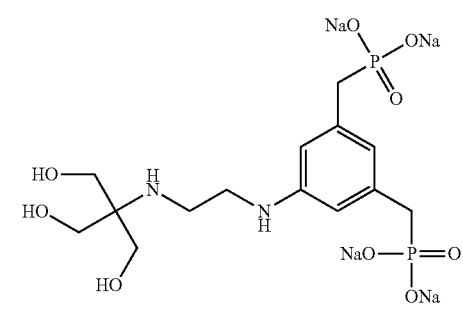
-continued
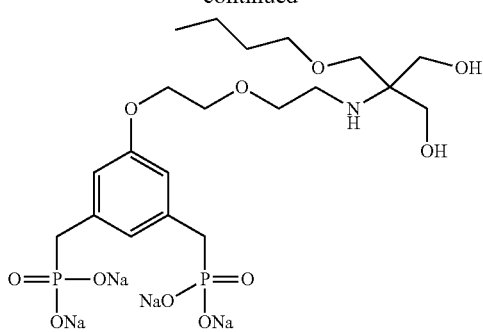
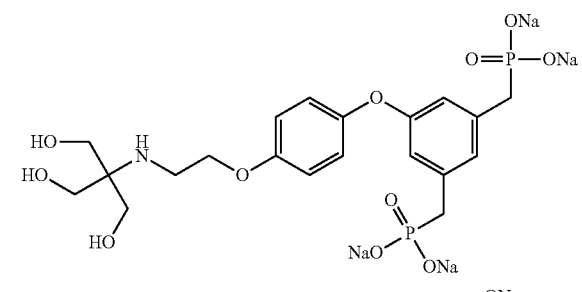
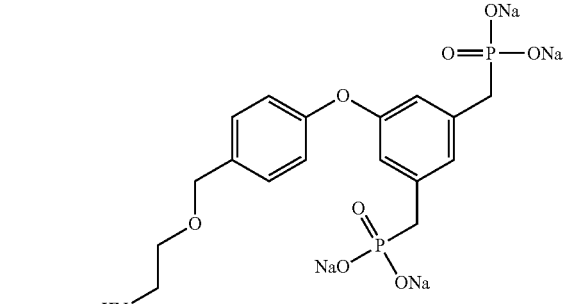
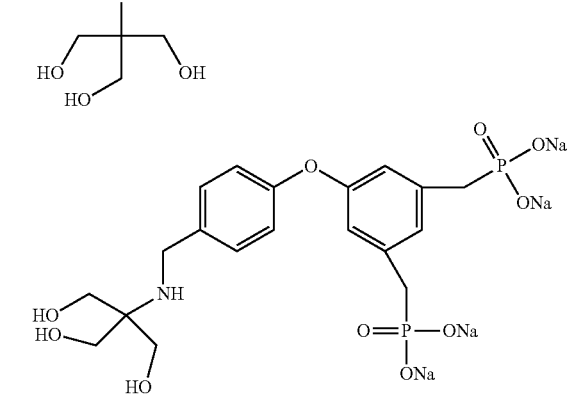
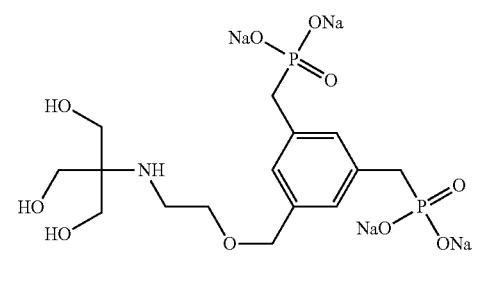

-continued
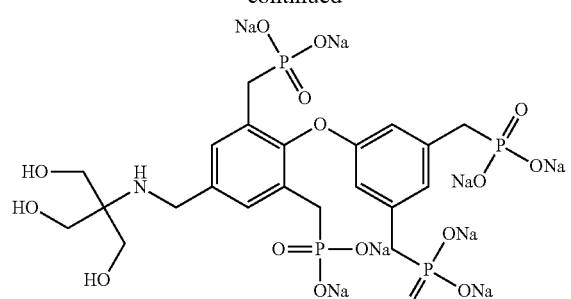
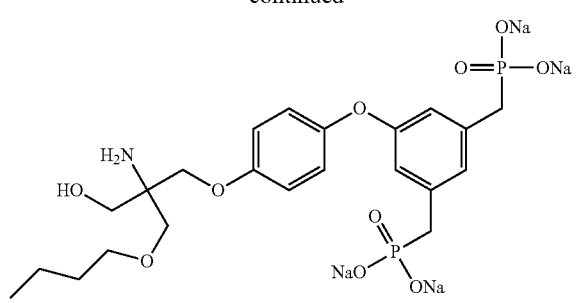
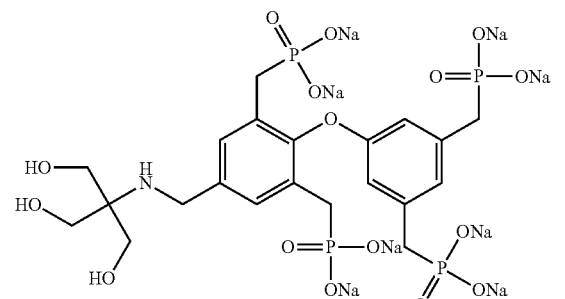
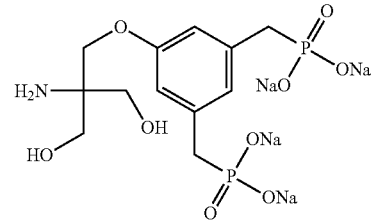
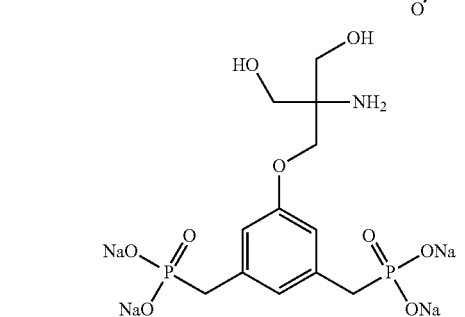
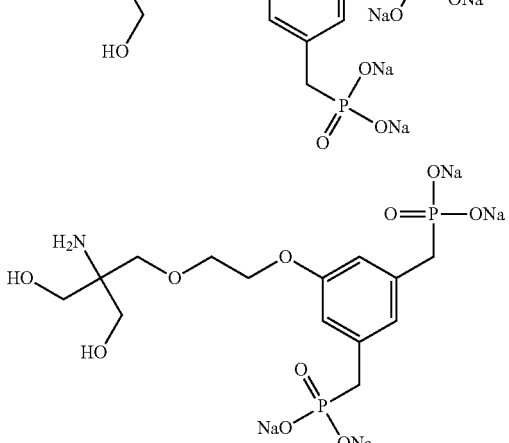
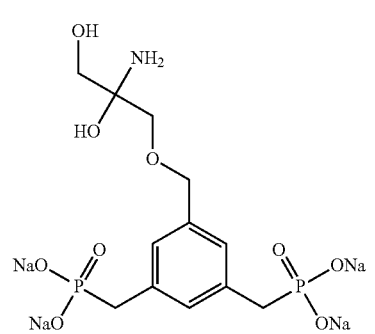
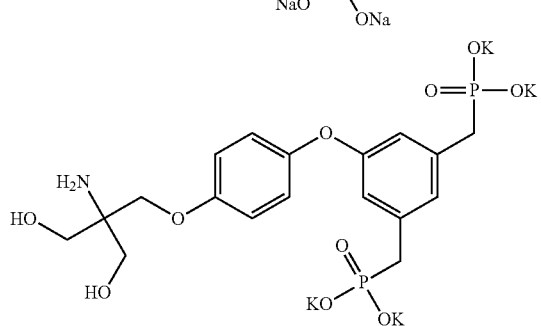
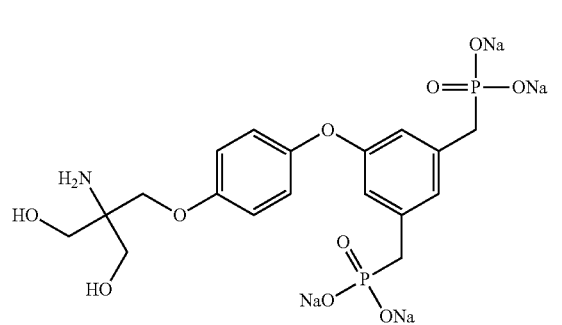
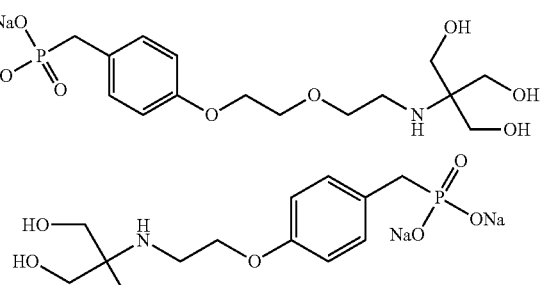

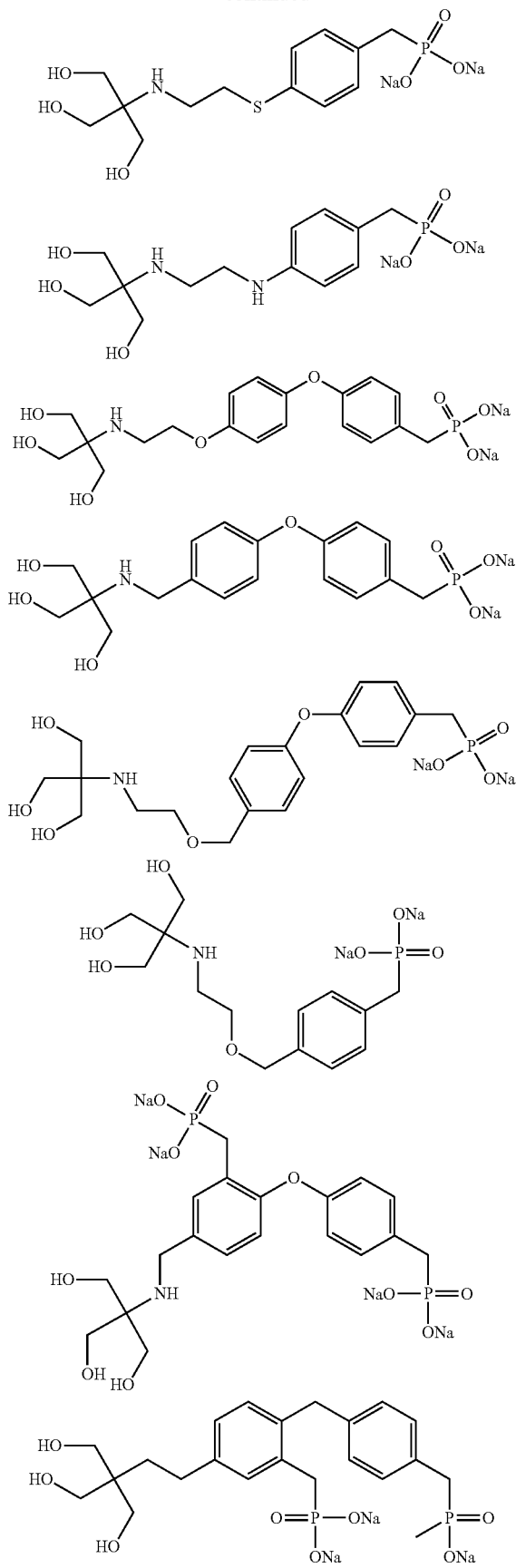
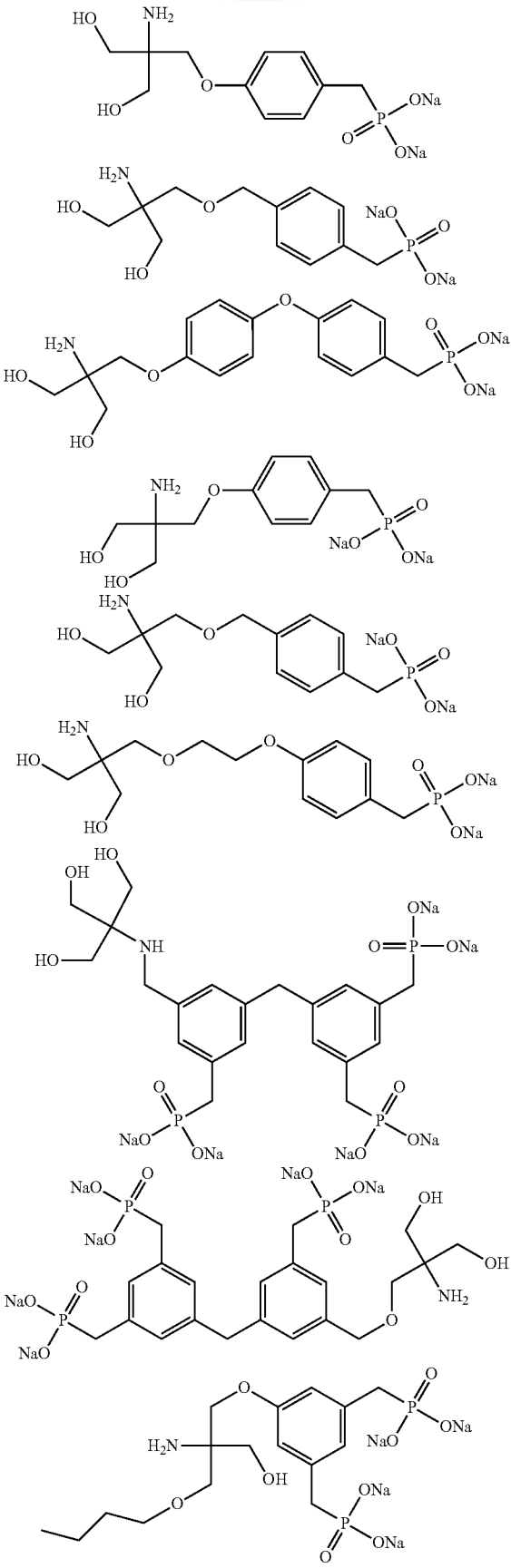

45
-continued
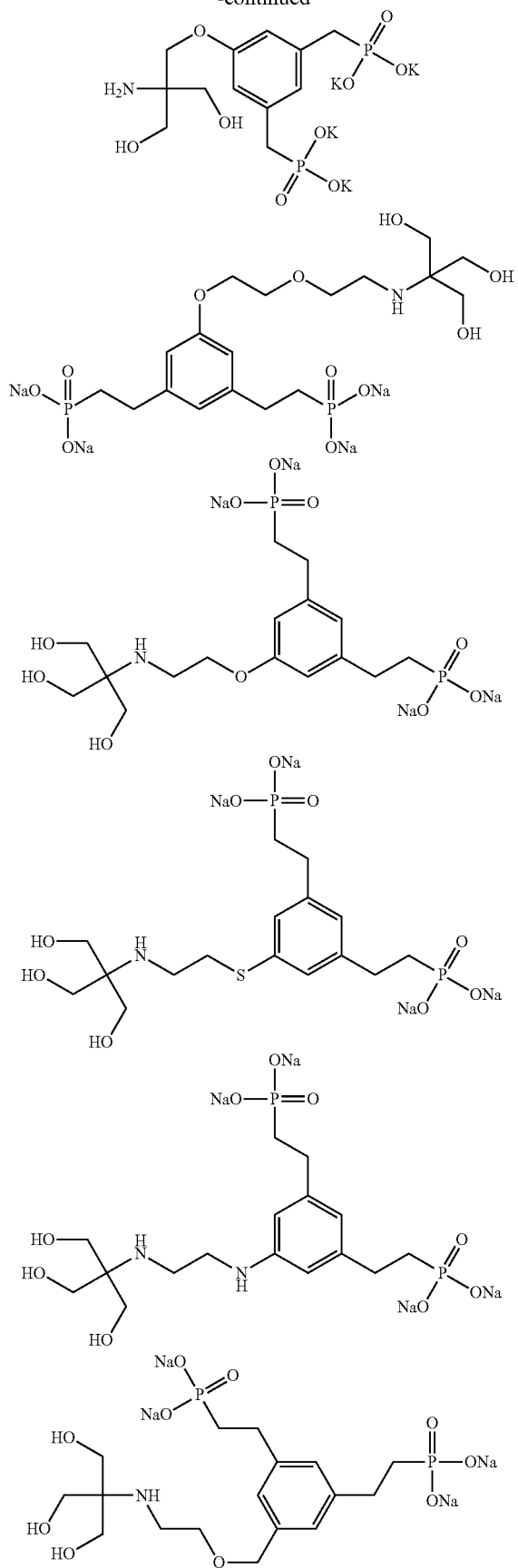
46
-continued
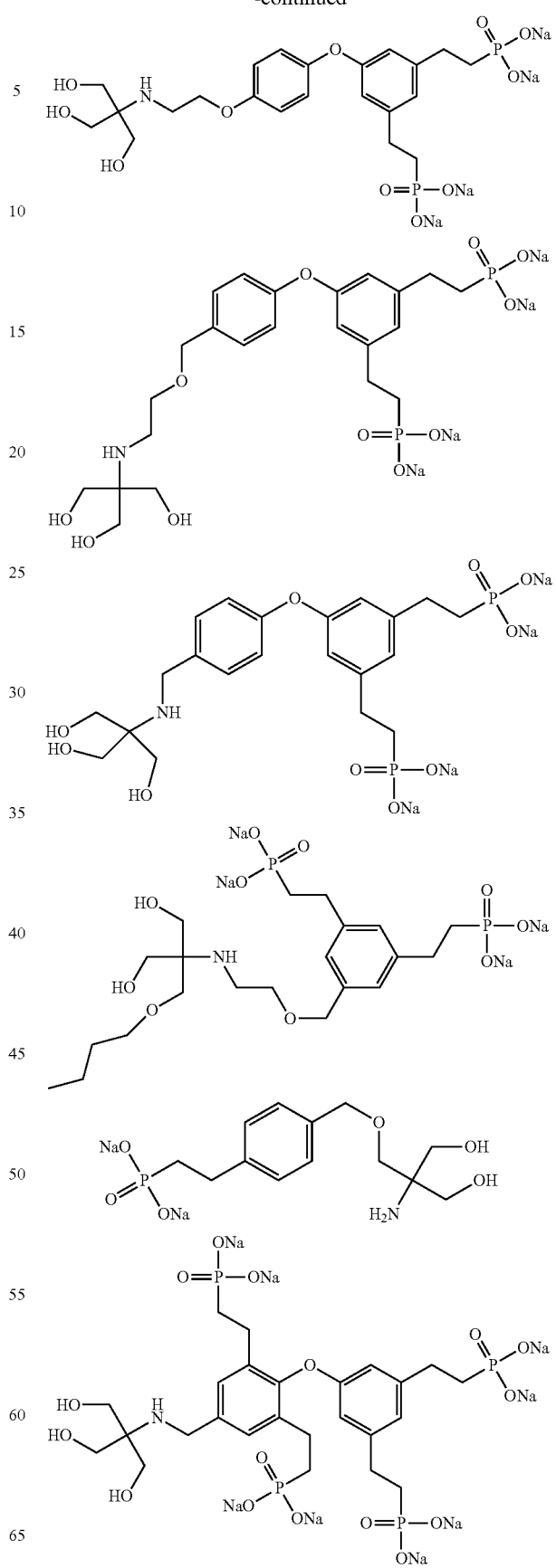

47
-continued
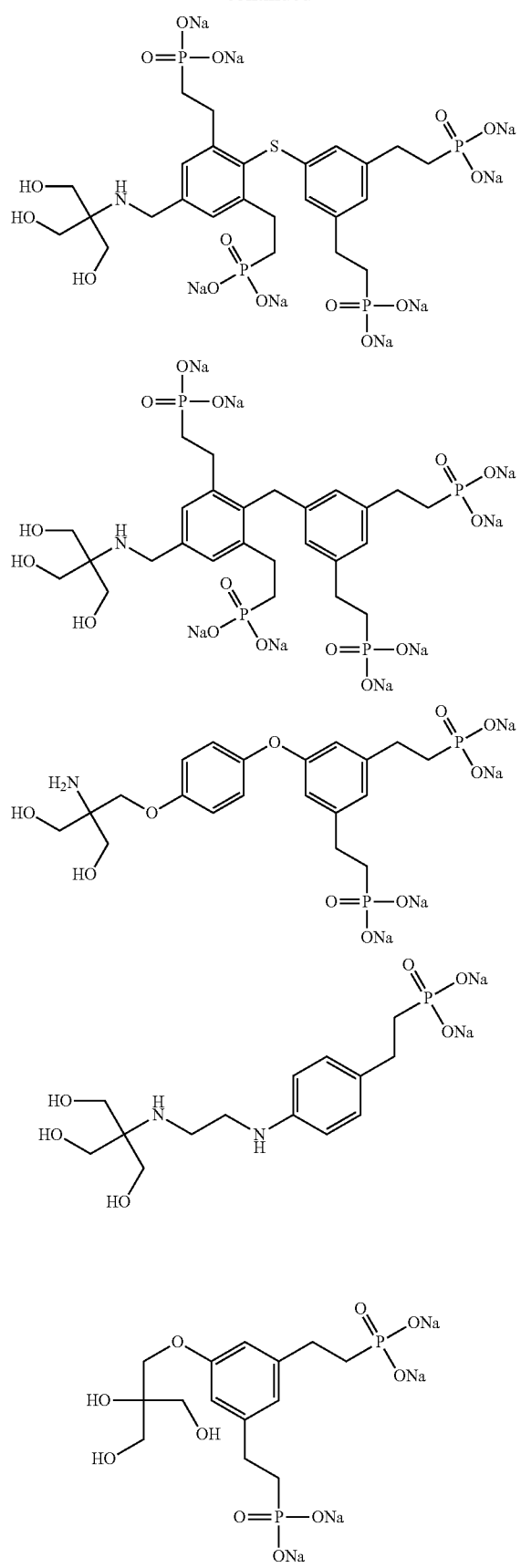
48
-continued
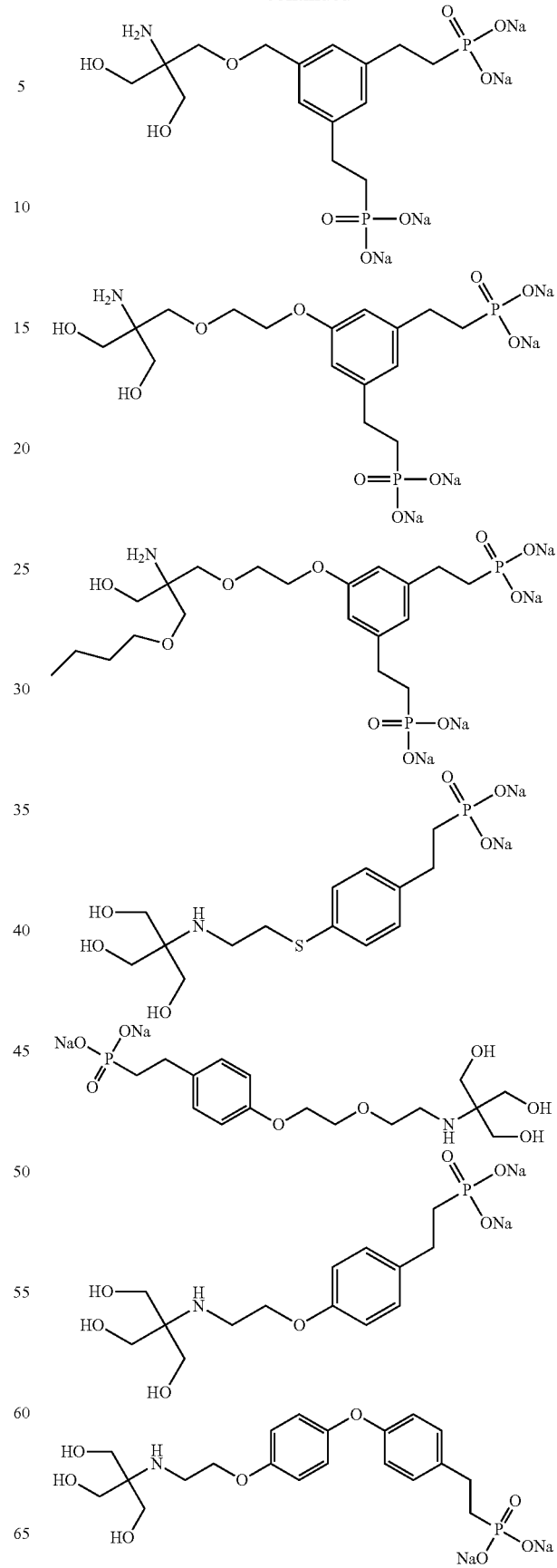

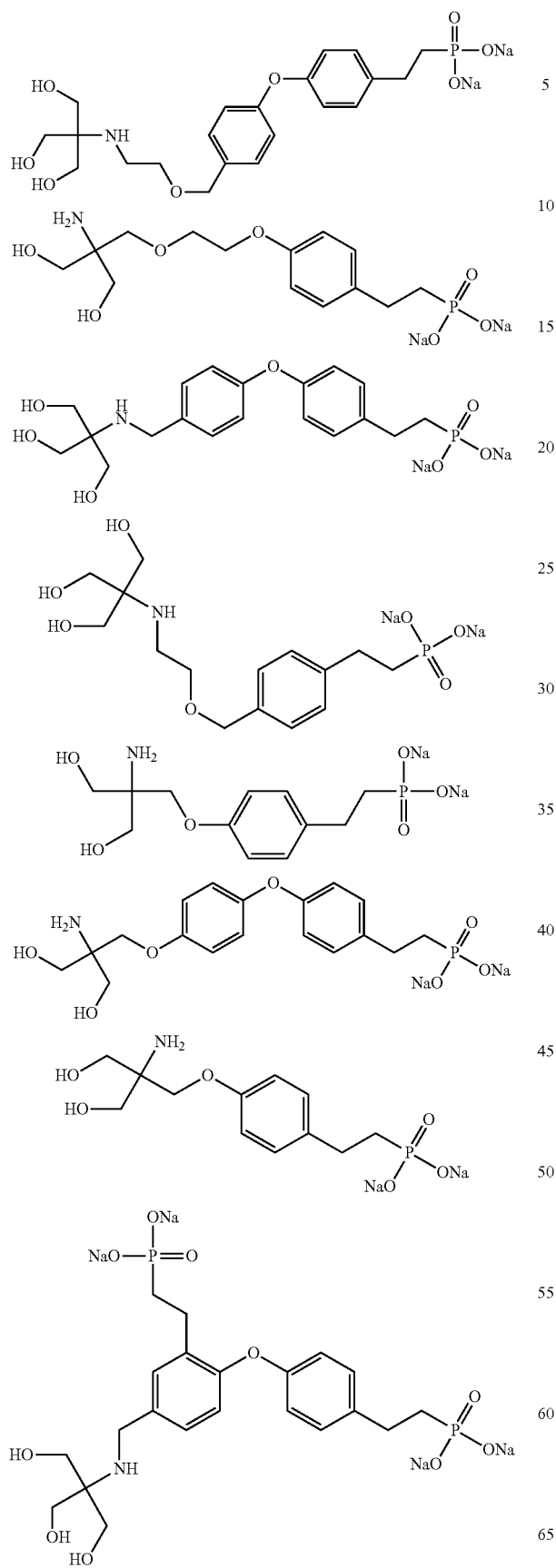
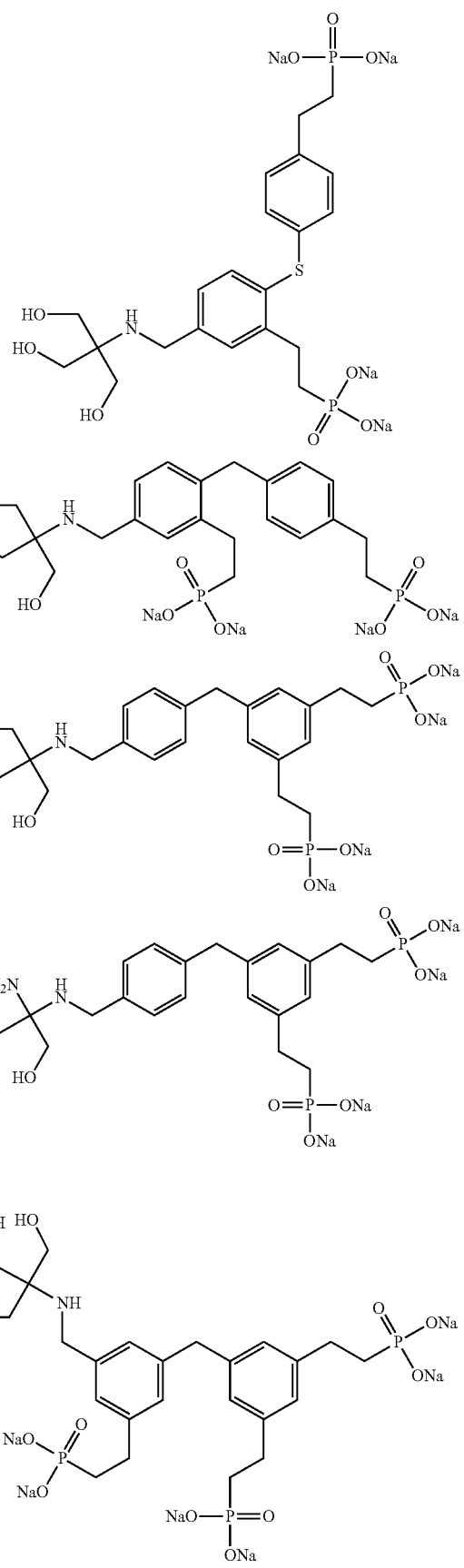

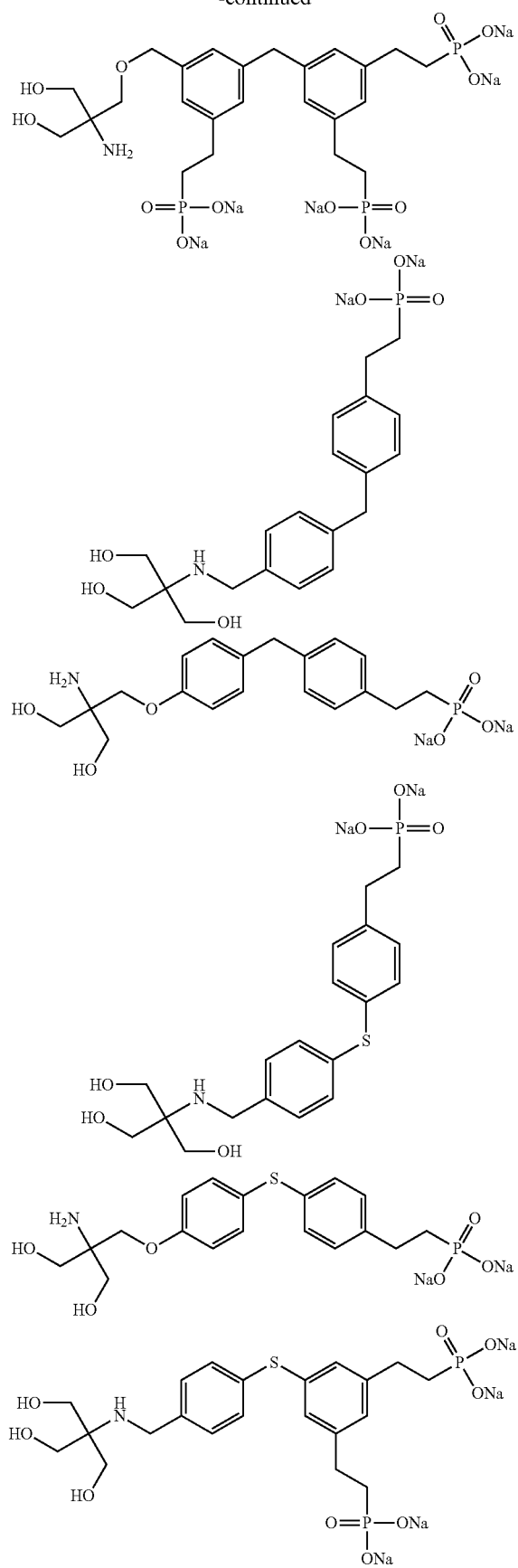
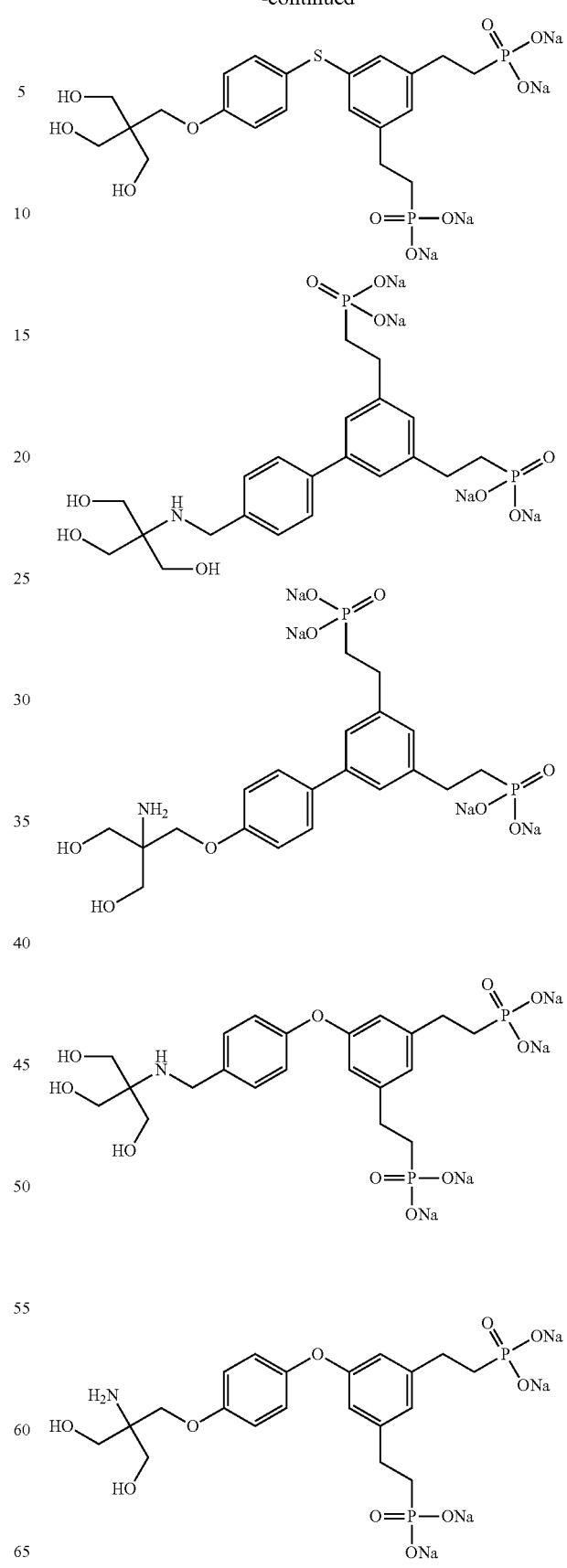

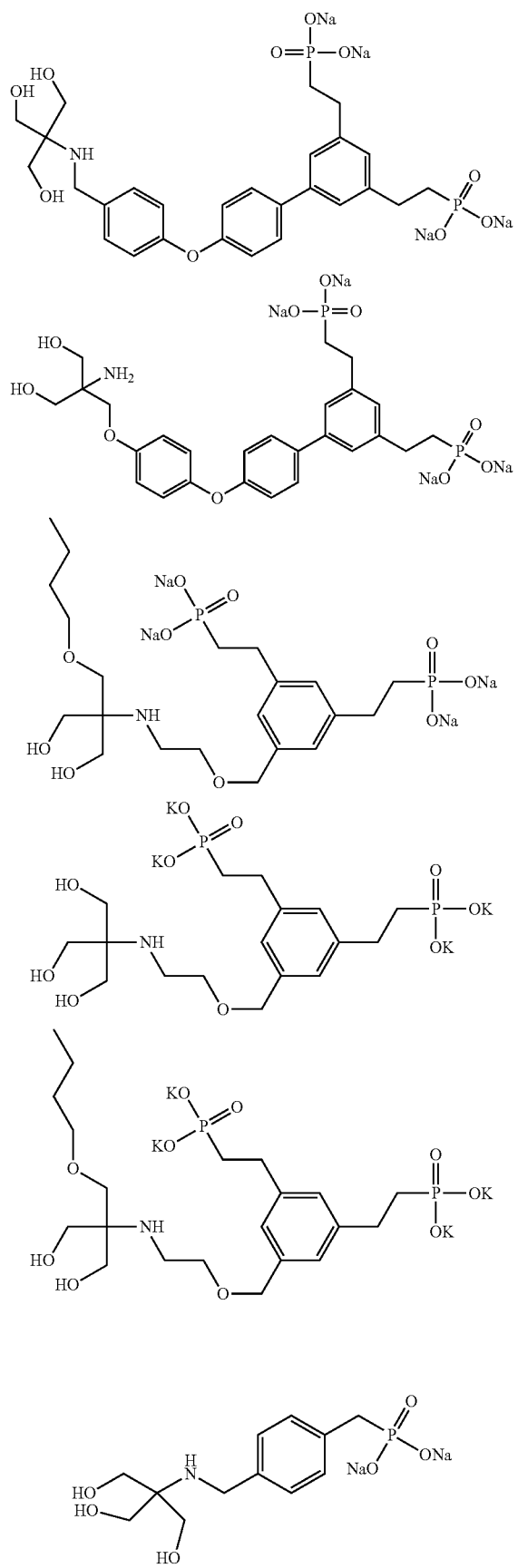
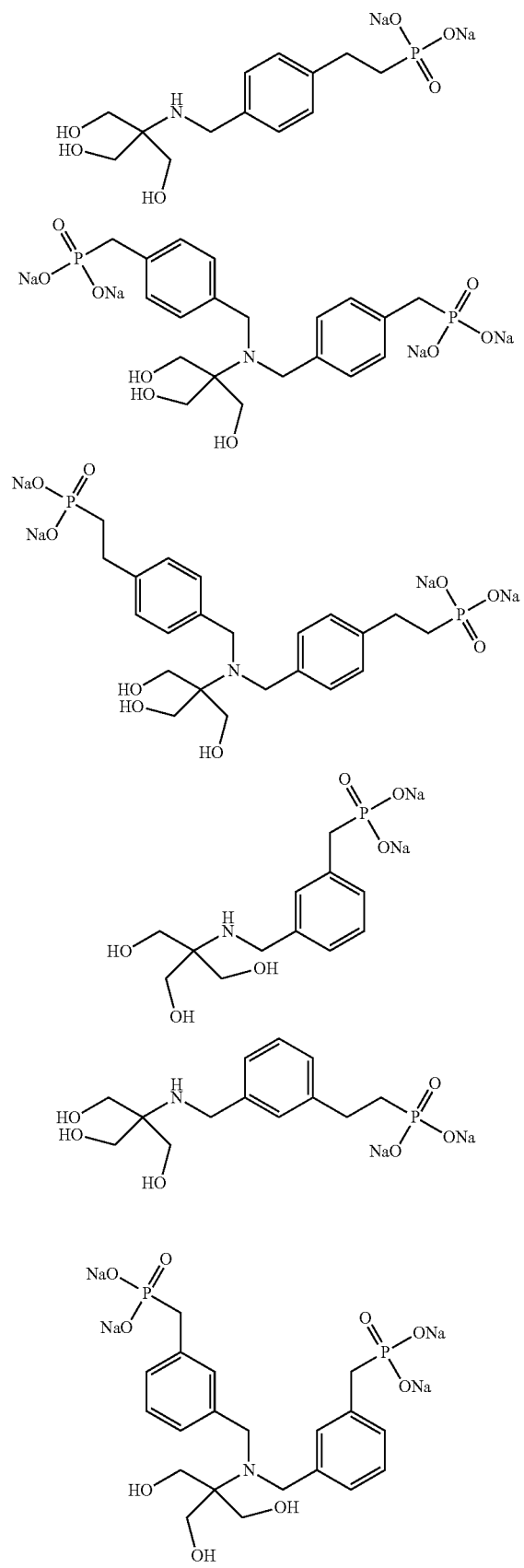

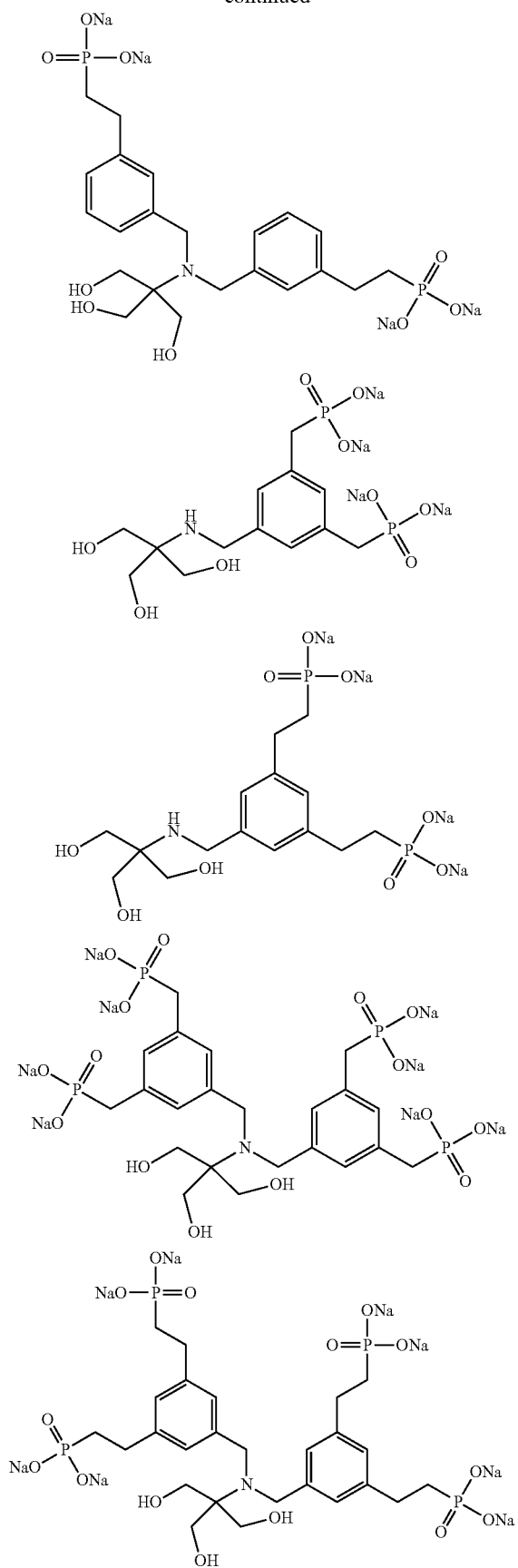
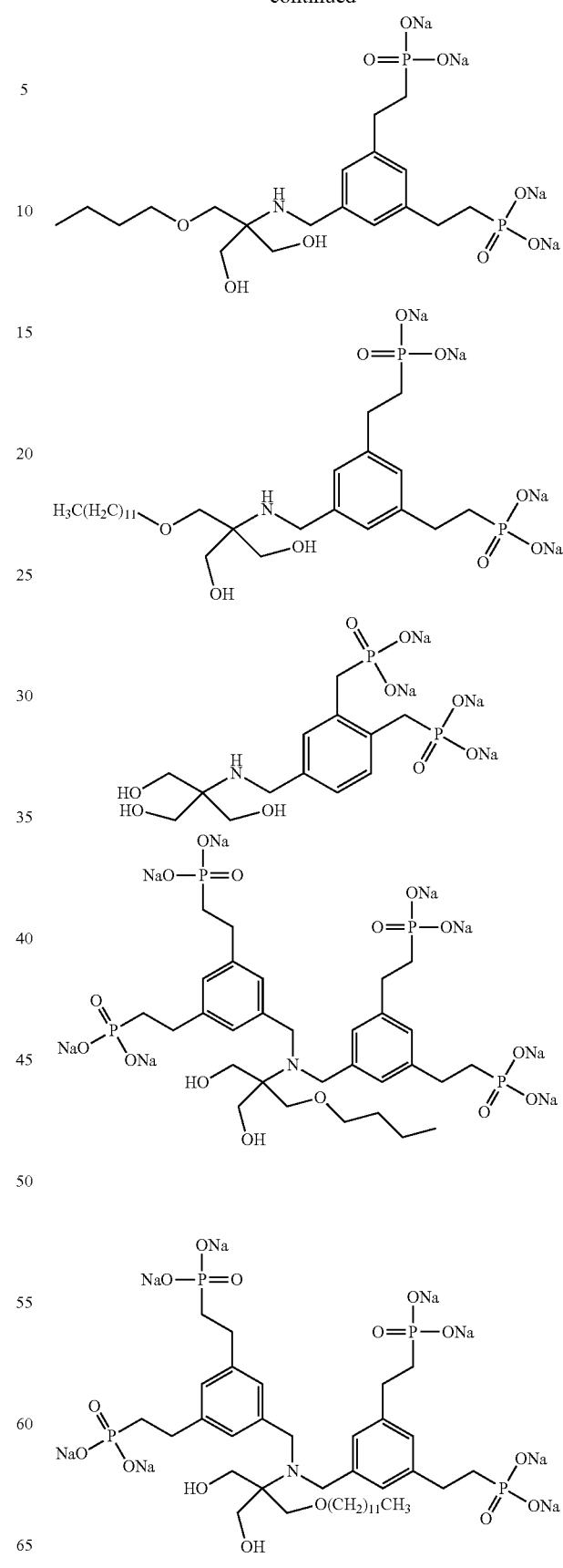

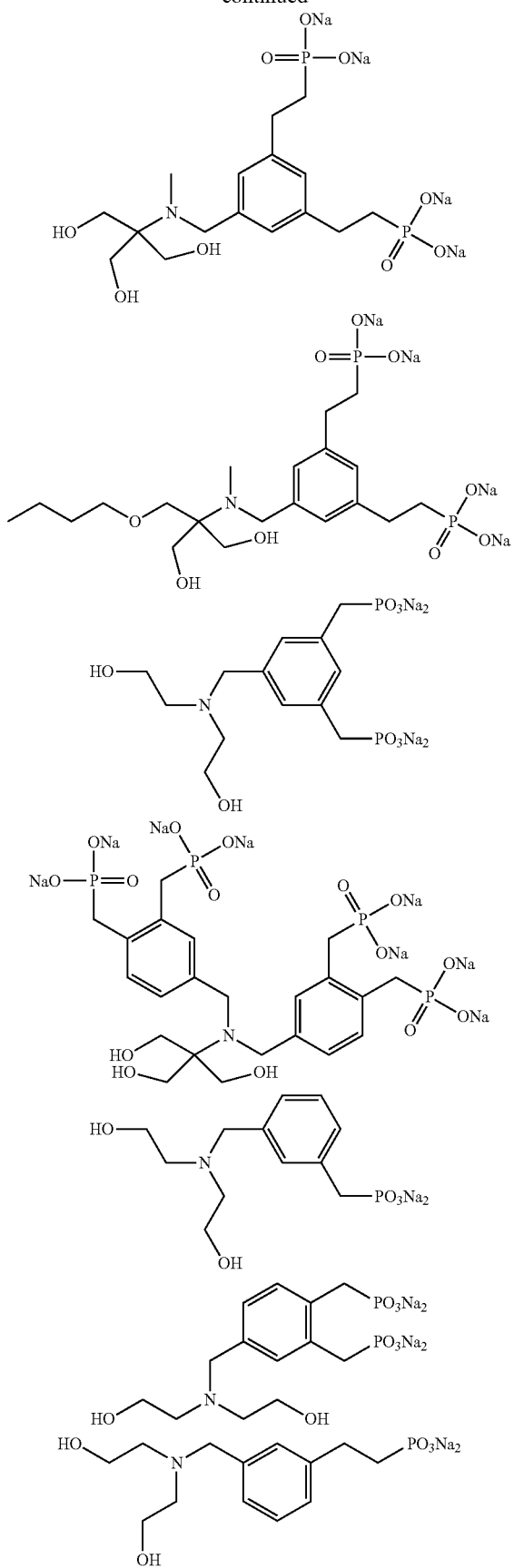
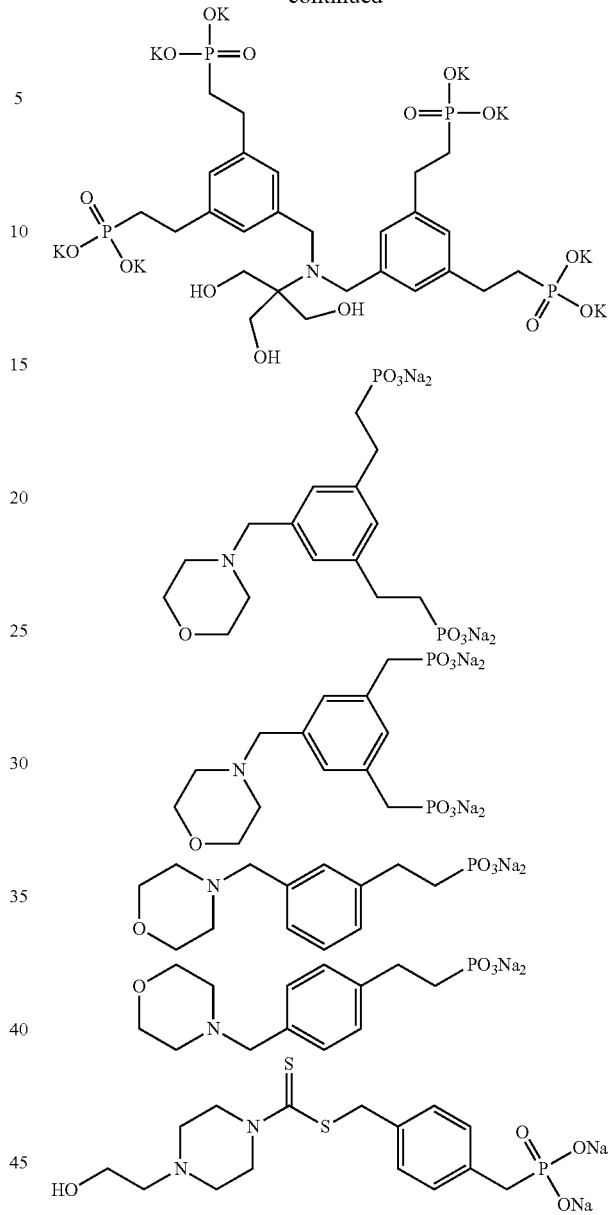

In another aspect, the present invention further provides a pharmaceutical composition, which includes a therapeutically effective amount of the compound shown in the above formula (I), or the tautomer, mesomer, racemate, enantiomer, and diastereoisomer thereof, or the mixture form thereof, or the pharmaceutically acceptable salt thereof, or the prodrug molecule thereof, and further includes one or more pharmaceutically acceptable carriers, diluents, excipients.

The above acceptable carrier is nontoxic and can be used for auxiliary application without adverse effect on the therapeutic effect of the compound. Such carrier can be any commonly available solid excipient, liquid excipient, semi-solid excipient or gas excipient in aerosol composition for those skilled in the art. Solid drug excipients include starch, cellulose, talc, glucose, lactose, sucrose, gelatin, malt, rice, flour, chalk, silica gel, magnesium stearate, sodium stearate, glyceryl stearyl ester, sodium chloride, anhydrous skim milk, etc. Liquid and semi-solid excipients can be selected from glycerin, propylene glycol, water, ethanol and various oils, including the oil originated from petroleum, animal and plant or synthetic oil, such as peanut oil, soybean oil, mineral oil, sesame oil, etc. Preferable liquid carriers, especially those used for injectable solutions, include, water, saline, glucose aqueous solution and glycol. In addition, other adjuvants such as flavoring agent, sweetening agent, etc. can also be added in the composition.

The compound of the present invention can be administrated in the therapeutically effective dose, it can be administrated either orally or systemically (such as transcutaneously, nasal inhalation or suppository) or parenterally (such as intramuscularly, intravenously or subcutaneously). Oral administration is preferred, and it can be adjusted according to the severity of disease.

The actual application amount (i.e., active ingredient) for the compound of the invention depends on multiple factors, such as the severity of disease to be treated, the age and relative health level of the treated subject, the efficacy of the used compound, way and form of administration, and other factors.

Various dosage forms of the medicinal composition of the invention can be prepared in accordance with the conventional methods in the field of pharmacy. For example, the compound can be mixed with one or more carriers, and then it was prepared into the desired dosage form, such as tablets, pills, capsules, semi solid, powder, slow release formulation, solution, suspension, compounding solvent, aerosol, etc.

In another aspect, the present invention further provides use of the compound shown in the formula (I), or the tautomer, mesomer, racemate, enantiomer, and diastereoisomer thereof, or a mixture form thereof, or the pharmaceutically acceptable salt thereof, or the prodrug molecule thereof, or the above-mentioned pharmaceutical composition in preparing drugs for preventing and/or treating the diseases caused or mediated by acidic microenvironment. The diseases include a variety of cancers and a variety of cancer metastasis.

The cancers include breast cancers, cervical cancers, colon cancers, lung cancers, stomach cancers, rectal cancers, pancreatic cancers, brain cancers, skin cancers, oral cancers, prostate cancers, bone cancers, kidney cancers, ovarian cancers, bladder cancers, liver cancers, tumors of the fallopian tube, ovarian tumors, peritoneal tumors, stage IV melanoma, glioma, glioblastoma, hepatocellular carcinoma, mastoid nephroma, head and neck tumors, leukemia, lymphoma, myeloma, non-small cell lung cancers, head and neck cancers, uterine cancers, testicular cancers, fallopian tube cancers, endometrial cancers, vaginal cancers, carcinoma of vulva, rectal cancers, colon cancers, anal cancers, breast cancers, esophageal cancers, small intestine cancers, endocrine system cancers, thyroid cancers, parathyroid cancers, adrenal cancers, urethra cancers, penile cancers, testicular cancers, lymph cancers, transitional cell carcinoma, ureteral cancers, renal cell carcinoma, renal pelvic cancers, Hodgkin's diseases, non-Hodgkin's lymphoma, soft tissue sarcoma, solid tumors in children, lymphocytic lymphoma, central nervous system (CNS) tumors, primary central nervous system lymphomas, tumor angiogenesis, spinal tumors, brainstem glioma, pituitary adenoma, melanoma, Kaposi's sarcoma, epidermoid carcinoma, squamous cell carcinoma, T cell lymphoma, chronic or acute leukemia, and/or combinations of the respective cancers.

In another aspect, the present invention further provides use of the above compound, or the tautomer, mesomer, racemate, enantiomer, and diastereoisomer thereof, or the mixture form thereof, or the pharmaceutically acceptable salt thereof, or the prodrug molecule thereof, or the pharmaceutical composition, in preparing drugs for inhibiting the cancer metastasis.

In another aspect, the present invention further provides use of the above compound, or the tautomer, mesomer, racemate, enantiomer, and diastereoisomer thereof, or the mixture form thereof, or the pharmaceutically acceptable salt thereof, or the prodrug molecule thereof, or the pharmaceutical composition according to claim 7, in preparing drugs for preventing and/or treating the diseases caused by the acidosis.

In another aspect, the present invention further provides use of the above compound, or the tautomer, mesomer, racemate, enantiomer, and diastereoisomer thereof, or the mixture form thereof, or the pharmaceutically acceptable salt thereof, or the prodrug molecule thereof, in combination with at least one additional anticancer drug, in preparing drugs for treating cancers or inhibiting cancer metastasis.

Tumor microenvironment is a target with obvious effect for anti-tumor drugs and inhibiting cancer metastasis, whereas the compound of the invention has significant activity in inhibiting cancer proliferation and metastasis, experiments have confirmed that these compounds have inhibitory effect on the proliferation of various cancer cells, and thus the compound of the invention is applicable for treating various cancers and cancer metastasis. Especially, it has better therapeutic effects on liver cancer, kidney cancer, prostate cancer, lung cancer, gastric cancer, ovarian cancer, colon cancer, pancreatic cancer, etc., and its metastasis. The treatment of the cancer metastasis cause by orthotopic tumor is very obvious and therapeutically effective.

The phosphate derivatives of the present invention, playing the role of tumor acidic microenvironment modulator, combining with clinical drugs, can effectively inhibit cancer proliferation and metastasis, and are therapeutically effective to a variety of cancers, especially liver cancer, kidney cancer, prostate cancer, lung cancer, gastric cancer, ovarian cancer, colon cancer, pancreatic cancer, etc., and its metastasis, and very minor side effect can be observed in all treatment, has a very broad application prospect.

BRIEF DESCRIPTION OF THE DRAWINGS

The present invention will be further explained in details by combining with the drawings and embodiments.

DETAILED DESCRIPTION OF THE INVENTION

Example 1 Synthesis of Compound 1

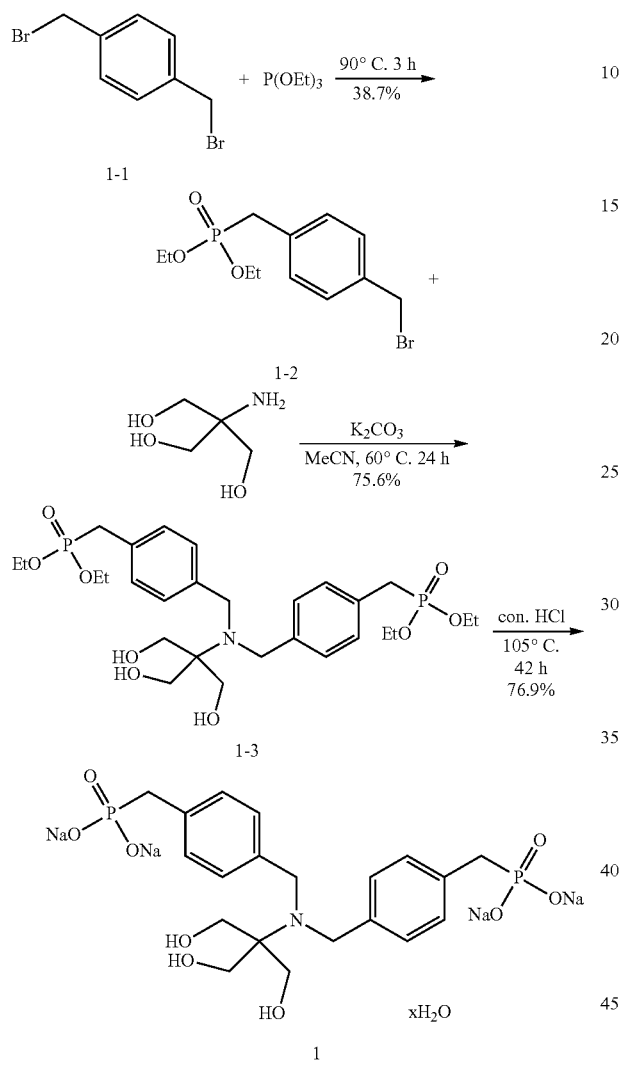

Figure 1:
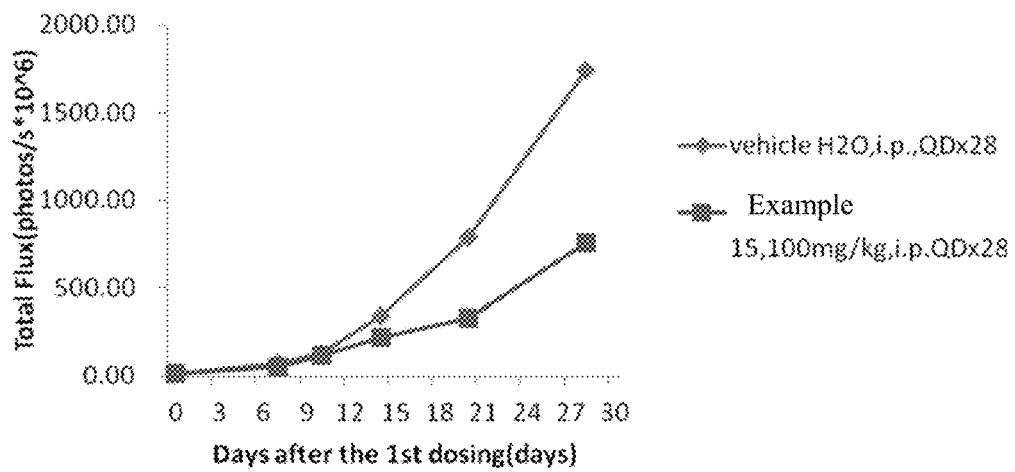
FIG. 1 is the fitted for the inhabitation on the proliferation of orthotopic xenograft HCC78 Hep3B2.1-7-Luc in Example 8 compound of the invention via method of Example 25 of the present invention.

Step (1): To a 250 mL flask was added 1,4-bis(bromomethyl)-benzene 53.0 g (0.201 mol, triethyl phosphite 33.4 g (0.201 mol). The flask was heat up in an oil bath. The mixture was stirred for 3 hrs under 90° C. After removal of heating system, to the cool mixture was added 50 mL dichloromethane. The resulted mixture was kept stirring for 10 minutes, and was added 100 mL petroleum ether, and was stirred overnight. Then the suspension was filtered, the residue was washed with 100 mL solvent mixture of $CH_2Cl_2$ and petroleum ether (v/v, 1:10). The filtrate was collected and combined, concentrated to give a thick liquid which was purified by column chromatography to provide compound 1-2 with 25.0 g, 38.7% of yield; $Cl_2H_{18}BrO_3P$, MS (ES+) m/z: 321.0 (M+H)$^+$.

Step (2): To a 500 mL flask was added, compound 1-2 with 25.0 g (77.9 mmol), Tris 4.29 g (35.4 mmol), anhydrous K2C03 12.2 g (88.5 mmol), 150 mL acetonitrile, and 150 mL acetonitrile. The mixture was stirred over 24 hrs under 60° C. After removal of heating system, to the cool mixture was added 50 mL dichloromethane. The resulted mixture was kept stirring for 10 minutes, and was added 100 mL $CH_2Cl_2$ twice, and was stirred overnight. Then the suspension was filtered, the residue was washed with 100 mL twice. The filtrate was collected and combined, concentrated to give a thick liquid which was purified by column chromatography to provide compound 1-3 with 16.1 g, 75.6% yield; $C_{28}H_{45}NO_9P_2$, MS (ES+) m/z: 602.2 (M+H)$^+$.

Step (3): To a 500 mL flask was added, compound 1-3 with 16.1 g (26.8 mmol), 150 mL aqueous concentrate HCl. The reaction mixture was heated to 105° C. for 42 hrs, and keep stirring. After removal of heating system, to the cool mixture was concentrated to resulted a pale solid, which was purified by resin column. The resulted solid was dissolved in water, and was added 2N NaOH. After concentration the solid was recrystallized by ethanol to give a while solid, compound 1, 16.0 g with 76.9% yield; 1H NMR (500 MHz, D2O) δ 7.15 (s, 4H), 3.90 (s, 2H), 3.61 (s, 3H), 2.72 (d, J=19.8 Hz, 2H); $C_{20}H_{25}NNa_4O_9P_2 \cdot xH_2O$, MS (ES+) m/z: 490.2 (M+H)$^+$.

Example 2 Synthesis of compound 2

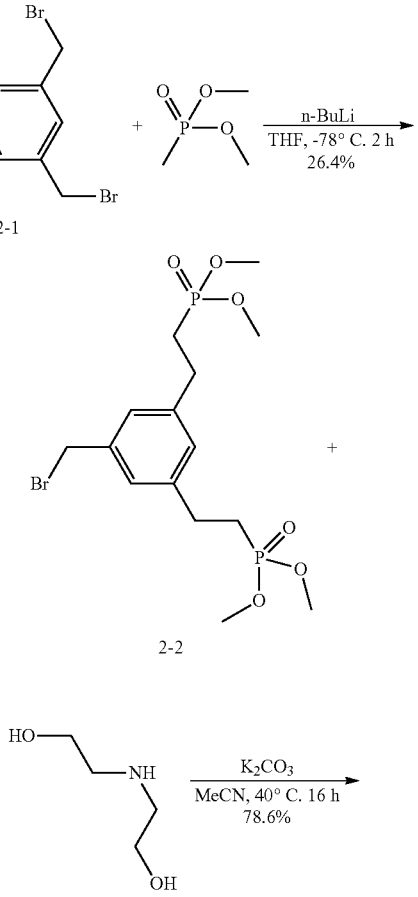

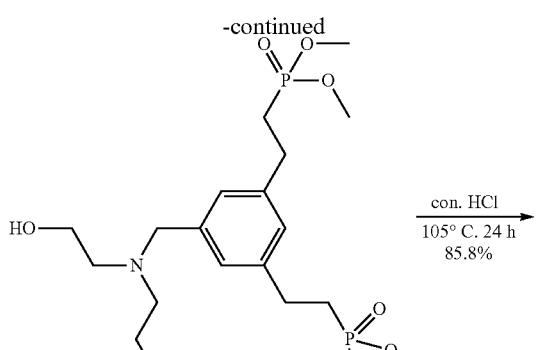

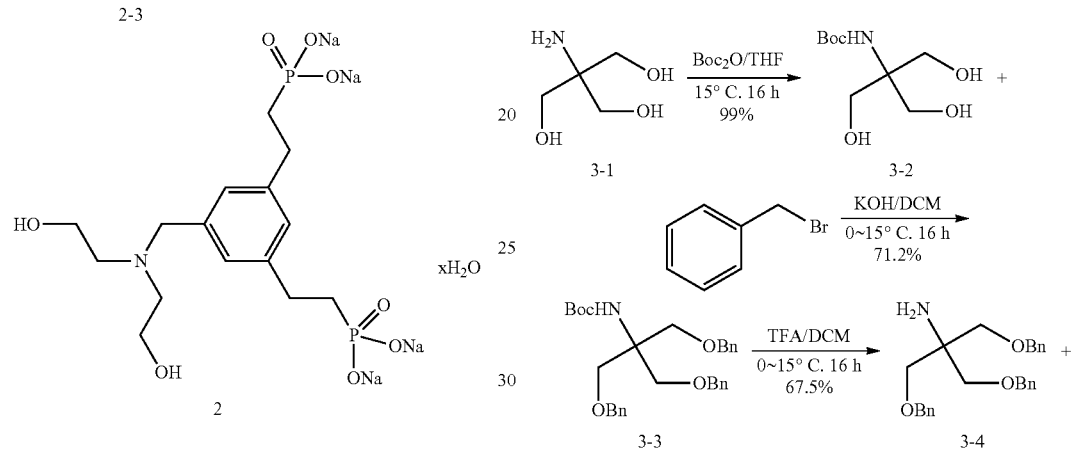

Step (1): To a 2000 mL three neck flask, was added 400 mL of anhydrate THF, dimethyl-methylphosphate 33.4 g (0.201 mol) 24.8 g (0.200 mol). The flask was cooled down to −78° C. via a dry ice-acetone bath, and was dropwise added 88 mL Butyl lithium in hexane (0.22 mol, 2.5 M) in 50 minutes. After keep stirring for another hour at −78° C., 1,3,5-tris(bromomethyl)benzene 35.7 g (0.100 mol) in 200 mL of THF was added in 30 minutes. The mixture was kept stirring for 1 hr. LCMS showed the major product is desired. The reaction mixture was quenched by monopotassium phosphate (1 M, 100 mL), and was warmed up to room temperature. The mixture of liquid was separated by filtration funnel. The aqueous phase was washed by 50 mL of solvent mixture chloroform and isoproplyl (3:1) with four times. The organic phase was combined and added $Na_2SO_4$, filtered and concentrated. The residue was purified to give compound 2-2 11.7 g, with 26.4% yield, $C_{15}H_{25}BrO_6P_2$, MS (ES+) m/z: 443.0 $(M+H)^+$.

Step (2): To a 50 mL flask, was added compound 2-2 290 mg (0.653 mmol), diethanol amine 137 mg (1.31 mmol), and $K_2CO_3$ 90 mg (0.653 mmol), and 10 mL of acetonitrile. The mixture was stirring for 16 hrs at 40° C. After cooled down, the mixture was filtrated. The filter residue was washed with 10 mL dichloromethane twice. The combined liquid was concentrated to give a viscous liquid, which was purified with flash column chromatography to give compound 2-3 240 mg with 78.6% yield; $C_{19}H_{35}NO_8P_2$, MS (ES+) m/z: 468.2 $(M+H)^+$.

Step (3): To a 50 mL flask, was added compound 2-3 240 mg (0.513 mmol), and 5 mL concentrated HCl. The mixture was heat up to reflux at 105° C. over 24 hrs under an oil bath. The mixture was cooled down and concentrated to give a solid. The solid was purified by resin column. The eluent concentrated and dried by lyophilizer. The solid was dissolved in water, and was added 2 N NaOH solution, concentration. And the solid was crystalized with ethanol to give compound 2 250 mg with 85.8% yield; 1H NMR (500 MHz, D2O) δ 7.08 (s, 1H), 7.01 (s, 2H), 3.66 (s, 2H), 3.59 (t, J=6.2 Hz, 4H), 2.70-2.53 (m, 8H), 1.60-1.43 (m, 4H); $C_{15}H_{23}NNa_4O_8P_2 \cdot xH_2O$, MS (ES+) m/z: 412.1 $(M+H)^+$.

Example 3: Synthesis of Compound 3

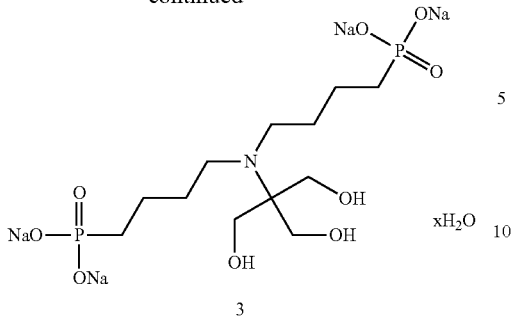

Step (1): To a 500 mg flask, was added tris amine 12.1 g (0.100 mol), 100 mL THF, and added dropwise Boc$_2$O 21.8 g (0.100 mol) in 80 mL THF at r.t within 30 min. The mixture was kept stirring for 16 hrs, and concentrated to give compound 3-2 22.1 g with 99% yield as a viscous liquid, which was directly used for next step; C$_9$H$_{19}$NO$_5$, MS (ES+) m/z: 244.0 (M+Na)$^+$.

Step (2): To a 1000 mL three-neck flask, was added compound 3-2 22.1 g (0.100 mol), and 300 mL dichloromethane. The mixture was cooled to 0° C. with ice-water bath. And powder of KOH 18.6 g (0.32 mol), and benzyl bromide 53.0 g (0.31 mol) was added. The mixture was kept stirring at 0-15° C. for 16 hrs. After filtration, the organic phase was washed with water 3×200 mL, and dried over Na$_2$SO$_4$, and was concentration. The resulted solid was purified by silico gel column chromatography to give a viscous liquid Compound 3-3 35.0 g with 71.2% yield; C$_{30}$H$_{37}$NO$_5$, MS (ES+) m/z: 514.3 (M+Na)$^+$.

Step (3): To a 500 mL three-neck flask, was added compound 3-3 22.1 g (0.100 mol), 26.0 g (52.9 mmol), 120 mL dichloromethane. The mixture was cooled to 0° C. with ice-water bath. And 40 mL trifloroacetic acid was added. The mixture was kept stirring at 0-15° C. for 16 hrs. The mixture was concentrated to give a residue. The residue was washed with petroleum ether, and was added 200 mL water, and added 5% aq. Sodiumbicarbonate to make pH 9. The mixture then was extracted with dichloromethane 2×200 mL, then washed with 200 mL water, 200 mL brine, and was dried over Na$_2$SO$_4$. The solution was concentrated to give compound 3-4 14.0 g with 67.5% yield as a viscous liquid; C$_{30}$H$_{37}$NO$_5$, MS (ES+) m/z: 392.2 (M+H)$^+$.

Step (4): To a 100 mg flask, was added compound 3-4 782 mg (2.00 mmol), 3-5 915 mg (4.00 mmol), K$_2$CO$_3$ 552 mg (4.0 mmol), and 20 mL acetonitrile. The mixture was kept stirring for 30 hrs at 80 degree. The mixture was filtrated and concentrated to yield crude product, which was further purified by silico gel flash chromatography to give desired Compound 3-7 608 mg with 39.2% yield; C$_{41}$H$_{63}$NO$_9$P, MS (ES+) m/z: 776.4 (M+H)$^+$; and compound 3-6 249 mg with 21.3% yield; C$_{30}$H$_{37}$NO$_5$, MS (ES+) m/z: 584.3 (M+H)$^+$.

Step (5): To a 100 mL flask, was added compound 3-7 608 mg (0.784 mmol), and 10 mL concentrated HCl. The mixture was heat up to reflux at 105° C. over 18 hrs under an oil bath. The mixture was cooled down and concentrated to give a solid. The solid was purified by resin column. The eluent concentrated and dried by lyophilizer. The solid was dissolved in water, and was added 2N NaOH solution, concentration. And the solid was crystalized with ethanol to give compound 3 279 mg with 62.3% yield as a while solid; C$_{12}$H$_{25}$NNa$_4$O$_9$P$_2$·xH$_2$O, MS (ES+) m/z: 394.1 (M+H)$^+$. 250 mg with 85.8% yield; 1H NMR (500 MHz, D2O) δ 7.08 (s, 1H), 7.01 (s, 2H), 3.66 (s, 2H), 3.59 (t, J=6.2 Hz, 4H), 2.70-2.53 (m, 8H), 1.60-1.43 (m, 4H); C$_{15}$H$_{23}$NNa$_4$O$_8$P$_2$·xH$_2$O, MS (ES+) m/z: 412.1 (M+H)$^+$.

Example 4: Synthesis of Compound 4

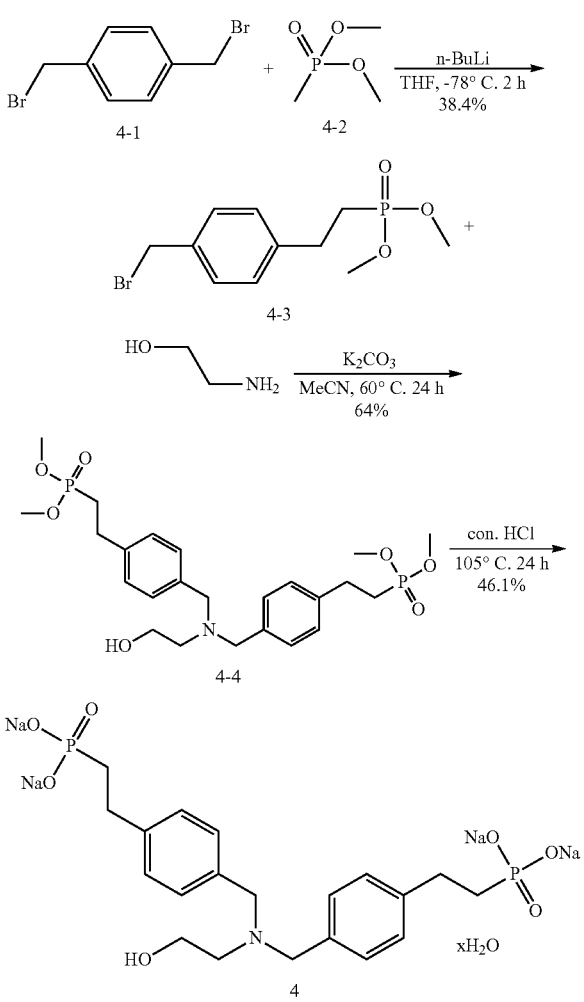

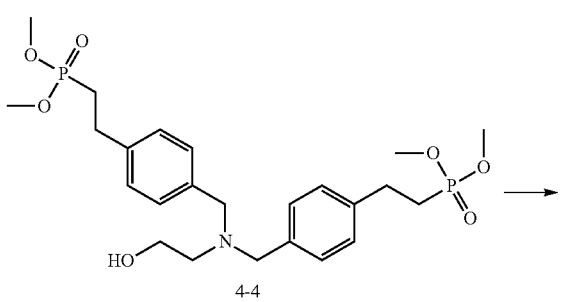

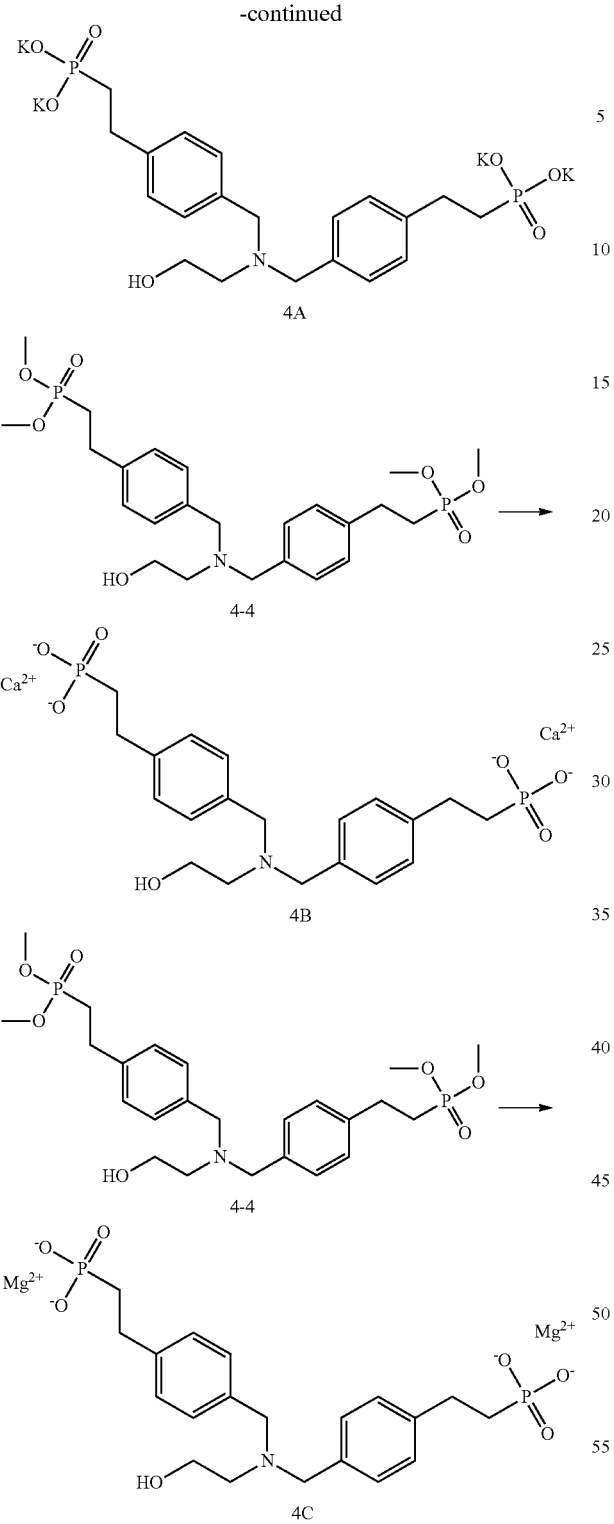

Step (1): To a 1000 mL three-neck flask, was added 400 mL of anhydrate THF, dimethyl-methylphosphate (12.4 g, 100 mmol). The flask was cooled down to −78° C. via a dry ice-acetone bath, and was dropwise added 40 mL butyl lithium in hexane (100 mmol, 2.5M) in 30 minutes. After keep stirring for another hour at −78° C., 1,4-di (bromomethyl) benzene (26.4 g, 100 mmol) in 200 mL of THF was added in 30 minutes. The mixture was kept stirring for 1 hr. LCMS showed the major product is desired. The reaction mixture was quenched by monopotassium phosphate (1M, 100 mL), and was warmed up to room temperature. The mixture of liquid was separated by filtration funnel. The aqueous phase was washed by 50 mL of solvent mixture chloroform and isoproplyl (3:1) with four times. The organic phase was combined and added $Na_2SO_4$, filtered and concentrated. The residue was purified to give compound 4-3 11.8 g, with 38.4% yield; $C_{11}H_{16}BrO_3P$, MS (ES+) m/z: 307.0 (M+H)$^+$.

Step (2): To a 50 mL flask was added, compound 4-3 with 675 mg (2.2 mmol), ethanol amine 61 mg (1.0 mmol), $K_2CO_3$ (304 mg, 2.2 mmol) and 10 mL acetonitrile. The mixture was stirred over 24 hrs under 60° C. After removal of heating system, to the cool mixture was added 50 mL dichloromethane. The resulted mixture was kept stirring for 10 minutes, and was added 10 mL CH2Cl2 twice, and was stirred overnight. Then the suspension was filtered, the residue was washed with 10 mL twice. The filtrate was collected and combined, concentrated to give a thick liquid which was purified by column chromatography to provide compound 4-4 with 330 mg with 64.0% yield as a colorless liquid: $C_{24}H_{37}NO_7P_2$, MS (ES+) m/z: 514.2 (M+H)$^+$.

Step (3): To a 50 mL flask was added, compound 4-4 with 32 8 mg (0.638 mmol), 10 mL aqueous concentrate HCl. The reaction mixture was heated to 105° C. for 24 hrs, and keep stirring. After removal of heating system, to the cool mixture was concentrated to resulted a pale solid, which was purified by resin column. The resulted solid was dissolved in water, and was added 2N NaOH. After concentration the solid was recrystallized by ethanol to give a while solid, compound 4, 200 mg, 46.1%; $C_{20}H_{25}NNa_4O_7P_2 \cdot xH_2O$, MS (ES+) m/z: 458.1 (M+H)$^+$.

Step (4): To a 50 mL flask was added, compound 4-4 with 328 mg (0.638 mmol), 10 mL aqueous concentrate HCl. The reaction mixture was heated to 105° C. for 24 hrs, and keep stirring. After removal of heating system, to the cool mixture was concentrated to resulted a pale solid, which was purified by resin column. The resulted solid was dissolved in water, and was added 2N KOH. After concentration the solid was recrystallized by ethanol to give a while solid, compound 4A, 160 mg.

Step (5): To a 50 mL flask was added, compound 4-4 with 328 mg (0.638 mmol), 10 mL aqueous concentrate HCl. The reaction mixture was heated to 105° C. for 24 hrs, and keep stirring. After removal of heating system, to the cool mixture was concentrated to resulted a pale solid, which was purified by resin column. The resulted solid was dissolved in water, and was added 2 equivalent of $Ca(OH)_2$. After concentration the solid was recrystallized by ethanol to give a while solid, compound 4B, 100 mg.

Step (6): To a 50 mL flask was added, compound 4-4 with 328 mg (0.638 mmol), 10 mL aqueous concentrate HCl. The reaction mixture was heated to 105° C. for 24 hrs, and keep stirring. After removal of heating system, to the cool mixture was concentrated to resulted a pale solid, which was purified by resin column. The resulted solid was dissolved in water, and was added 2 equivalent of $Mg(OH)_2$. After concentration the solid was recrystallized by ethanol to give a while solid, compound 4C, 80 mg.

Example 5: Synthesis of Compound 5

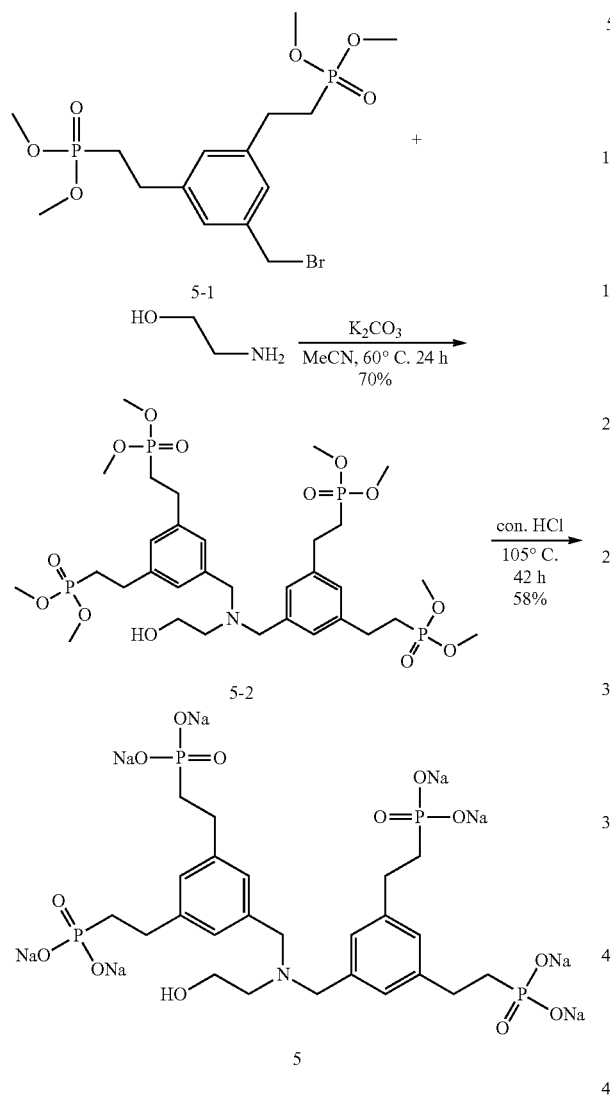

Step (1): To a 50 mL flask was added, compound 5-1 with 972 mg (2.2 mmol), ethanol amine 61 mg (1.0 mmol), K$_2$CO$_3$ (304 mg, 2.2 mmol), and 20 mL acetonitrile. The mixture was stirred over 24 hrs under 60° C. After removal of heating system, to the cool mixture was added 50 mL dichloromethane. The resulted mixture was kept stirring for 10 minutes, and was added 20 mL CH$_2$Cl$_2$ twice, and was stirred overnight. Then the suspension was filtered, the residue was washed with 20 mL twice. The filtrate was collected and combined, concentrated to give a thick liquid which was purified by column chromatography to provide compound 5-2 with 550 mg with 70% yield, as a colorless liquid: C$_{32}$H$_{55}$NO$_{13}$P$_4$, MS (ES+) m/z: 786.3 (M+H)$^+$.

Step (2): To a 50 mL flask was added, compound 4-4 with 550 mg (0.7 mmol), 10 mL aqueous concentrate HCl. The reaction mixture was heated to 105° C. for 42 hrs, and was kept stirring. After the removal of heating system, the cool mixture was concentrated to result a pale solid, which was purified by resin column. The resulted solid was dissolved in water, and was added 2N NaOH. After concentration the solid was recrystallized by ethanol to give a while solid, compound 5, 390 mg, 58% yield: C$_{24}$H$_{31}$NNa$_8$O$_{13}$P$_4$·xH$_2$O, MS (ES+) m/z: 674.1 (M+H)$^+$.

Example 6: Synthesis of Compound 6

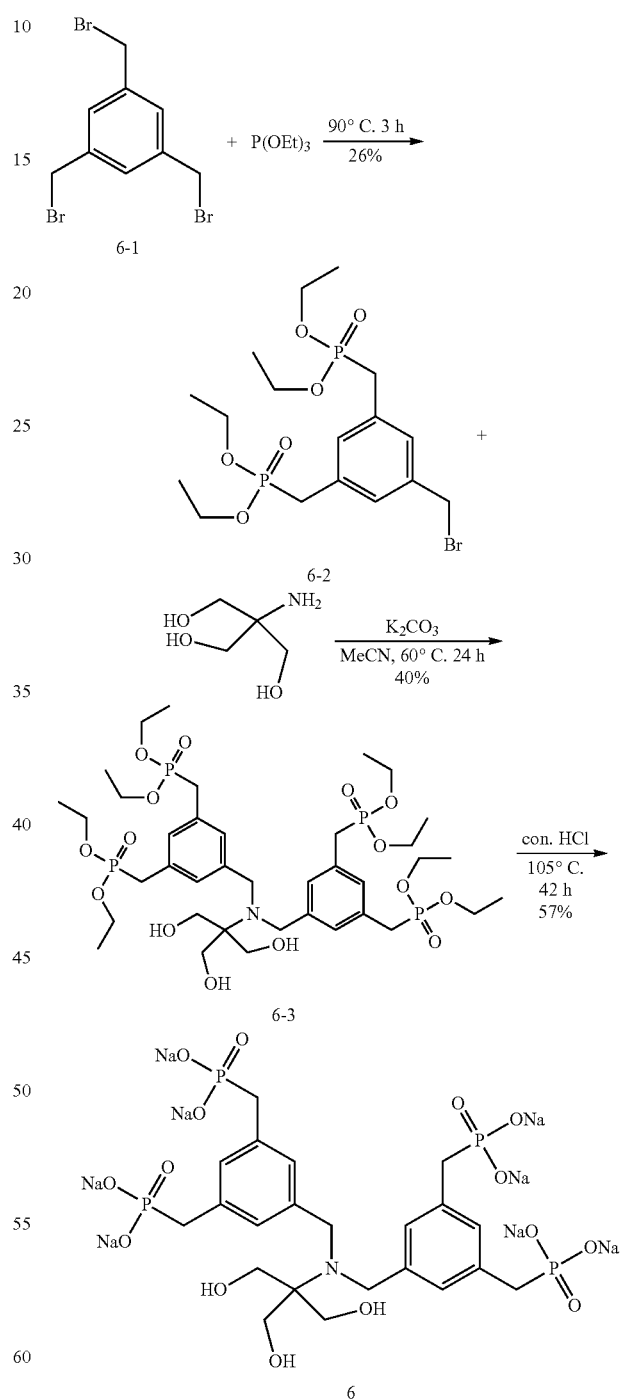

Step (1): To a 50 mL flask, was added 1,3,5-tris(bromomethyl)-benzene 7.14 g (20.0 mmol), triethyl phosphite 6.68 g (40.2 mmol). The flask was heated up in an oil bath. The mixture was stirred for 3 hrs under 90° C.

After removal of heating system, to the cool mixture was added 30 mL dichloromethane. The resulted mixture was kept stirring for 10 minutes, and was added 30 mL petroleum ether, and was stirred overnight. Then the suspension was filtered, the residue was washed with 30 mL solvent mixture of $CH_2Cl_2$ and petroleum ether (v/v, 1:5). The filtrate was collected and combined, concentrated to give a thick liquid which was purified by column chromatography to provide compound 6-2 2.45 g, 26% yield: $C_{17}H_{29}BrO_6P_2$, MS (ES+) m/z: 493.0 (M+Na)+.

Step (2): To a 50 mL flask was added, compound 6-2 (1040 mg, 2.2 mmol), tris amine (121 mg, 1.0 mmol), $K_2CO_3$ (304 mg, 2.2 mmol), and 15 mL acetonitrile. The mixture was stirred over 24 hrs under 60° C. After removal of heating system, to the cool mixture was added 50 mL dichloromethane. The resulted mixture was kept stirring for 10 minutes, and was added 20 mL $CH_2Cl_2$ twice, and was stirred overnight. Then the suspension was filtered, the residue was washed with 20 mL twice. The filtrate was collected and combined, concentrated to give a thick liquid which was purified by column chromatography to provide compound 6-3 with 360 mg with 40% yield, as a colorless liquid: $C_{38}H_{67}NO_{15}P_4$, MS (ES+) m/z: 902.4 (M+H)+.

Step (3): To a 50 mL flask was added, compound 6-3 with (360 mg, 0.4 mmol), 10 mL aqueous concentrate HCl. The reaction mixture was heated to 105° C. for 42 hrs, and was kept stirring. After the removal of heating system, the cool mixture was concentrated to result a pale solid, which was purified by resin column. The resulted solid was dissolved in water, and was added 2N NaOH. After concentration the solid was recrystallized by ethanol to give a while solid, compound 6, 210 mg, with 57% yield: $C_{22}H_{27}NNa_8O_{15}P_4 \cdot xH_2O$, MS (ES+) m/z: 678.1 (M+H)+.

Example 7: Synthesis of Compound 7

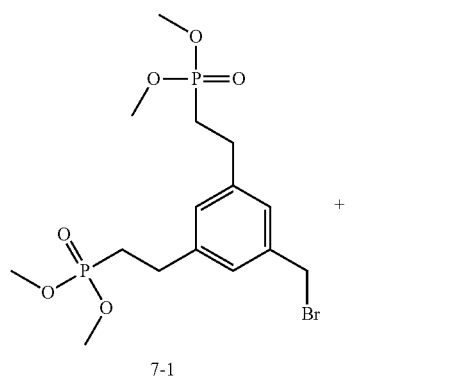

7-1

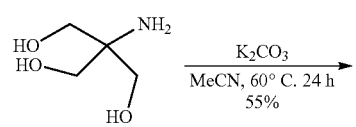

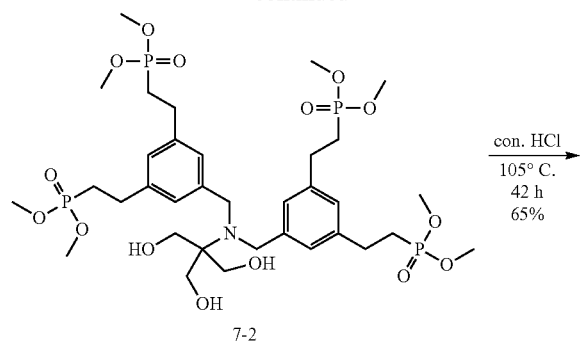

7-2

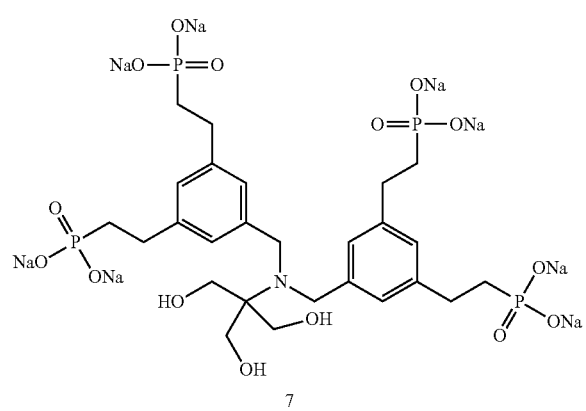

7

Step (1): To a 50 mL flask was added, compound 7-1 (972 mg, 2.2 mmol), tris amine (121 mg, 1.0 mmol) $K_2C_3$ (304 mg, 2.2 mmol), and 15 mL acetonitrile. The mixture was stiied over 24 hrs under 60° C. After removal of heating system, to the cool mixture was added 50 mL dichloromethane. The resulted mixture was kept stirring for 10 minutes, and was added 20 mL $CH_2Cl_2$ twice, and was stirred overnight. Then the suspension was filtered, the residue was washed with 20 mL twice. The filtrate was collected and combined, concentrated to give a thick liquid which was purified by column chromatography to provide compound 7-2 with 465 mg with 55% yield, as a colorless liquid: $C_{34}H_{59}NO_{15}P_4$, MS (ES+) m/z: 846.3 (M+H)+.

Step (2): To a 50 mL flask was added, compound 7-2 with (465 mg, 0.55 mmol), 10 mL aqueous concentrate HCl. The reaction mixture was heated to 105° C. for 42 hrs, and was kept stirring. After the removal of heating system, the cool mixture was concentrated to result a pale solid, which was purified by resin column. The resulted solid was dissolved in water, and was added 2N NaOH. After concentration the solid was recrystallized by ethanol to give a while solid, compound 7, 360 mg, with 65% yield: $C_{26}H_{35}NNa_8O_{15}P_4 \cdot xH_2O$, MS (ES+) m/z: 606.2 (M+H).

Example 8: Synthesis of Compound 8

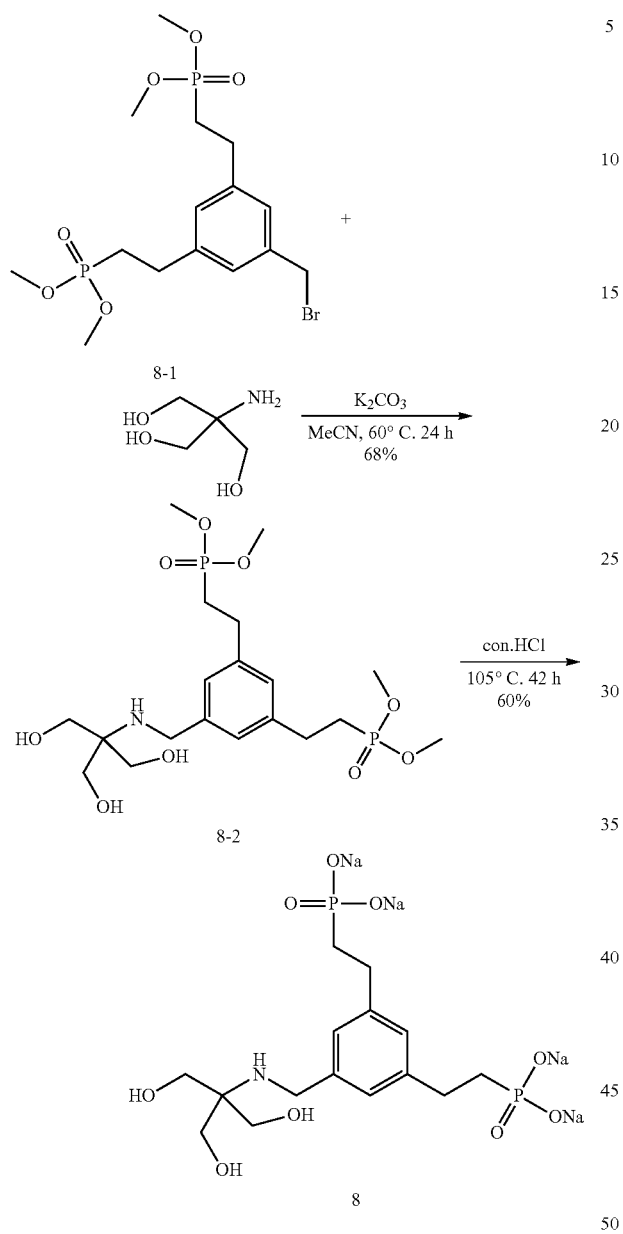

Step (1): To a 50 mL flask was added, compound 8-1 (663 mg, 1.5 mmol), tris amine (363 mg, 3.0 mmol), $K_2CO_3$ (207 mg, 1.5 mmol), and 10 mL acetonitrile. The mixture was stirred over 24 hrs under 60° C. After removal of heating system, to the cool mixture was added 50 mL dichloromethane. The resulted mixture was kept stirring for 10 minutes, and was added 20 mL $CH_2Cl_2$ twice, and was stirred overnight. Then the suspension was filtered, the residue was washed with 20 mL twice. The filtrate was collected and combined, concentrated to give a thick liquid which was purified by column chromatography to provide compound 8-2 with 465 mg with 55% yield, as a colorless liquid: $C_{34}H_9NO_{15}P_4$, MS (ES+) m/z: 846.3 (M+H).

Step (2): To a 50 mL flask was added, compound 8-2 with (493 mg, 1.02 mmol), 10 mL aqueous concentrate HCl. The reaction mixture was heated to 105° C. for 42 hrs, and was kept stirring. After the removal of heating system, the cool mixture was concentrated to result a pale solid, which was purified by resin column. The resulted solid was dissolved in water, and was added 2N NaOH. After concentration the solid was recrystallized by ethanol to give a while solid, compound 8, 349 mg, with 60% yield: $C_{15}H_{23}NNa_4O_9P_2 \cdot xH_2O$, MS (ES+) m/z: 428.1 (M+H)$^+$.

Example 9: Synthesis of Compound 9

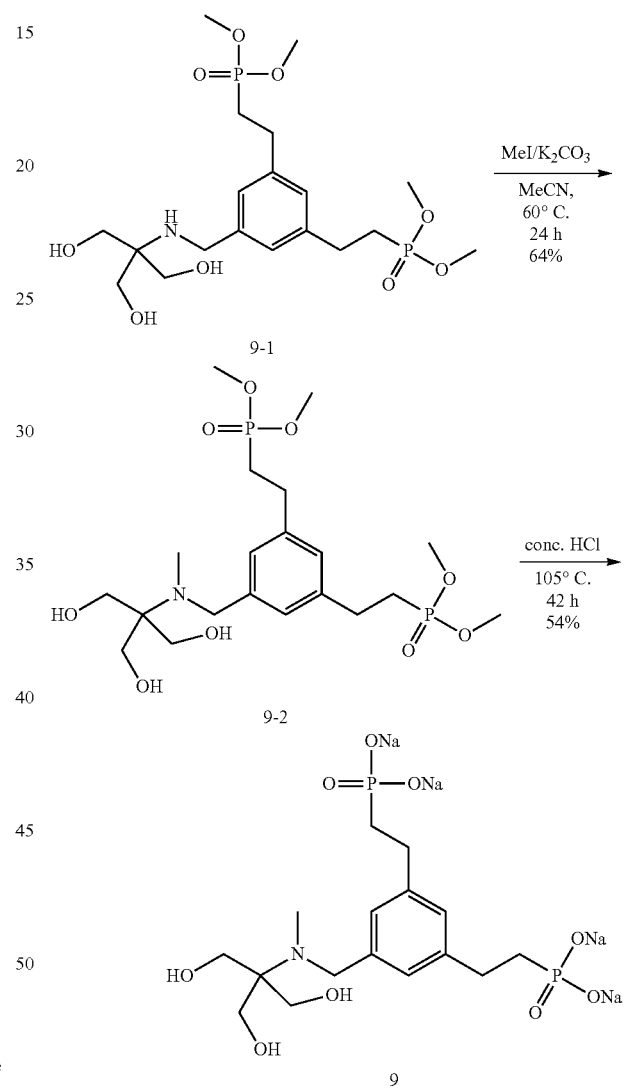

Step (1): To a 10 mL microwave tube was added, compound 9-1 (450 mg, 0.93 mmol), Methyl iodide (284 mg, 2.0 mmol), $K_2CO_3$ (276 mg, 2.0 mmol), and 4 mL acetonitrile. The mixture was warmed to 60 degree, and was kept stirring for 2 hrs. The reaction mixture was cooled to room temperature, filtrated. The filter residue was washed with dichloromethane 2×10 mL. The combined filtrate was concentrated to give a viscous liquid, which was purified by column chromatography to give compound 9-2 300 mg with 64% yield, as a colorless liquid: $C_{20}H_{37}NO_9P_2$, MS (ES+) m/z: 498.2 (M+H)$^+$.

Step (2): To a 50 mL flask was added, compound 9-2 with (300 mg, 0.6 mmol), 10 mL aqueous concentrate HCl. The reaction mixture was heated to 105° C. for 24 hrs, and was kept stirring. After the removal of heating system, the cool mixture was concentrated to result a pale solid, which was purified by resin column. The resulted solid was dissolved in water, and was added 2N NaOH. After concentration the solid was recrystallized by ethanol to give a while solid, compound 9, 170 mg, with 54% yield: $C_{16}H_{25}NNa_4O_9P_2 \cdot xH_2O$, MS (ES+) m/z: 442.1 (M+H)$^+$.

Example 10: Synthesis of Compound 10

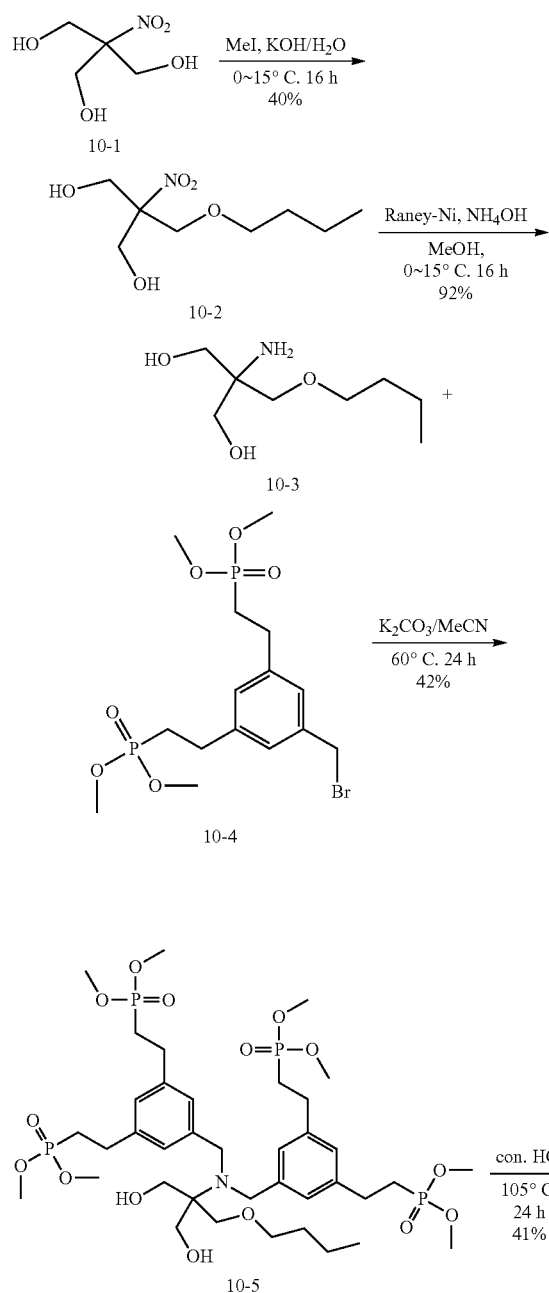

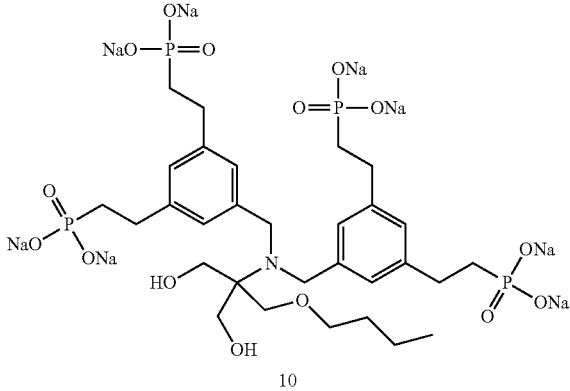

Step (1): To a 250 mL flask, was added 10-1 (15.1 g, 0.100 mol). The mixture was cooled down to zero degree, and was added dropwise aq. 50% KOH (50 mL), and kept stirring for 30 min. Bromo-butane (6.85 g, 50 mmol) was added to the mixture at 0° C. The reaction mixture was kept stirring for 16 hrs at 0-15° C. The cool reaction mixture was then poured into 200 mL sat. NH4Cl. The resulted mixture was extracted with dichloromethane and isoproplyl (v/v, 10:1) three times. The organic phases were combined and concentrated to result a thick liquid, which was purified by column chromatography to give compound 10-2 4.14 g with 40% yield as a pale yellow liquid: $C_8H_{17}NO_5$, MS (ES+) m/z: 230.1 (M+Na)$^+$.

Step (2): Compound 10-2 (4.14 g, 40 mmol) was dissolved in 80 mL methanol. And Raney nickel (800 mg), 4 mL concentrated ammonia was added to the solution. The mixture was furnished with hydrogen column at 1 atm, and was stirred for 16 hrs at 30° C. Then, the mixture was filtrated. The residue was washed with methanol (2×30 mL). The organic solution was combined and concentrated to result the desired compound 10-3 3.3 g, with 92% yield as a while solid: $C_8H_{19}NO_3$, MS (ES+) m/z: 178.1 (M+H)$^+$.

Step (3): Refer to step (1) of Example 8, to obtain 10-5, 180 mg, 41% yield, as a colorless liquid: $C_{30}H_{43}NNa_8O_{15}P_4 \cdot xH_2O$, MS (ES+) m/z: 790.2 (M+H)$^+$.

Step (4): Refer to step (2) of Example 8, to obtain Compound 10, 180 mg, 41% yield, as a while solid: $C_{30}H_{43}NNa_8O_{15}P_4 \cdot xH_2O$, MS (ES+) m/z: 790.2 (M+H)$^+$.

Example 11: Synthesis of Compound 11

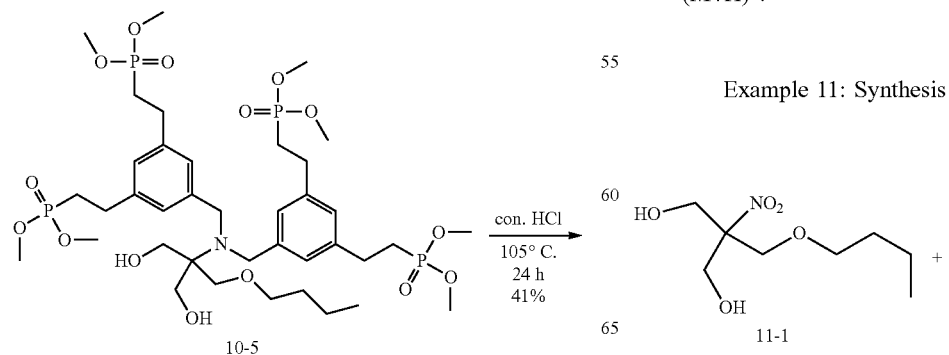

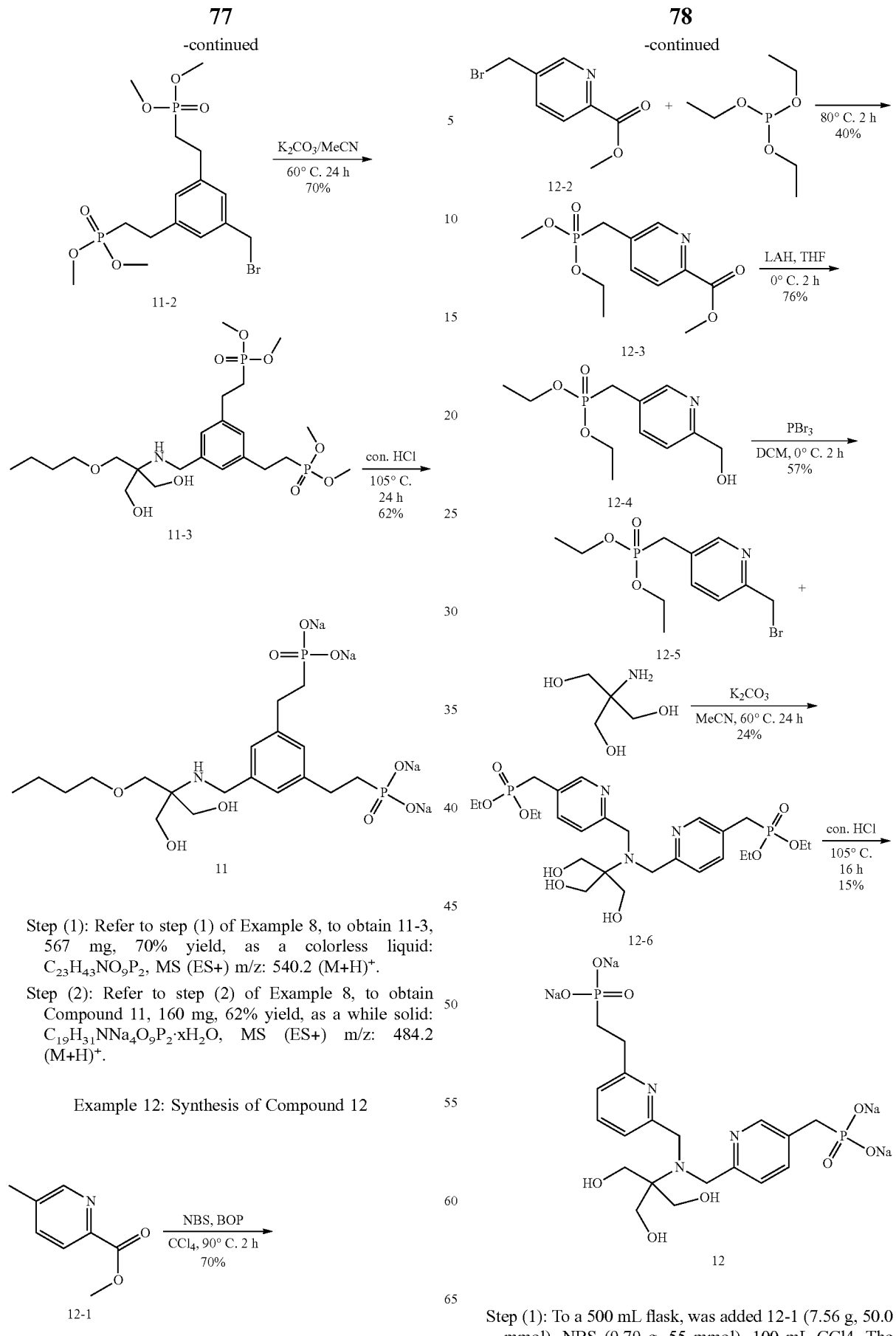
Step (1): Refer to step (1) of Example 8, to obtain 11-3, 567 mg, 70% yield, as a colorless liquid: $C_{23}H_{43}NO_9P_2$, MS (ES+) m/z: 540.2 (M+H)$^+$.
Step (2): Refer to step (2) of Example 8, to obtain Compound 11, 160 mg, 62% yield, as a while solid: $C_{19}H_{31}NNa_4O_9P_2 \cdot xH_2O$, MS (ES+) m/z: 484.2 (M+H)$^+$.
Example 12: Synthesis of Compound 12
Step (1): To a 500 mL flask, was added 12-1 (7.56 g, 50.0 mmol), NBS (9.79 g, 55 mmol), 100 mL CCl4. The solution was stirred 10 min at 90° C. under a oil bath, and followed with the addition of Dibenzoyl peroxide (BOP, 650 mg, 2.5 mmol). The reaction mixture was kept in flux for 2 hrs, and then cooled to r.t, was added 100 mL dichloromethane. And the mixture was washed with 100 mL water, aq. 5% NaHCO$_3$(2×100 mL). The organic layer was dried over Na$_2$SO$_4$, filtrated, and concentrated to give a crude product. The crude product was further purified by silico gel flash column chromatography to provide compound 12-2, 8.05 g, with 40% yield, as a viscous liquid: $C_{12}H_{18}NO_5P$, MS (ES+) m/z: 288.1 (M+H)$^+$.

Step (2): To a 100 mL flask, was added, compound 12-2 (8.05 g, 35 mmol), triethylphosphite (8.35 g, 50 mmol). The mixture was heated to 90 degree, and stirred for 3 hrs, and then cooled to r.t, and was concentrated to result a thick liquid which was purified by flash column chromatography to give compound 12-3, 4.02 g, with 40% yield as a viscous liquid: $C_{12}H_{18}NO_5P$, MS (ES+) m/z: 288.1 (M+H)$^+$.

Step (3): Compound 12-3 (3.75 g, 13.1 mmol) was dissolved in 50 mL THF in a 250 mL three-neck flask. The solution was cooled to 0° C., and was added dropwise 1 M LiAlH$_4$ (15.6 mL, 15.6 mmol). And the reaction was stirred over 2 hrs at 0° C. Na$_2$SO$_4$·10H$_2$O was added to the cold solution to quench the reaction. And the resulted mixture was filtrate. The residue was washed with FTE (2×50 mL). The organic solution was combined and dried over Na2SO4, and filtrated, and concentrated. The produced residue was purified by flash chromatography to give compound 12-4, 2.59 g, with 76% yield as a sticky liquid; $C_{11}H_{18}NO_4P$, MS (ES+) m/z: 260.1 (M+H)$^+$.

Step (4): To a 250 mL flask, was added, compound 12-4 (2.25 g, 8.7 mmol), and 50 mL DCM. The solution was cooled to 0° C., and, and was added PBr3 (4.72 g, 17.4 mmol), and kept stirring for 3 hrs. The solution was poured into 30 g ice, and was neutralized by 5% NaHCO$_3$. The mixture was extracted by DCM (3×60 mL). The organic phases were combined and dried over Na2SO4, filtered, and concentrated in low temperature to give a stick liquid which was washed with DCM and petroleum ether to give compound 12-5, 1.6 g, with 57% yield: $C_{11}H_{17}BrNO_3P$, MS (ES+) m/z: 322.0 (M+H)$^+$.

Step (5): Refer to step (1) of Example 8, to obtain 12-6, 320 mg, 24% yield, as a colorless liquid: $C_{26}H_{43}N309P_2$, MS (ES+) m/z: 604.2 (M+H)$^+$.

Step (6): Refer to step (2) of Example 8, to obtain Compound 12, 50 mg, 15% yield, as a while solid: $C_{18}H_{23}N_3Na_4O_9P_2$·xH$_2$O, MS (ES+) m/z: 492.1 (M+H)$^+$.

Example 13: Synthesis of Compound 13

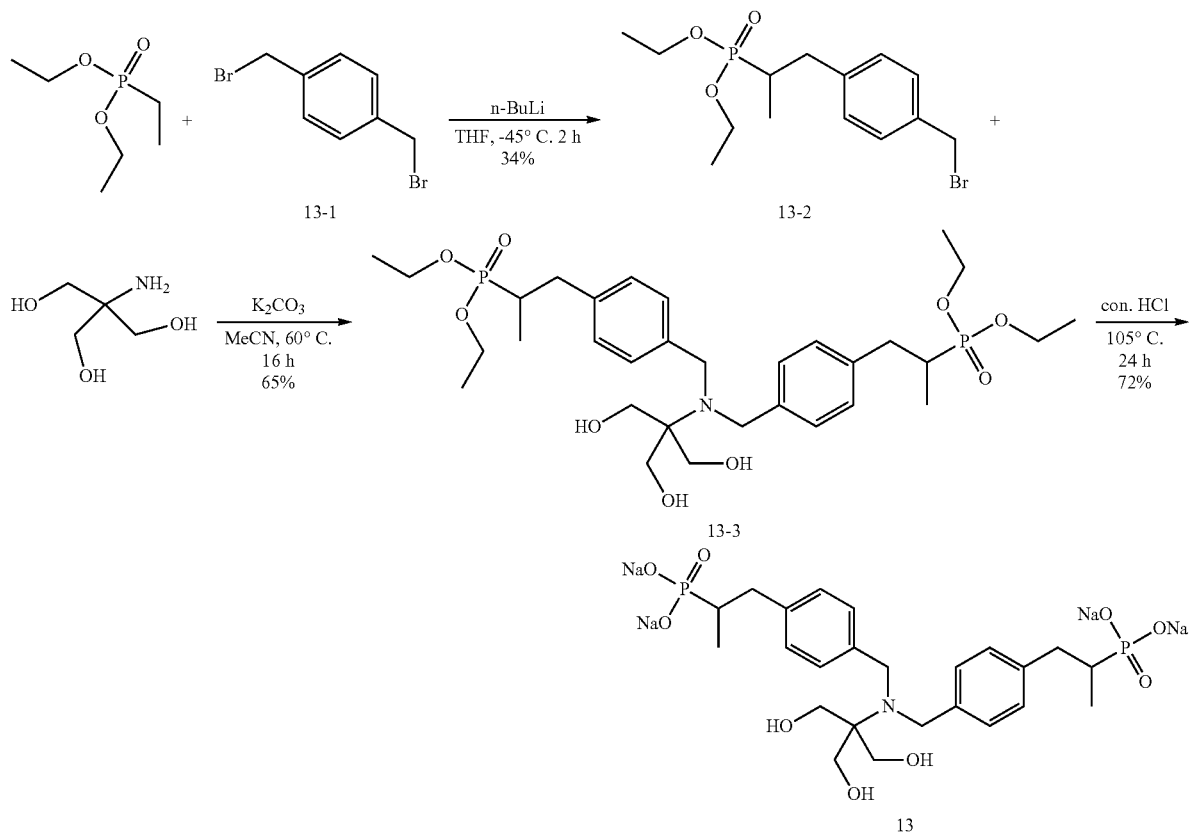

Step (1): To a 250 mL three neck flask, was added 40 mL of anhydrate THF, diethyl ethylphosphate (1.66 g, 10 mmol). The flask was cooled down to −78° C. via a dry ice-acetone bath, and was dropwise added 4 mL butyl lithium in hexane (10 mmol, 2.5M) in 30 minutes. After keep stirring for another hour at −78° C., 1,4-di (bromomethyl) benzene (2.64 g, 10 mol) in 10 mL of THF was added in 30 minutes. The mixture was kept stirring for 1 hr. LCMS showed the major product is desired. The reaction mixture was quenched by monopotassium phosphate (1 M, 40 mL), and was warmed up to room temperature. The mixture of liquid was separated by filtration funnel. The aqueous phase was washed by 50 mL of solvent mixture chloroform and isoproplyl (3:1) with four times. The organic phase was combined and added Na2SO4, filtered and concentrated. The residue was purified by flash chromatography to give compound 13-2 12 g, 34% yield as a yellow oil: $C_{14}H_{22}BrO_3P$, MS (ES+) m/z: 349.0 (M+H)$^+$.

Step (2): Refer to step (1) of Example 8, to obtain 13-4, 672 mg, 65% yield, as a colorless liquid: $C_{32}H_{53}NO_9P_2$, MS (ES+) m/z: 658.3 (M+H)$^+$.

Step (3): Refer to step (2) of Example 8, to obtain Compound 13, 514 mg, 72% yield, as a while solid: $C_{24}H_{33}NNa_4O_9P_2 \cdot xH_2O$, MS (ES+) m/z: 546.2 (M+H)$^+$.

Example 14: Synthesis of Compound 14

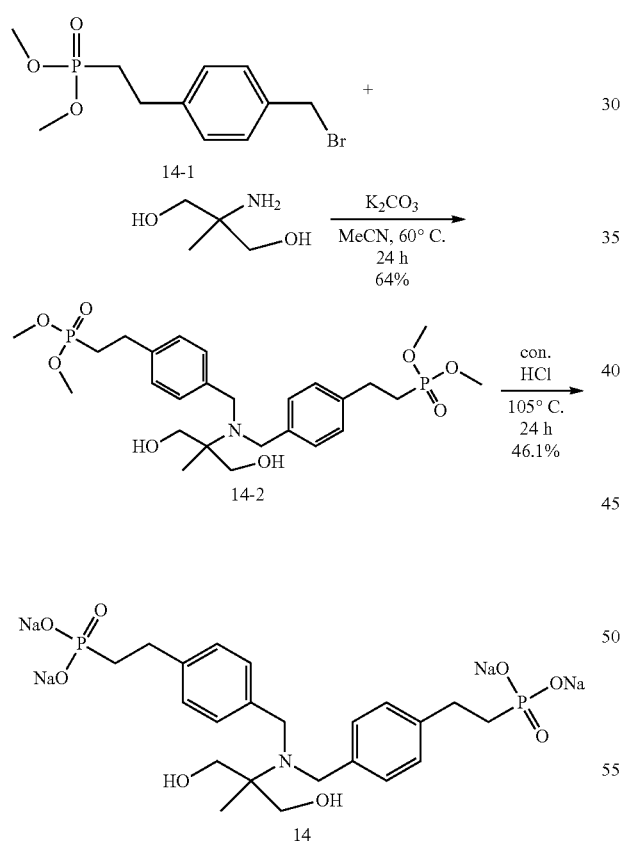

Step (1): Refer to step (1) of Example 8, to obtain 14-2, 380 mg, 68% yield, as a colorless liquid: $C_{26}H_{41}NO_8P_2$, MS (ES+) m/z: 558.2 (M+H)$^+$.

Step (2): Refer to step (2) of Example 8, to obtain Compound 14, 337 mg, 74% yield, as a while solid: $C_{22}H_{29}NNa_4O_8P_2 \cdot xH_2O$, MS (ES+) m/z: 502.2 (M+H)$^+$.

Example 15: Synthesis of Compound 15

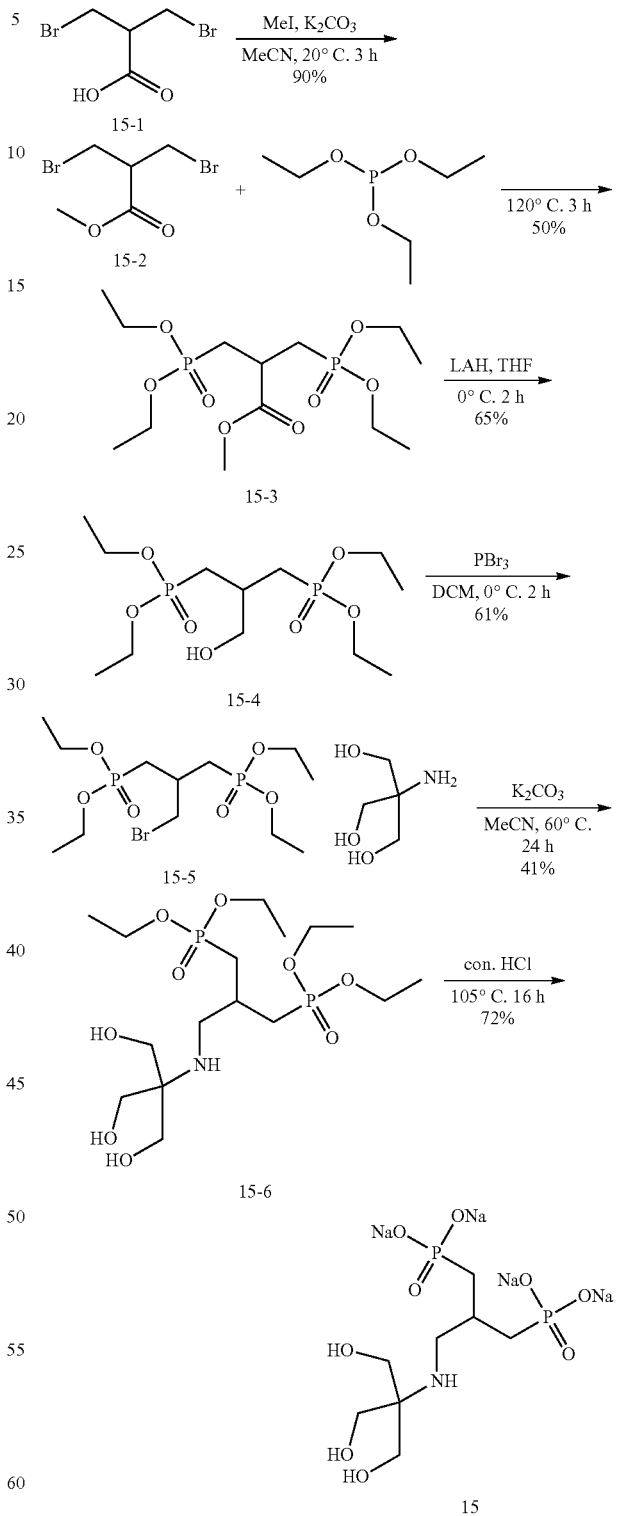

Step (1): To a 250 mL round flask, was added 15-1 (12.3 g, 50 mmol), K$_2$CO$_3$ (6.9 g, 50 mmol), and then added dropwise Methane iodide (10.65 g, 75 mmol) at 20 degree. The mixture was stirred for 3 hrs, and filtrated, concentrated. The filter residue was washed with DCM (2×50 mL). The combined organic solution was dried over NaSO4 to give the desired crude product 15-2, 11.7 g, 90% yield: $C_5H_8Br_2O_2$, MS (ES+) m/z: 281.0 (M+Na)+, which was directly used to next step.

Step (2): To a 100 mL flask, was added, compound 15-2 (11.0 g, 42.5 mmol), triethylphosphite (21.2 g, 127 mmol). The mixture was heated to 120 degree, and stirred for 3 hrs, and then cooled to r.t, and was concentrated to result a thick liquid which was purified by flash column chromatography to give compound 15-3, 7.96 g, with 50% yield as a viscous liquid: $C_{13}H_{28}O_8P_2$, MS (ES+) m/z: 375.1 (M+H)+.

Step (3): Compound 15-3 (7.5 g, 20 mmol) was dissolved in 100 mL THF in a 500 mL three-neck flask. The solution was cooled to 0° C., and was added dropwise 1 M LiAlH4 (15.6 mL, 15.6 mmol). And the reaction was stirred over 2 hrs at 0° C. $Na_2SO_4 \cdot 10H_2O$ was added to the cold solution to quench the reaction. And the resulted mixture was filtrate. The residue was washed with THF (2×100 mL). The organic solution was combined and dried over $Na_2SO_4$, and filtrated, and concentrated. The produced residue was purified by flash chromatography to give compound 15-4, 4.5 g, with 65% yield as a sticky liquid: $C_{12}H_{28}O_7P_2$, MS (ES+) m/z: 347.1 (M+H)+.

Step (4): To a 250 mL flask, was added, compound 15-4 (4.3 g, 12.4 mmol), and 0 mL DCM. The solution was cooled to 0° C., and, and was added PBr3 (5.04 g, 18.6 mmol), and kept stirring for 3 hrs. The solution was poured into 50 g ice, and was neutralized by 5% NaHCO3. The mixture was extracted by DCM (3×80 mL). The organic phases were combined and dried over $Na_2SO_4$, filtered, and concentrated in low temperature to give a stick liquid which was washed with DCM and petroleum ether to give compound 15-5, 3.1 g, with 61% yield: $C_{12}H_{27}BrO_6P_2$, MS (ES+) m/z: 409.0 (M+H)+.

Step (5): Refer to step (1) of Example 8, to obtain 15-6, 276 mg, 41% yield, as a colorless liquid: $C_{16}H_{37}NO_9P_2$, MS (ES+) m/z: 450.2 (M+H)+.

Step (6): Refer to step (2) of Example 8, to obtain Compound 15, 220 mg, 72% yield, as a while solid: $C_8H_{17}NNa_4O_9P_2 \cdot xH_2O$, MS (ES+) m/z: 338.1 (M+H)+.

Example 16: Synthesis of Compound 16

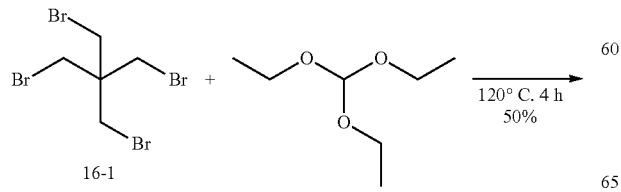

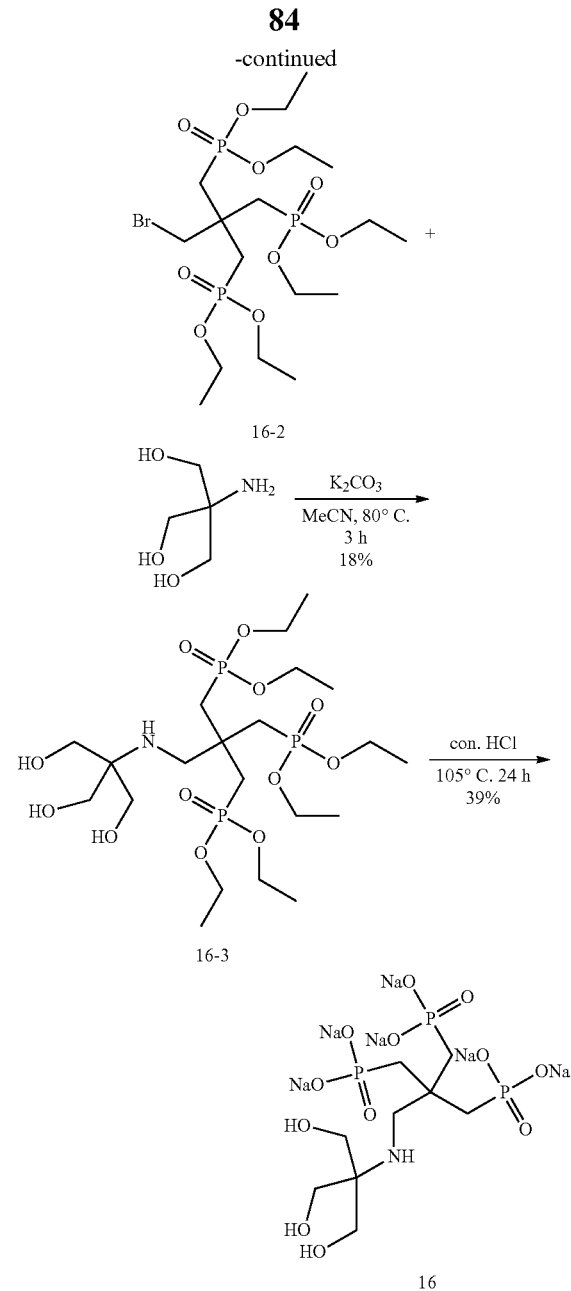

Step (1): To a 50 mL round flask, was added 1,3-dibromo-2,2-bis(bromomethyl)-propane (7.76 g, 20.0 mmol), triethyl phosphite (13.3 g, 40.2 mmol). The flask was heated up in an oil bath. The mixture was stirred for 3 hrs under 120° C. After removal of heating system, to the cool mixture was added 30 mL dichloromethane. The resulted mixture was kept stirring for 10 minutes, and was added 30 mL petroleum ether, and was stirred overnight. Then the suspension was filtered, the residue was washed with 30 mL solvent mixture of $CH_2Cl_2$ and petroleum ether (v/v, 1:5). The filtrate was collected and combined, concentrated to give a thick liquid which was purified by column chromatography to provide compound 16-2 5.6 g, 50% yield: $C_{17}H_{38}BrO_9P_3$, MS (ES+) m/z: 559.1 (M+H)+.

Step (2): Refer to step (1) of Example 8, to obtain 16-3, 520 mg, 18% yield, as a colorless liquid: $C_{21}H_{48}NO_{12}P_3$, MS (ES+) m/z: 600.2 (M+H)+.

Step (3): Refer to step (2) of Example 8, to obtain Compound 16, 210 mg, 39% yield, as a while solid: $C_9H_{18}NNa_6O_{12}P_3 \cdot xH_2O$, MS (ES+) m/z: 432.1 $(M+H)^+$.

Example 17: Synthesis of Compound 17

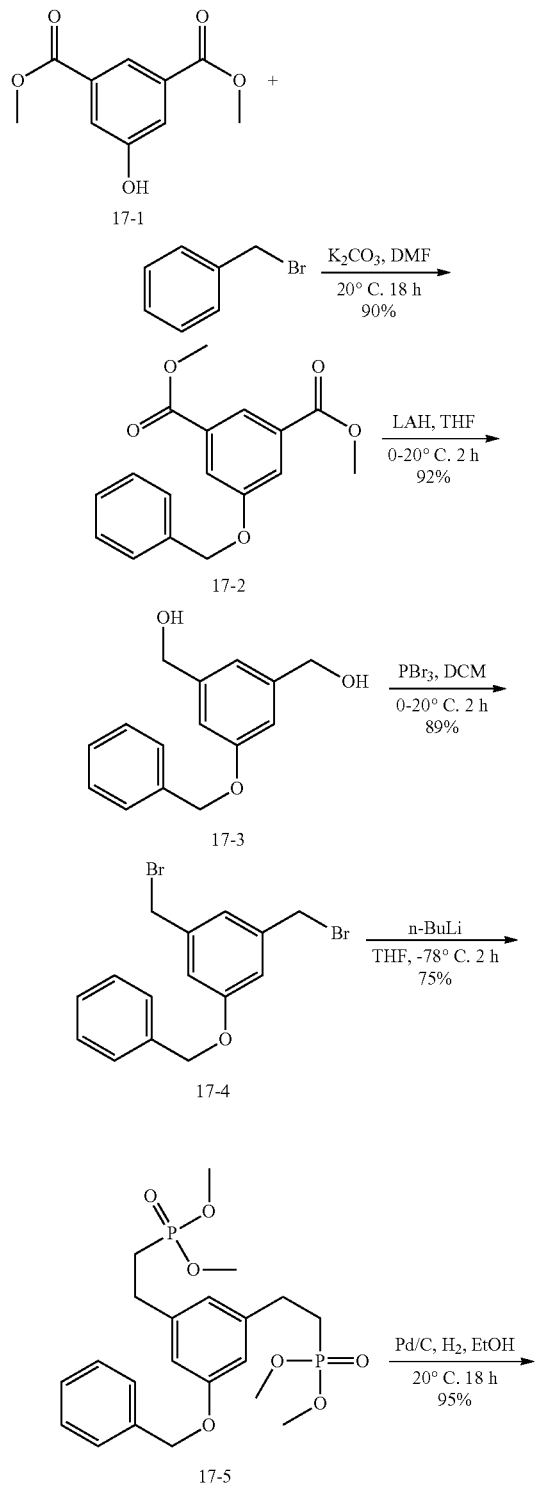

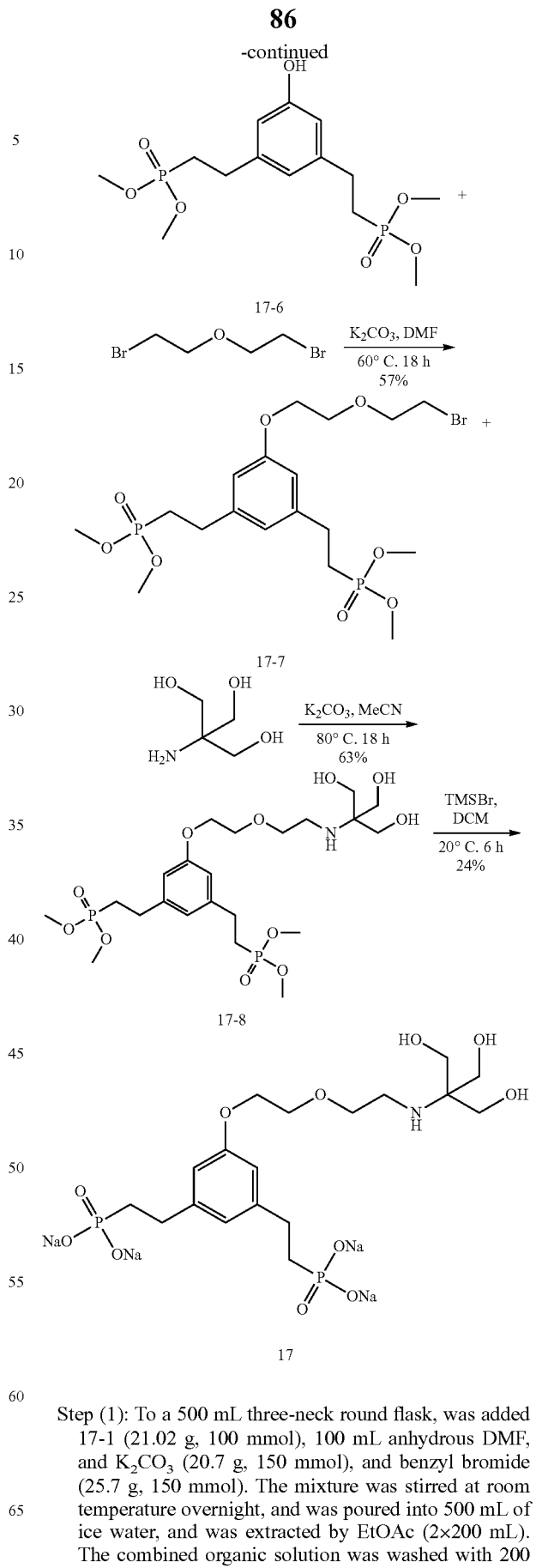

Step (1): To a 500 mL three-neck round flask, was added 17-1 (21.02 g, 100 mmol), 100 mL anhydrous DMF, and $K_2CO_3$ (20.7 g, 150 mmol), and benzyl bromide (25.7 g, 150 mmol). The mixture was stirred at room temperature overnight, and was poured into 500 mL of ice water, and was extracted by EtOAc (2×200 mL). The combined organic solution was washed with 200 mL water, 200 mL brine, and was dried over Na2SO4. The suspension was filtrated. The liquid phase was concentrated to give crude product which was purified by flash chromatography to give 17-2, 27 g, 90% yield: $C_{17}H_{16}O_5$, MS (ES+) m/z: 323.1 (M+Na)+.

Step (2): To a 1000 mL three-neck round flask, was added, 17-2 (27 g, 90 mmol), and 200 mL anhydrous THF. The mixture was cooled to 0° C., and was added dropwise 1 M LiALH4 (198 mL, 198 mmol). The suspension was stirred at 0-20° C. for 2 hrs, and was cooled to 0° C. To the mixture, 50 g of aqueous $Na_2SO_4$ was carefully added in batches. The resulted mixture was filtrated. The filter residue was washed with 200 mL DCM. The combined organic solution was dried over $Na_2SO_4$, filtrated, concentrated to give the crude product 17-3, 20.2 g, with 92% yield as a viscous liquid: $C_{15}H_{16}O_3$, MS (ES+) m/z: 267.1 (M+Na)+.

Step (3): To a 1000 mL three-neck round flask, was added 17-3 (20.2 g, 82.7 mmol), 200 mL anhydrous DCM. The mixture was cooled to 0 degree, and was added slowly PBr3 (67.2 g, 248 mmol). The reaction mixture was stirred at 0-20° C. for 2 hrs, and was poured into 500 g of ice water carefully, and was extracted with DCM (2×200 mL). the combined organic solution was washed with 200 brine, and dried over $Na_2SO_4$, filtrated, concentrated to give 17-4,27.5 g, with 89% yield as a pale yellow solid: $C_{15}H_{14}Br_2O$, MS (ES+) m/z: 391.0 (M+Na)+.

Step (4): To a 1000 mL three-neck flask, was added 400 mL of anhydrate THF, dimethyl-methylphosphate (23.06 g, 186 mmol). The flask was cooled down to −78° C. via a dry ice-acetone bath, and was dropwise added 74.4 mL butyl lithium in hexane (186 mmol, 2.5M) in 30 minutes. After keep stirring for another hour at −78° C., 17-4(27.5 g, 74.3 mmol) in 100 mL of THF was added in 30 minutes. The mixture was kept stirring for 1 hr. LCMS showed the major product is desired. The reaction mixture was quenched by mono-potassium phosphate (1M, 100 mL), and was warmed up to room temperature. The mixture of liquid was separated by filtration funnel. The aqueous phase was washed by 50 mL of solvent mixture chloroform and isoproplyl (3:1) with four times. The organic phase was combined and added $Na_2SO_4$, filtered and concentrated. The residue was purified to give compound 17-5, 25.4 g, with 75% yield: $C_{21}H_{30}O_7P_2$, MS (ES+) m/z: 479.2 (M+Na)+.

Step (5): the mixture of 17-5 (25.4 g, 55.7 mmol) in 250 mL ethanol, was added 1 g of 10% Pd/C, and degas, in a 1000 mL three-neck flask. Hydrogen balloon at 1 atm was installed. And the mixture was stirred over 18 hrs at r.t. The mixtures was filtered. And the mother liquid was concentrated to give desired 17-6, 19.4 g, with 95% yield as a pale yellow solid: $C_{14}H_{24}O_7P_2$, MS (ES+) m/z: 389.1 (M+Na)+.

Step (6): To a 100 mL round flask, was added 17-6 (1.83 g, 5.0 mmol), 1-bromo-2-(2-ethoxyl) ethane (2.32 g, 10.0 mmol), $K_2CO_3$ (1.38 g, 10.0 mmol), and 20 mL anhydrous DMF. The mixture was stirred for 18 hrs at 60° C. Then the reaction mixture was poured into 120 mL of ice water, and was extracted with EtOAc (2×120 mL), The combined organic solvent was combined, and dried over $Na_2SO_4$, and filtrated. The solution was concentrated. And the residue was purified by flash chromatography to give 1707, 1.47 g, with 57% yield, as a viscous liquid: $C_{18}H_{31}BrO_8P_2$, MS (ES+) m/z: 517.1 (M+H)+.

Step (7): Refer to step (1) of Example 8, to obtain 17-8, 914 mg, 63% yield, as a colorless liquid: $C_{22}H_{41}NO_{11}P_2$, MS (ES+) m/z: 558.2 (M+H)+.

Step (8): Refer to step (2) of Example 8, to obtain Compound 17, 236 mg, 24% yield, as a while solid: $C_{18}H_{29}NNa_4O_{11}P_2 \cdot xH_2O$, MS (ES+) m/z: 502.2 (M+H)+.

Example 18: Synthesis of Compound 18

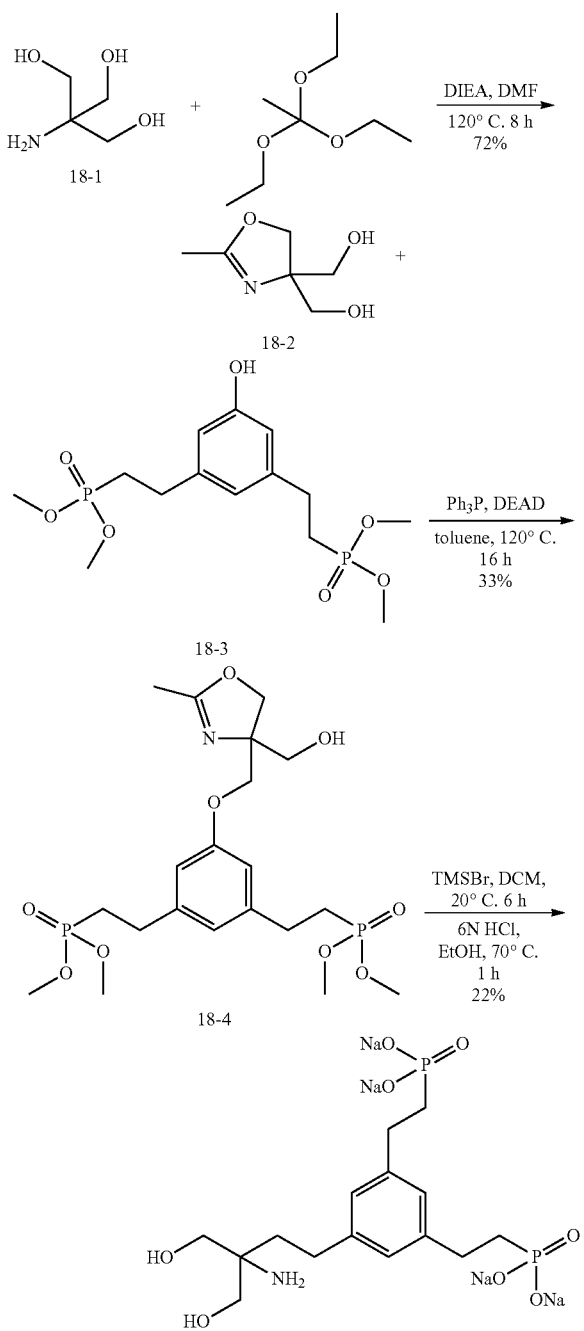

Step (1): To a 250 mL round flask, was added, tris amine (5.0 g, 41.3 mmol), 50 mL DMF, 9.1 mL triethyl orthoacetate, and 7.2 mL DIPEA. The mixture was stirred 8 hrs at 120° C. After the removal of solvent and addition of 100 mL petroleum ether, the solid was precipitated out. The solid was collected as product 18-2, 4.31 g, with 72& yield: $C_6H_{11}NO_3$, MS (ES+) m/z: 146.1 (M+H)$^+$.

Step (2): To a 250 mL tree-neck round flask, was added, triphenyl phosphine (576 mg, 2.2 mmol), and 40 mL anhydrous toluene. The solution was cooled to 0° C., and was slowly added DEAD (383 mg, 2.2 mmol). After stirring 30 min at 0° C., 18-3 (732 mg, 2.0 mmol) and 18-2 (436 mg, 3.0 mmol) was added. The resulted reaction mixture was refluxed for 16 hrs, and concentrated. The residue was purified by flash chromatography to give 18-4, 325 mg, with 33% yield as a viscous liquid: $C_{20}H_{33}NO_9P_2$, MS (ES+) m/z: 494.2 (M+H)$^+$.

Step (3): 18-4 (325 mg, 0.67 mmol) was dissolved in 10 mL DCM in a 50 mL round flask. The mixture was cooled to 0° C., at $N_2$ atmosphere, was dropwise added 3 mL TMS-Br. The reaction was gradually increased to 20° C. within 1 hr, and kept stirring for 6 hrs. The reaction solution was concentrated to result a viscous liquid. 2 mL anhydrous ethanol was added to the residue, and followed with 2 mL of 6 N HCl. And the mixture was heated to 70° C., and was kept stirring for another 1 hr. The mixture was cooled down, and was concentrated to give a viscous liquid. To it was added 10 mL DCM and 5 mL methanol, and kept stirring for 30 min at 20° C. The mixture was concentrated to dry again. And residue was purified by resin column chromatography to give compound 18, 82 mg, with 22% yield: $C_{14}H_{21}NNa_4O_9P_2 \cdot xH_2O$, MS (ES+) m/z: 414.1 (M+H)$^+$.

Example 19: Synthesis of Compound 19

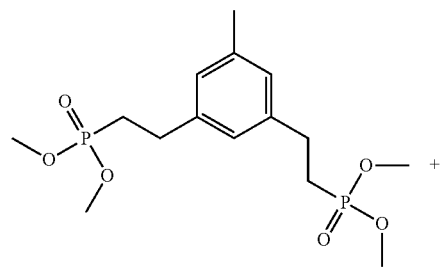

19-1

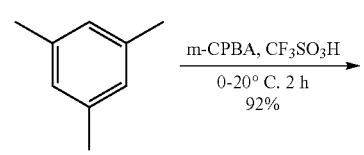

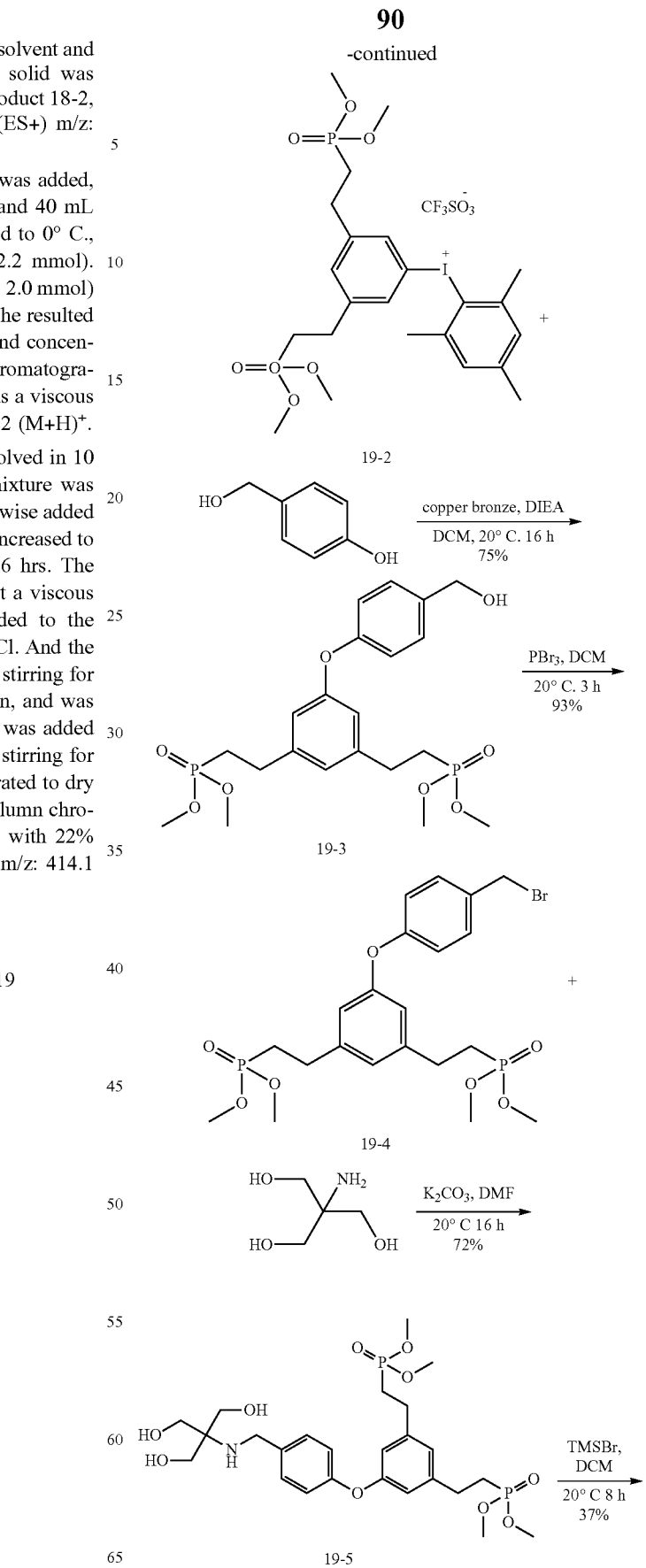

-continued

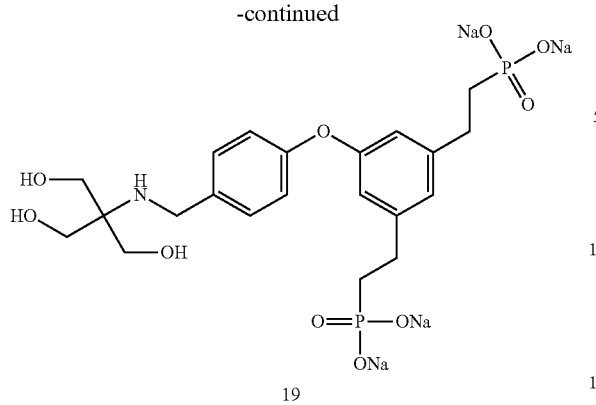

19

Step (1): To a 50 mL dry round flask was added, m-CPBA (759 mg, 4.4 mmol), and 步 40 mL anhydrous DCM. To the mixture, 19-1 (1.90 g, 4.0 mmol), and mesitylene (5.29 g, 4.4 mmol) were added. The mixture was cooled to 0° C., and was slowly dropwise added trifluoromethanesulfonic acid (1.02 g, 6.8 mmol), and stirred for 2 hours at 20° C. DCM was concentrated in lower temperature. And 100 mL ethyl ether was added to the residue, and the suspension was filtrated. The solid was collected as product 19-2, 2.74 g, with 92% yield: $C_{24}H_{34}F_3IO_9P_2S$, MS (ES+) m/z: 595.1 (M+)+.

Step (2): To a dry 100 mL round flask, was added 19-2(1.30 g, 1.75 mmol), 20 mL anhydrous DCM. To the mixture, a 10 mL solution of 4-hydroxymethylphenol (282 mg, 2.27 mmol, and DIPEA (677 mg, 5.25 mmol) in DCM was dropwise added at 20° C. The reaction mixture was stirred for 16 hours. And after removal of DCM by rotation evaporation, the residue was purified by flash column chromatography to give 19-3, 620 mg, with 75% yield: $C_{21}H_{30}O_8P_2$, MS (ES+) m/z: 473.1 (M+H)+.

Step (3): To a 50 mL three-neck round flask, was added, 19-3 (620 mg, 1.31 mmol), and 10 mL anhydrous dichloromethane. Under ice-water bath, the PBr3 (710 mg, 2.62 mmol) was added at 0° C. The mixture was stirred for 3 hrs at 0-20° C., and then was poured into 50 g ic. The mixture was extracted with DCM (3×50 mL). The combined organic phase was washed with 100 brine. The organic layer was dried over $Na_2SO_4$, and filtrated, and concentrated. The residue was 19-4, 652 mg, 93% yield: $C_{21}H_{29}BrO_7P_2$, MS (ES+) m/z: 535.1 (M+H)+.

Step (4): Refer to step (1) of Example 8, to obtain 19-5, 506 mg, 72% yield, as a colorless liquid: $C_{25}H_{39}NO_{10}P_2$, MS (ES+) m/z: 576.2 (M+H)+.

Step (5): Refer to step (2) of Example 8, to obtain Compound 19, 215 mg, 37% yield, as a while solid: $C_{21}H_{27}NNa_4O_{10}P_2 \cdot xH_2O$, MS (ES+) m/z: 520.1 (M+H)+.

Example 20: Synthesis of Compound 20

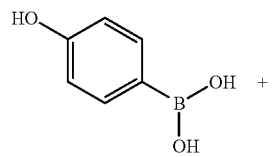

-continued

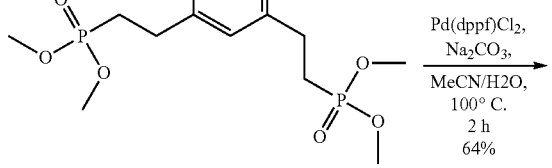

20-1

20-2

20-3

20-4

20

Step (1): To a 50 mL round flask, was added, 20-1 (954 mg, 2.0 mmol), Pd(dppf)Cl₂ (146 mg, 0.2 mmol), Na₂CO₃ (424 mg, 4.0 mmol), and 10 mL acetonitrile and 1 mL water. The mixtures was degas with argon, and was stirred for 5 min at r.t, and then was added DIPEA (413 mg, 3.2 mmol), and 4-hydroxy-phenylboronic acid (404 mg, 3.2 mmol). The mixture was stirred for 8 hrs at 100° C. After the removal of solvent, the residue was purified by chromatography to give 20-2, 567 mg, with 64% yield: $C_{20}H_{28}O_7P_2S$, MS (ES+) m/z: 443.1 $(M+H)^+$.

Step (2): To a 250 mL tree-neck round flask, was added, triphenyl phosphine (369 mg, 1.41 mmol), and 30 mL anhydrous toluene. The solution was cooled to 0° C., and was slowly added DEAD (245 mg, 1.41 mmol). After stirring 30 min at 0° C., 20-2 (567 mg, 1.28 mmol) and 20-3 (279 mg, 1.92 mmol) was added. The resulted reaction mixture was refluxed for 16 hrs, and concentrated. The residue was purified by flash chromatography to give 20-4, 299 mg, with 41% yield as a viscous liquid: $C_{26}H_{37}NO_9P_2$, MS (ES+) m/z: 570.2 $(M+H)^+$.

Step (3): 20-4 (299 mg, 0.525 mmol) was dissolved in 10 mL DCM in a 50 mL round flask. The mixture was cooled to 0° C., at $N_2$ atmosphere, was dropwise added 3 mL TMS-Br. The reaction was gradually increased to 20° C. within 1 hr, and kept stirring for 6 hrs. The reaction solution was concentrated to result a viscous liquid. 2 mL anhydrous ethanol was added to the residue, and followed with 2 mL of 6 N HCl. And the mixture was heated to 70° C., and was kept stirring for another 1 hr. The mixture was cooled down, and was concentrated to give a viscous liquid. To it was added 10 mL DCM and 5 mL methanol, and kept stirring for 30 min at 20° C. The mixture was concentrated to dry again. And residue was purified by resin column chromatography to give compound 19, 142 mg, with 43% yield: $C_{20}H_{25}NNa_4O_9P_2 \cdot xH_2O$, MS (ES+) m/z: 490.1 $(M+H)^+$.

Example 21: Synthesis of Compound 21

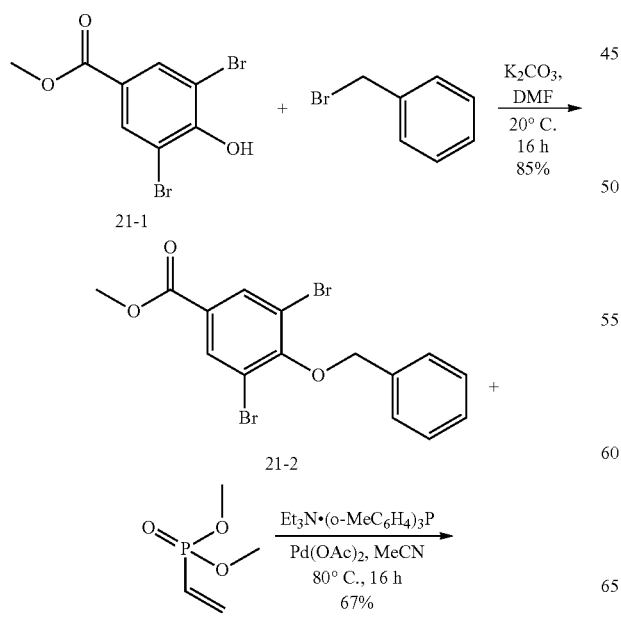

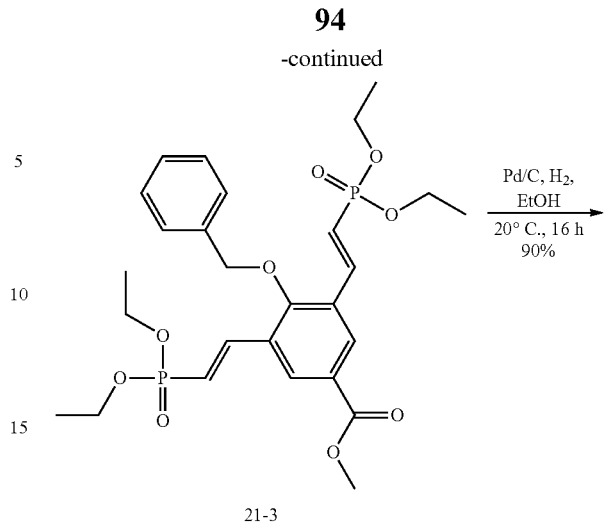

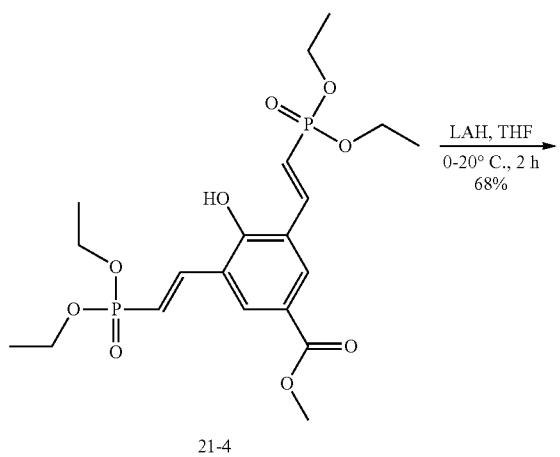

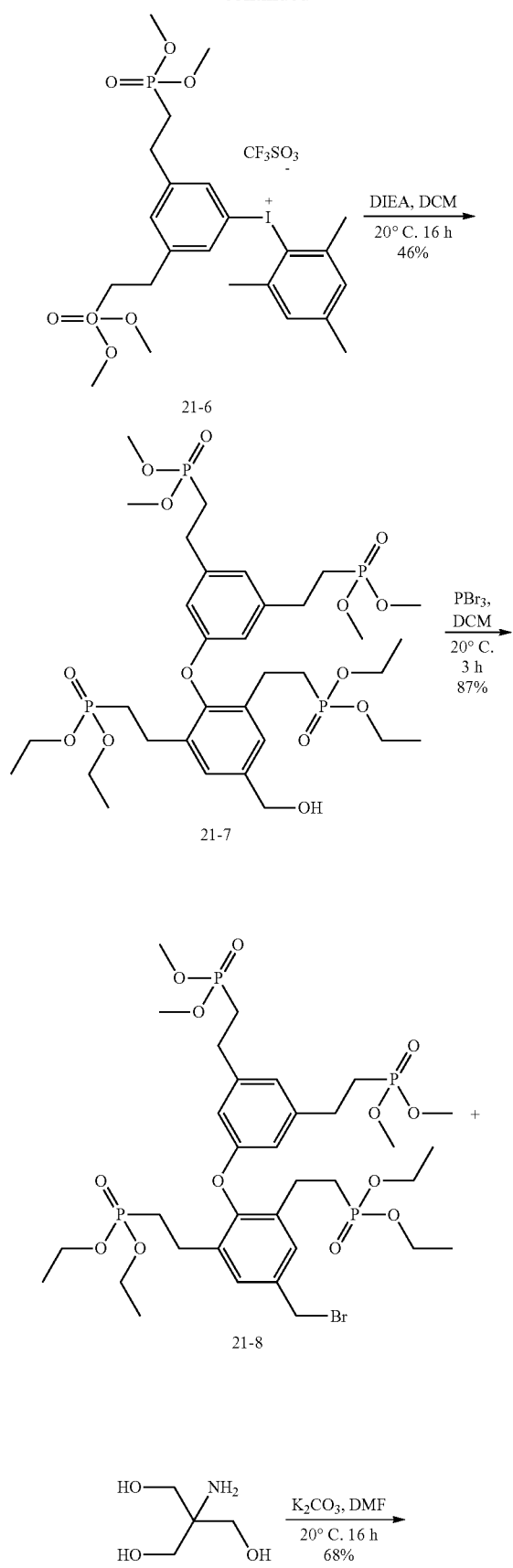
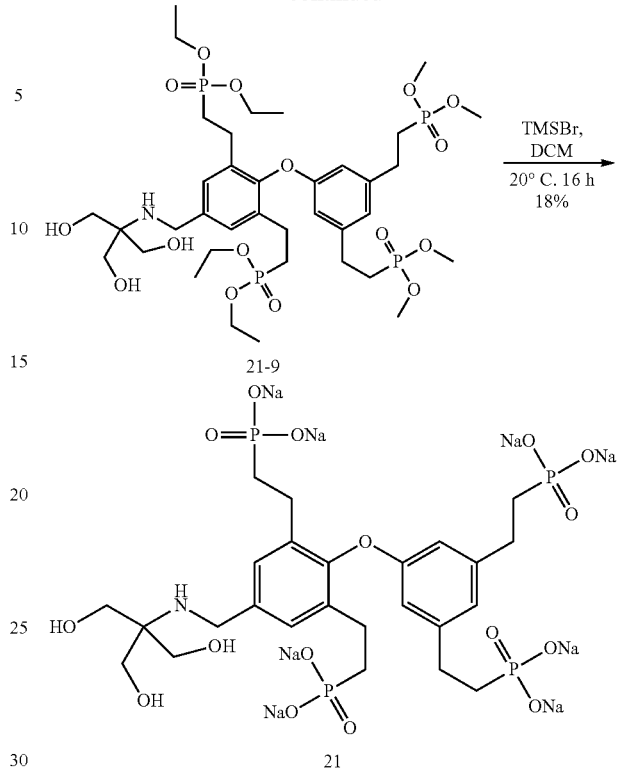

Step (1): To a 100 mL round flask, was added, 21-1 (6.2 g, 20 mmol), $K_2CO_3$ (4.14 g, 30 mmol), 30 mL anhydrous DMF. The reaction mixture was stirred for 16 hrs at 20° C., and then was poured into 200 mL ice-water. The mixture was extracted with EtOAc (2×100 mL). The combined organic phases were washed with 200 mL water, 200 mL brine, and was dried over $Na_2SO_4$, and was filtered. After the removal of solvent by rotation evaporation, the residue was purified by flash column chromatography to give 21-2, 6.78 g, with 85% yield: $C_{15}H_{12}Br_2O_3$, MS (ES+) m/z: 421.0 (M+Na)$^+$.

Step (2): To a 250 mL round flask, was added, 21-2 (6.5 g, 16.3 mmol), diethyl vinyl-phosphate (8.03 g, 48.9 mmol), TEA (6.59 g, 65.2 mmol), tris-(o-methyl phenyl)-phosphine (496 mg, 1.63 mmol), Pd (OAc)$_2$ (183 mg, 0.82 mmol), and 100 mL acetonitrile. The mixtures was stirred for 16 hrs under $N_2$ atmosphere. The mixture was filtrated, and concentrated to produce a residue which was purified by flash column chromatography to give 21-3, 6.18 g, with 67% yield as a viscous liquid: $C_{27}H_{36}O_9P_2$, MS (ES+) m/z: 566.2 (M+H)$^+$.

Step (3): (3): 21-3 (3.0 g, 5.3 mmol) was dissolved in 30 mL ethanol, and was hydrogenated with 10% Pd/C for 16 hrs. A off-red solid was obtained as 21-4, 2.29 g, with 90% yield: $C_{20}H_{34}O_9P_2$, MS (ES+) m/z: 481.2 (M+H)$^+$.

Step (4): Compound 21-4 (2.7 g, 4.37 mmol) was dissolved in 30 mL THF in a 100 mL three-neck flask. The solution was cooled to 0° C., and was added dropwise 1 M LiAlH$_4$ (8.7 mL, 8.7 mmol). And the reaction was stirred over 2 hrs at 0° C. 5 g Na$_2$SO$_4$·10H$_2$O was added to the cold solution to quench the reaction. And the resulted mixture was filtrate. The residue was washed with FTE (2×100 mL). The organic solution was combined and dried over Na2SO4, and filtrated, and concentrated. The produced residue was purified by flash chromatography to give compound 20-5, 1.34 g, with 68% yield as a pale red solid: $C_{19}H_{34}O_8P_2$, MS (ES+) m/z: 453.2 (M+H)+.

Step (5): To a dry 100 mL three-neck round flask, was added 21-6 (1.64 g, 2.21 mmol), 20 mL anhydrous DCM. To the mixture, a 10 mL solution of 21-5 (1.20 g, 2.65 mmol), and DIPEA (685 mg, 5.3 mmol) in DCM was dropwise added at 20° C. The reaction mixture was stirred for 16 hours. And after removal of DCM by rotation evaporation, the residue was purified by flash column chromatography to give 21-7, 815 mg, with 46% yield: $C_{33}H_{56}O_{14}P_4$, MS (ES+) m/z: 801.3 (M+H)+.

Step (6): To a 50 mL three-neck round flask, was added, 21-7 (815 mg, 1.02 mmol), and 10 mL anhydrous dichloromethane. Under ice-water bath, the PBr3 (551 mg, 2.03 mmol) was added at 0° C. The mixture was stirred for 3 hrs at 0-20° C., and then was poured into 50 g ice-water. The mixture was extracted with DCM (3×50 mL). The combined organic phase was washed with 100 mL brine. The organic layer was dried over $Na_2SO_4$, and filtrated, and concentrated. The viscous residue was identified as 20-8, 764 mg, 87% yield: $C_{33}H_{55}BrO_{13}P_4$, MS (ES+) m/z: 863.2 (M+H)+.

Step (7): Refer to step (1) of Example 8, to obtain 21-9, 543 mg, 68% yield, as a colorless liquid: $C_{37}H_{65}NO_{16}P_4$, MS (ES+) m/z: 904.3 (M+H)+.

Step (8): Refer to step (2) of Example 8, to obtain Compound 21, 97 mg, 18% yield, as a while solid: $C_{25}H_{33}NNa_8O_{16}P_4 \cdot xH_2O$, MS (ES+) m/z: 736.1 (M+H)+.

Example 22: Synthesis of Compound 22

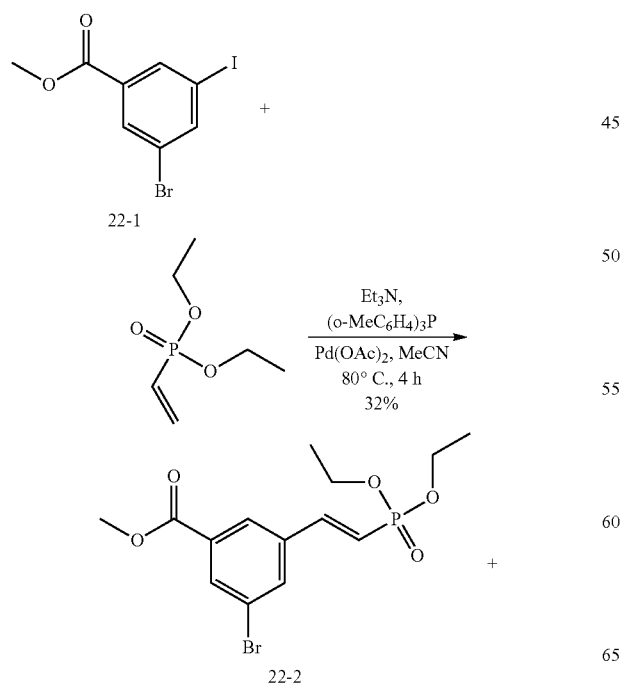

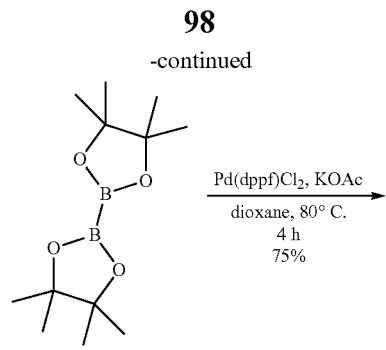

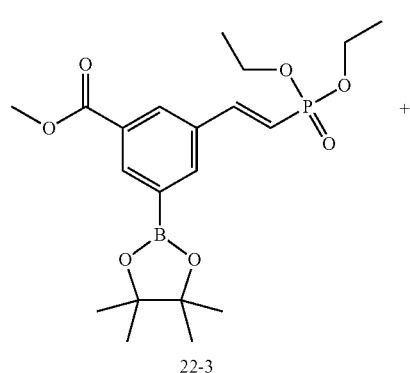

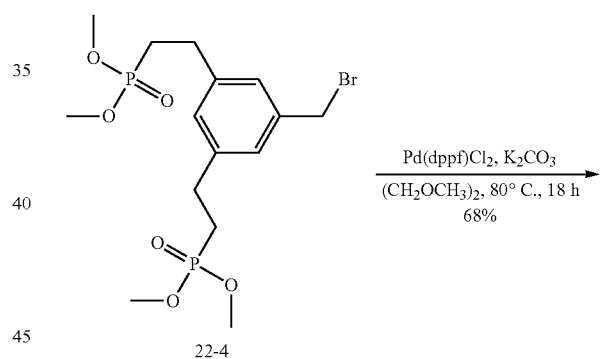

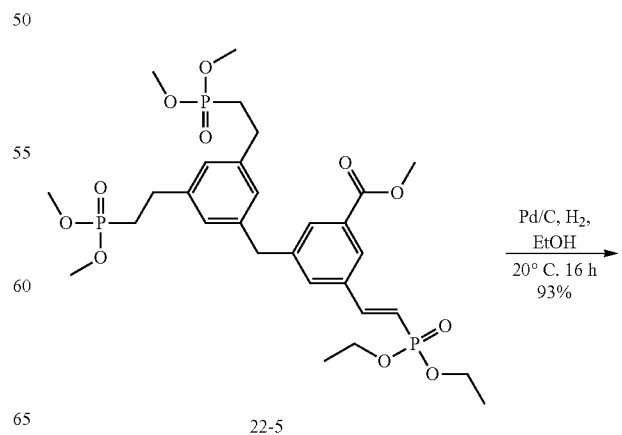

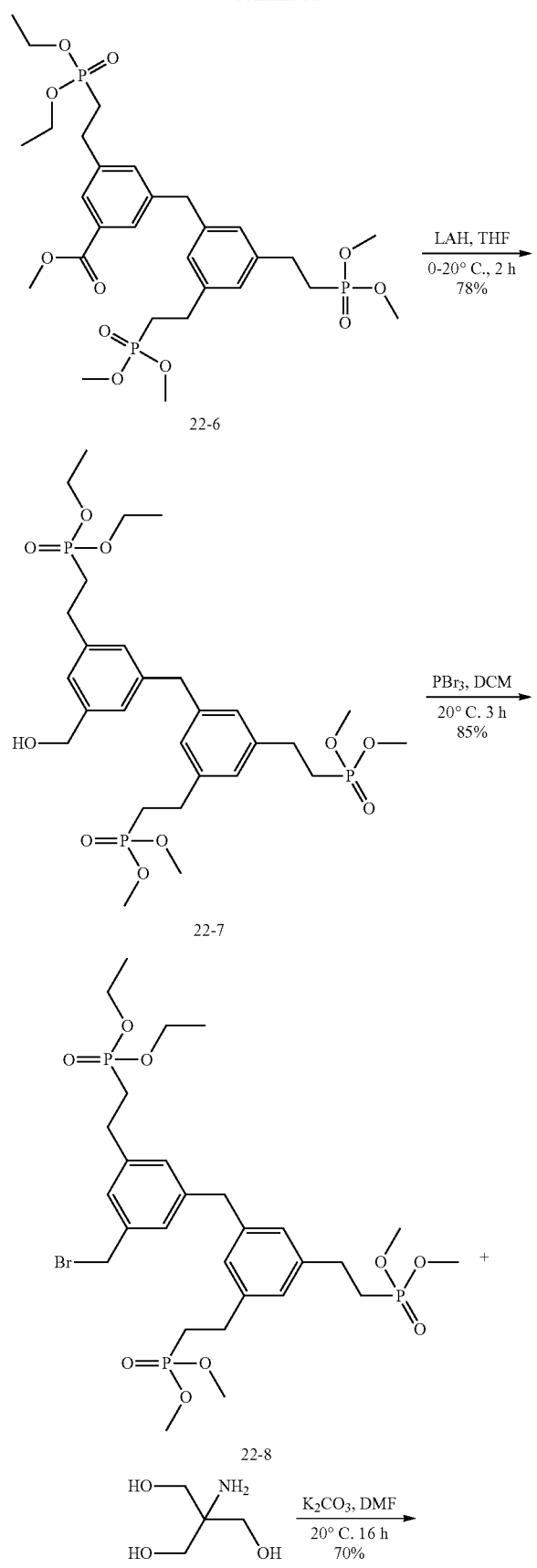
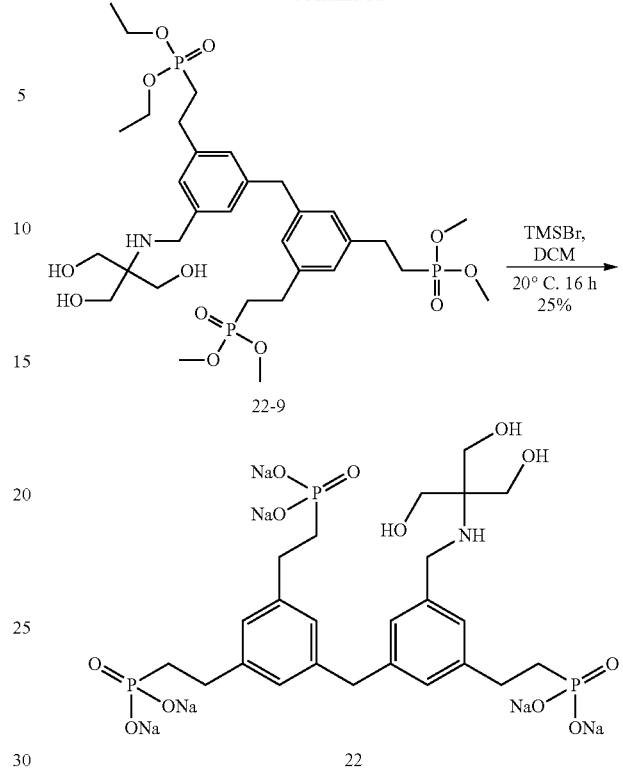

Step (1): To a 250 mL round flask, was added, 22-1 (6.82 g, 20.0 mmol), diethyl vinyl-phosphate (3.28 g, 20.0 mmol), TEA (4.04 g, 40 mmol), tris-(o-methyl phenyl)-phosphine (608 mg, 2.0 mmol), Pd (OAc)$_2$ (223 mg, 1.0 mmol), and 100 mL acetonitrile. The mixtures was stirred for 16 hrs under N$_2$ atmosphere. The mixture was filtrated, and concentrated to produce a residue which was purified by flash column chromatography to give 22-2, 2.41 g, with 32% yield as a viscous liquid: C$_{14}$H$_{18}$BrO$_5$P, MS (ES+) m/z: 399.0 (M+Na)$^+$.

Step (2): To a 100 mL round flask, was added 22-2 (2.2 g, 5.83 mmol), 4,4,4',4',5,5,5',5'-octamethyl-2,2'-bi(1,3,2-dioxaborolane) (2.22 g, 8.75 mmol), KOAc (1.72 g, 17.5 mmol), Pd(dppf)Cl$_2$ (213 mg, 0.29 mmol), and 40 mL 1,4-dioxane. The mixture was stirred for 6 hrs at 85° C. under nitrogen, and then was filtrated, concentrated to give a residue. The residue was purified by flash column chromatography to give 22-3, 1.86 g, with 75% yield: C$_{20}$H$_{30}$BO$_7$P, MS (ES+) m/z: 447.2 (M+Na)$^+$.

Step (3): To a 100 mL round flask, was added 22-3 (1.7 g, 4.01 mmol), 22-4 (1.95 g, 4.4 mmol), K$_2$CO$_3$ (1.11 g, 8.02 mmol), Pd(dppf)Cl$_2$ (293 mg, 0.40 mmol), and 30 mL glycol dimethyl ether. The reaction mixture was stirred for 18 hrs at 80° C. under nitrogen atmosphere. And the mixture was filtrated, and concentrated. The resulted residue was purified by flash column chromatography to give 22-5, 1.8 g, with 68% yield: C$_{29}$H$_{43}$O$_{11}$P$_3$, MS (ES+) m/z: 683.2 (M+Na)$^+$.

Step (4): To a 100 mL round flask, was added 22-5 (1.8 g, 2.72 mmol), 180 mg 10% Pd/C, and 30 mL ethanol. The reaction mixture was stirred for 16 hrs at 20° C. under nitrogen atmosphere. And the mixture was filtrated, and concentrated. The resulted residue was desired compound 22-6, 1.67 g, with 93% yield: $C_{29}H_{43}O_{11}P_3$, MS (ES+) m/z: 685.2 (M+H)$^+$.

Step (5): Compound 22-6 (1.67 g, 2.53 mmol) was dissolved in 30 mL THF in a 100 mL three-neck flask. The solution was cooled to 0° C., and was added dropwise 1 M LiAlH$_4$ (5.1 mL, 5.1 mmol). And the reaction was stirred over 2 hrs at 0° C. 5 g of Na$_2$SO$_4$·10H$_2$O was added to the cold solution to quench the reaction. And the resulted mixture was filtrate. The residue was washed with DCM (2×50 mL). The organic solution was combined and dried over Na$_2$SO$_4$, and filtrated, and concentrated. The produced residue was purified by flash chromatography to give compound 22-7, 1.22 g, with 76% yield as a sticky liquid: $C_{28}H_{45}O_{10}P_3$, MS (ES+) m/z: 635.2 (M+H)$^+$.

Step (6): To a 50 mL three-neck round flask, was added, 22-7 (1.22 g, 1.92 mmol), and 10 mL anhydrous dichloromethane. Under ice-water bath, the PBr3 (1.04 g, 3.84 mmol) was added at 0° C. The mixture was stirred for 3 hrs at 0-20° C., and then was poured into 50 g ice-water. The mixture was extracted with DCM (3×50 mL). The combined organic phase was washed with 100 mL brine. The organic layer was dried over Na$_2$SO$_4$, and filtrated, and concentrated. The viscous residue was identified as 22-8, 1.14 g, 85% yield: $C_{28}H_{44}BrO_9P_3$, MS (ES+) m/z: 697.2 (M+H)$^+$.

Step (7): Refer to step (1) of Example 8, to obtain 22-9, 842 mg, 70% yield, as a colorless liquid: $C_{32}H_{54}NO_{12}P_3$, MS (ES+) m/z: 738.3 (M+H)$^+$.

Step (8): Refer to step (2) of Example 8, to obtain Compound 22, 221 mg, 25% yield, as a while solid: $C_{24}H_{32}NNa_6O_{12}P_3 \cdot xH_2O$, MS (ES+) m/z: 626.2 (M+H)$^+$.

Example 23 Pharmacodynamic Test

The compounds in present invention are used to test the antitumor activity in Hep3B2.1-7-Luc orthotopic xenograft tumor model 1. Methods
    (1) Culture cells: The tumor cell Hep3B2.1-7-Luc were cultured in culture medium; culture conditions: 37° C., 5% CO$_2$.
    (2) Inoculate cells: The cells at the exponential growth phase and in good state were taken, and an appropriate amount of pancreatin for cell dissociation was added thereto, the cells were collected for centrifugation, and the supernatant was discarded. The cells were resuspended with the culture solution containing serum, then counted, and the cell suspensions were taken and inoculated in a 96-hole plate at 3000/hole, 90 μL/hole. The culture plate was transferred into a constant temperature CO$_2$ incubator, and cultured under the conditions of 37° C., 5% CO$_2$ and saturated humidity for 24 h.
2. Animal: BALB/c nude mice, female, 6-8 weeks old, body weight 18-22 g. Tumor inoculation: A 25 uL cell suspension of 1.25×10^6 Hep3B2.1-7-luc cells was orthotopically transplanted to left hepatic lobule of each mouse. The wound was sutured with stylolite. After 7 days of transportation, the mice was imaged with small animal imager IVIS Lumina XR, the mice with suitable signal intensity were selected to the pharmacological experiment, and each group included 10 animals.
3. Operation procedure of animal imaging
    1) Weigh a suitable amount of luciferin, prepare a concentration of 15 mg/mL with DPBS, use 0.2 um filter membrane to filtration sterilization, store in dark place at −20° C.
    2) Use a syringe of 25×⅝", 10 ul/g by mouse weight, each mouse to inject 150 mg luciferin/kg, i.e., 0.2 mL was injected to a 20 g mouse.
    3) After 10-12 minutes, anesthesia with isoflurane.
    4) Place the mouse to the imaging system box, abdomen upwards, to detect the tumor cells.
    5) The time horizon of time of exposure is one second to one minute. The imaging results is processed by image software, show as number of photons/second, imaging once a week, the last imaging to be done right before the experiment is finished.
4. Experiment Index: experiment index is to investigate if the tumor growth is inhibited, delayed or cured. Once a week via IVIS Lumina XR to image the mouse, to monitor the status of tumor growth. The tumor signal is counted on the number of exposure protons/second.
5. Data analysis: take the compound 7 of Example 7 for example, the result show as FIG. 1. Compound 7 of Example 7 possessed obvious inhibition of tumor proliferation.

Figure 2:
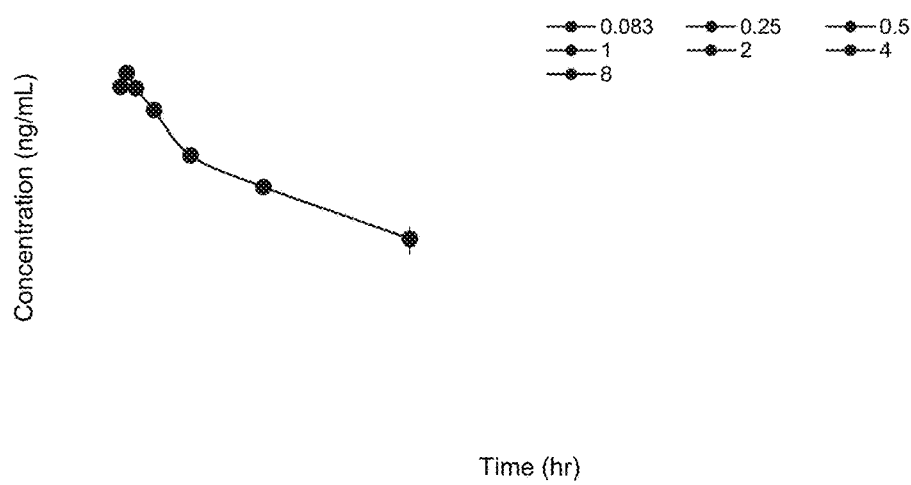
FIG. 2 is the Drug-Time graph of BALB\c nude mice ip injection of Example 8 compound of the present invention via method of Example 25 of the present invention.

The pharmacokinetics of Compound 7 of Example 7 show as FIGS. 2 and 3, and below Table 1.

TABLE 1

| BALB/c nude mice ip—Blood Concentration and parameter | | | | | | |
|---|---|---|---|---|---|---|
| PK parameters | Unit | Mouse 1# | Mouse 2# | Mouse 3# | Mean (ng/mL) | SD | CV (%) |
| $T_{max}$ | hr | 0.250 | 0.250 | 0.250 | 0.250 | 0.00 | 0.00 |
| $C_{max}$ | ng/mL | 17600 | 19900 | 17900 | 18467 | 1250 | 6.77 |
| $t_{1/2}$ | hr | 1.73 | 2.40 | 2.77 | 2.30 | 0.525 | 22.8 |
| $AUC_{last}$ | hr * ng/mL | 26280 | 26280 | 25270 | 25943 | 583 | 2.25 |
| $AUC_{INF}$ | hr * ng/mL | 27030 | 27956 | 27469 | 27485 | 463 | 1.68 |

Figure 3:
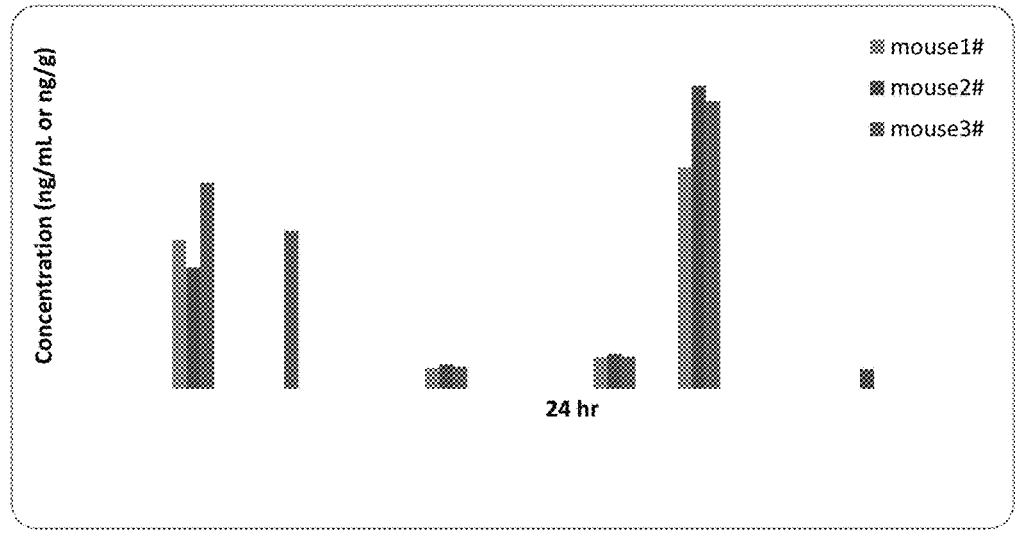
FIG. 3 is the histograph of drug concentration distributed in organs and tissue after 24 hours ip injection of Example 8 compound of the invention via method of Example 25 of the present invention.

From FIG. 3, BALB/c nude mice was treated with Compound 7 of Example 7 via i.p., after 24 hours, the drug compound is mainly located in liver, kidney, lung, intestine, spleen, prostate, pancreat and on. It hinted the compounds of present invention are particularly suitable to treating liver cancer, kidney cancer, prostate cancer, lung cancer, colon cancer, pancreat cancer and so on.

The above embodiments only express the modes of execution of the invention, they are described more specifically and in details, but they can't be understood as the limitation to the scope of the patent of the invention. It shall be indicated that for those skilled in the art, without separating from the idea of the invention, several transformations and improvements can also be obtained, and all these belong to the protective scope of the invention. Therefore, the protective scope for the patent of the invention shall be subject to the claims attached.

What is claimed is:

1. A compound with a formula (II),

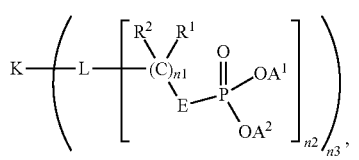
(II)

or a tautomer, mesomer, racemate, enantiomer, and diastereoisomer thereof, or a mixture form thereof, or a pharmaceutically acceptable salt thereof, wherein L is selected from a group consisting of C1-C10 alkyl, cycloalkyl, cycloalkylalkyl, alkylcycloalkyl, aryl, arylalkyl, alkylaryl, heteroaryl, heteroarylalkyl, alkylheteroaryl, alkenyl, alkynyl, a C3-C15 linear or branched chain containing an O, or S atom, a linear or branched chain consisting of repeating units of C1-C15 linear or branched chains containing O, or S atoms, bisaryl, bisheteroaryl, aryl-heteroaryl group or heteroaryl-aryl group, and bisaryl and bisheteroaryl linked by O, S or

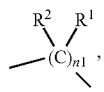

wherein the alkyl, the cycloalkyl, the heterocyclyl, the aryl or the heteroaryl may be each independently substituted by one or more substituents selected from a group consisting of hydroxyl, halogen, alkyl, alkoxyl, cycloalkyl, heterocyclyl, aryl, and heteroaryl;

K is selected from

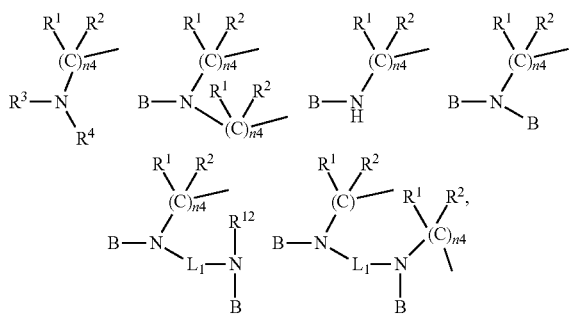

with B selected from a group consisting of

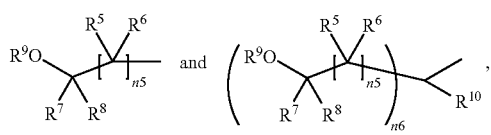

$R^1$ and $R^2$ are each independently selected from a group consisting of hydrogen, alkyl, cycloalkyl, hydroxyalkane, alkoxylalkyl, alkoxylcycloalkyl, cycloalkylalkyl, alkylcycloalkyl, alkenyl, alkynyl, amino, hydroxyl, mercapto, carboxyl, alkoxyl, cycloalkoxyl, haloalkyl, cyano, thioalkyl, sulfo, sulfonyl, sulfinyl, phosphate, alkylphosphonate, arylphosphate, and arylphosphonate, wherein the alkyl, the cycloalkyl, the heterocyclyl, the aryl, or the heteroaryl may be each independently substituted by one or more substituents selected from a group consisting of hydroxyl, halogen, alkyl, alkoxyl, cycloalkyl, heterocyclyl, aryl, and heteroaryl, or may be null;

$R^3$ and $R^4$ are each independently selected from a group consisting of hydrogen, alkyl, cycloalkyl, cycloalkylalkyl, alkylcycloalkyl, aryl, arylalkyl, alkylaryl, heteroaryl, heteroarylalkyl, alkylheteroaryl, heterocyclyl, heterocyclylalkyl, alkylheterocyclyl, alkenylalkyl, and alkynylalkyl, wherein the alkyl, the cycloalkyl, the cycloalkylalkyl, the alkylcycloalkyl, the aryl, the arylalkyl, the alkylaryl, the heteroaryl, the heteroarylalkyl, the alkylheteroaryl, the heterocyclyl, the heterocyclylalkyl, the alkylheterocyclyl, the alkenylalkyl, or the alkynylalkyl is not substituted or is substituted by one or more substituents, each of which is selected from a group consisting of alkyl, cycloalkyl, cycloalkylalkyl, alkylcycloalkyl, aryl, arylalkyl, alkylaryl, heteroaryl, heteroarylalkyl, alkylheteroaryl, heterocyclyl, heterocyclylalkyl, alkylheterocyclyl, alkenyl, alkynyl, amino, hydroxyl, mercapto, carboxyl, alkoxyl, cycloalkoxyl, haloalkyl, alkoxycarbonyl, acyloxy, amido, ureido, alkylsulfonyl, arylsulfonyl, haloalkyl, halogen, cyano, nitro, nitroso, thiocyano, isothiocyano, thioalkyl, sulfo, phosphate, phosphonate, alkylphosphate, alkylphosphonate, arylphosphate, and arylphosphonate;

or $R^3$ and $R^4$ together with a nitrogen atom for linking $R^3$ and $R^4$ form heterocyclyl, which is a monocyclic ring, a bicyclic ring or a tricyclic ring, or a fused ring, a bridge ring or a spiro-ring, wherein the heterocyclyl comprises at least one N atom or one, two or three heteroatoms optionally selected from N, S and O, and is not substituted or is optionally substituted by one or more substituents, each of which is independently selected from a group consisting of alkyl, cycloalkyl, cycloalkylalkyl, alkylcycloalkyl, aryl, arylalkyl, alkylaryl, heteroaryl, heteroarylalkyl, alkylheteroaryl, heterocyclyl, heterocyclylalkyl, alkylheterocyclyl, alkenyl, alkynyl, amino, hydroxyl, mercapto, carboxyl, alkoxyl, cycloalkoxyl, haloalkyl, alkoxycarbonyl, acyloxy, amido, ureido, alkylsulfonyl, arylsulfonyl, haloalkyl, halogen, cyano, nitro, nitroso, thiocyano, isothiocyano, thioalkyl, sulfo, phosphate, phosphonate, alkylphosphate, alkylphosphonate, arylphosphate, and arylphosphonate, which are used as a substituent alone or in a free combination thereof, $A^1$ and $A^2$ are each independently selected from a group consisting of Li, Na, K, Cs, and a corresponding positive ion thereof, or $A^1$ and $A^2$ form Ca, Mg, Al, Sc, Ti, Cr, Co, Fe, Ni, Cu, Zn, Cd, Hg, and a corresponding positive ion thereof, collectively;

E is selected from a group consisting of oxygen and $C(R^1R^2)$;

$R^5$ and $R^6$ are each independently selected from a group consisting of a hydrogen atom, halogen, alkyl, alkoxyalkyl, cycloalkyl, alkoxycycloalkyl, hydroxyalkyl, hydroxycycloalkyl, heterocyclyl, aryl and heteroaryl, wherein the alkyl, the cycloalkyl, the heterocyclyl, the aryl or the heteroaryl may be each independently substituted by one or more substituents selected from a group consisting of hydroxyl, halogen, alkyl, alkoxyl, cycloalkyl, heterocyclyl, aryl, and heteroaryl; or $R^5$ and $R^6$ may form a 3-membered to 8-membered ring, which may contain 1 to 2 heteroatoms of O, N and/or S;

R⁷ and R⁸ are each independently selected from a group consisting of a hydrogen atom, alkyl, hydroxyalkyl, cycloalkyl, alkoxyalkyl, alkoxycycloalkyl, heterocyclyl, aryl and heteroaryl, wherein the alkyl, the cycloalkyl, the heterocyclyl, the aryl or the heteroaryl may be each independently substituted by one or more substituents selected from a group consisting of hydroxyl, halogen, alkyl, alkoxy, cycloalkyl, heterocyclyl, aryl and heteroaryl;

R⁹ is hydrogen

R¹⁰ is selected from a group consisting of a hydrogen atom, halogen, alkane, cycloalkyl, heterocyclyl, aryl, and heteroaryl, or is null, wherein the alkane, the cycloalkyl, the heterocyclyl, the aryl, or the heteroaryl may be each independently substituted by one or more substituents selected from a group consisting of hydroxyl, halogen, alkyl, alkoxy, cycloalkyl, heterocyclyl, aryl, and heteroaryl;

n1 is selected from a group consisting of 0, 1, 2, 3, 4, 5, 6, 7, and 8;

n2 is selected from a group consisting of 1, 2, 3, 4, 5, and 6;

n3 is selected from a group consisting of 1, 2, and 3;

n4 is selected from a group consisting of 0, 1, 2, 3, and 4;

n5 is selected from a group consisting of 0, 1, 2, and 3; and n6 is selected from a group consisting of 1, 2, and 3.

2. The compound according to claim 1, wherein, the compound is a compound shown in a formula (II),

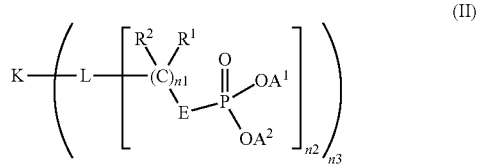

(II)

or a tautomer, mesomer, racemate, enantiomer, and diastereoisomer thereof, or a mixture form thereof, or a pharmaceutically acceptable salt thereof, or a prodrug molecule thereof, wherein L is selected from a group consisting of C1-C10 alkyl, cycloalkyl, cycloalkylalkyl, alkylcycloalkyl, aryl, arylalkyl, alkylaryl, heteroaryl, heteroarylalkyl, alkylheteroaryl, alkenyl, alkynyl, a C3-C15 linear or branched chain containing an O, or S atom, a linear or branched chain consisting of repeating units of C1-C15 linear or branched chains containing or O, or S atoms, bisaryl, bisheteroaryl, aryl-heteroaryl group or heteroaryl-aryl group, and bisaryl and bisheteroaryl linked by O, S or

wherein the alkyl, the cycloalkyl, the heterocyclyl, the aryl or the heteroaryl may be each independently substituted by one or more substituents selected from a group consisting of hydroxyl, halogen, alkyl, alkoxyl, cycloalkyl, heterocyclyl, aryl, and heteroaryl;

R¹ and R² are each independently selected from a group consisting of hydrogen, alkyl, cycloalkyl, hydroxyalkane, alkoxylalkyl, alkoxylcycloalkyl, cycloalkylalkyl, alkylcycloalkyl, alkenyl, alkynyl, amino, hydroxyl, mercapto, carboxyl, alkoxyl, cycloalkoxyl, haloalkyl, cyano, thioalkyl, sulfo, sulfonyl, sulfinyl, phosphate, alkylphosphonate, arylphosphate, and arylphosphonate, wherein the alkyl, the cycloalkyl, the heterocyclyl, the aryl, or the heteroaryl may be each independently substituted by one or more substituents selected from a group consisting of hydroxyl, halogen, alkyl, alkoxyl, cycloalkyl, heterocyclyl, aryl, and heteroaryl;

K is selected from a group consisting of

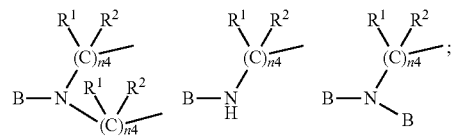

B is selected from a group consisting of

A¹ and A² are each independently selected from a group consisting of Li, Na, K, Cs, and a corresponding positive ion thereof, or A¹ and A² form Ca, Mg, Al, Sc, Ti, Cr, Co, Fe, Ni, Cu, Zn, Cd, Hg, and a corresponding positive ion thereof, collectively;

E is C(R¹R²);

R⁵ and R⁶ are each independently selected from a group consisting of a hydrogen atom, halogen, alkyl, alkoxyalkyl, cycloalkyl, alkoxycycloalkyl, heterocyclyl, aryl and heteroaryl, wherein the alkyl, the cycloalkyl, the heterocyclyl, the aryl or the heteroaryl may be each independently substituted by one or more substituents selected from a group consisting of hydroxyl, halogen, alkyl, alkoxyl, cycloalkyl, heterocyclyl, aryl, and heteroaryl; or R⁵ and R⁶ may form a 3-membered to 8-membered ring, which may contain 1 to 2 heteroatoms of O, N and/or S;

R⁷ and R⁸ are each independently selected from a group consisting of a hydrogen atom, alkyl, hydroxyalkyl, cycloalkyl, alkoxyalkyl, alkoxycycloalkyl, heterocyclyl, aryl and heteroaryl, wherein the alkyl, the cycloalkyl, the heterocyclyl, the aryl or the heteroaryl may be each independently substituted by one or more substituents selected from a group consisting of hydroxyl, halogen, alkyl, alkoxy, cycloalkyl, heterocyclyl, aryl and heteroaryl;

R⁹ is selected from a group consisting of a hydrogen atom, alkyl, cycloalkyl, heterocyclyl, aryl, and heteroaryl, wherein the alkyl, the cycloalkyl, the heterocyclyl, the aryl, or the heteroaryl may be each independently substituted by one or more substituents selected from a group consisting of hydroxyl, halogen, alkyl, alkoxy, cycloalkyl, heterocyclyl, aryl, and heteroaryl;

R¹⁰ is selected from a group consisting of a hydrogen atom, halogen, alkyl, cycloalkyl, heterocyclyl, aryl, and heteroaryl, or is null, wherein the alkyl, the cycloalkyl, the heterocyclyl, the aryl, or the heteroaryl may be each independently substituted by one or more substituents selected from a group consisting of hydroxyl, halogen, alkyl, alkoxy, cycloalkyl, heterocyclyl, aryl, and heteroaryl;

n1 is selected from a group consisting of 0, 1, 2, 3, 4, 5, 6, 7, and 8;

n2 is selected from a group consisting of 1, 2, 3, 4, 5, and 6;

n3 is selected from a group consisting of 1, 2, and 3;

n4 is selected from a group consisting of 0, 1, 2, 3, and 4;

n5 is selected from a group consisting of 0, 1, 2, and 3; and n6 is selected from a group consisting of 1, 2, and 3.

3. The compound according to claim 1, wherein the compound is a compound shown in a formula (II),

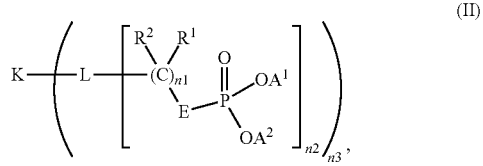

or a tautomer, mesomer, racemate, enantiomer, and diastereoisomer thereof, or a mixture form thereof, or a pharmaceutically acceptable salt thereof, or a prodrug molecule thereof, wherein K is

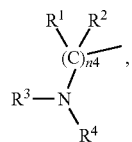

or E is an oxygen atom;

$R^3$ and $R^4$ are each independently selected from a group consisting of hydrogen, alkyl, cycloalkyl, cycloalkylalkyl, alkylcycloalkyl, aryl, arylalkyl, alkylaryl, heteroaryl, heteroarylalkyl, alkylheteroaryl, heterocyclyl, heterocyclylalkyl, alkylheterocyclyl, alkenylalkyl, and alkynylalkyl, wherein the alkyl, the cycloalkyl, the cycloalkylalkyl, the alkylcycloalkyl, the aryl, the arylalkyl, the alkylaryl, the heteroaryl, the heteroarylalkyl, the alkylheteroaryl, the heterocyclyl, the heterocyclylalkyl, the alkylheterocyclyl, the alkenylalkyl, or the alkynylalkyl is not substituted or is substituted by one or more substituents, each of which is selected from a group consisting of alkyl, cycloalkyl, cycloalkylalkyl, alkylcycloalkyl, aryl, arylalkyl, alkylaryl, heteroaryl, heteroarylalkyl, alkylheteroaryl, heterocyclyl, heterocyclylalkyl, alkylheterocyclyl, alkenyl, alkynyl, amino, hydroxyl, mercapto, carboxyl, alkoxyl, cycloalkoxyl, haloalkyl, alkoxycarbonyl, acyloxy, amido, ureido, alkylsulfonyl, arylsulfonyl, haloalkyl, halogen, cyano, nitro, nitroso, thiocyano, isothiocyano, thioalkyl, sulfo, phosphate, phosphonate, alkylphosphate, alkylphosphonate, arylphosphate, and arylphosphonate;

or $R^3$ and $R^4$ together with a nitrogen atom for linking $R^3$ and $R^4$ form heterocyclyl, which is a monocyclic ring, a bicyclic ring or a tricyclic ring, or a fused ring, a bridge ring or a spiro-ring, wherein the heterocyclyl comprises at least one N atom or one, two or three heteroatoms optionally selected from N, S and O, and is not substituted or is optionally substituted by one or more substituents, each of which is independently selected from a group consisting of alkyl, cycloalkyl, cycloalkylalkyl, alkylcycloalkyl, aryl, arylalkyl, alkylaryl, heteroaryl, heteroarylalkyl, alkylheteroaryl, heterocyclyl, heterocyclylalkyl, alkylheterocyclyl, alkenyl, alkynyl, amino, hydroxyl, mercapto, carboxyl, alkoxyl, cycloalkoxyl, haloalkyl, alkoxycarbonyl, acyloxy, amido, ureido, alkylsulfonyl, arylsulfonyl, haloalkyl, halogen, cyano, nitro, nitroso, thiocyano, isothiocyano, thioalkyl, sulfo, phosphate, phosphonate, alkylphosphate, alkylphosphonate, arylphosphate, and arylphosphonate, which are used as a substituent alone or in a free combination thereof.

4. The compound according to claim 1, wherein the compound is a compound shown in a formula (III),

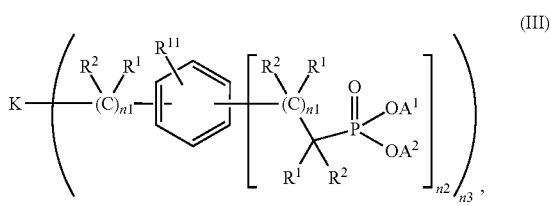

or a tautomer, mesomer, racemate, enantiomer, and diastereoisomer thereof, or a mixture form thereof, or a pharmaceutically acceptable salt thereof, or a prodrug molecule thereof, wherein $R^{11}$ is selected from a group consisting of hydrogen, halogen, C1-C6 alkyl, C3-C8 cycloalkyl, heterocyclyl, hydroxyl, alkoxyl, aryl and heteroaryl.

5. A compound selected from the following:

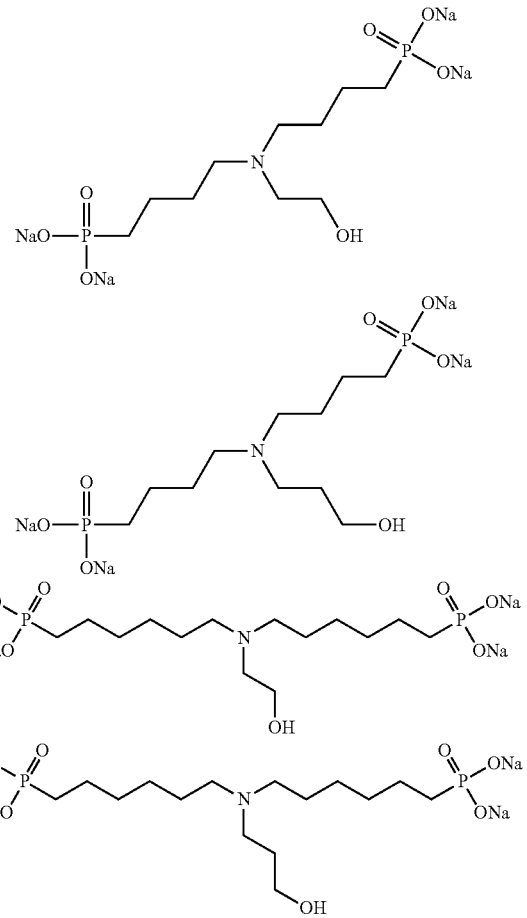

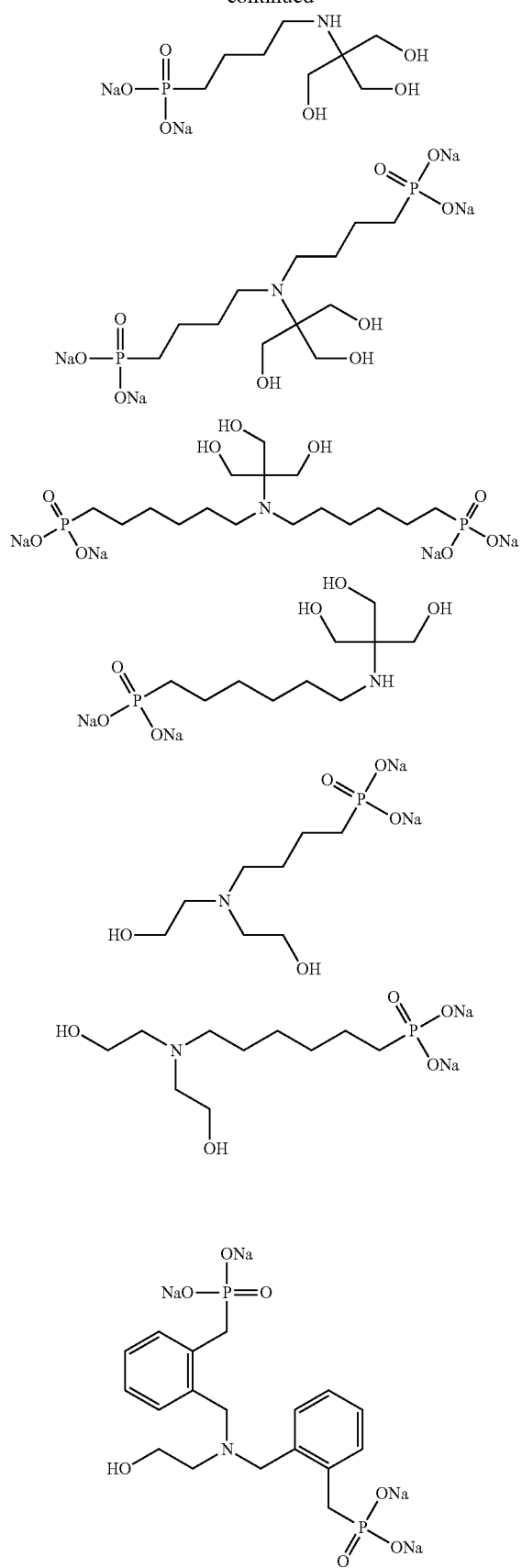
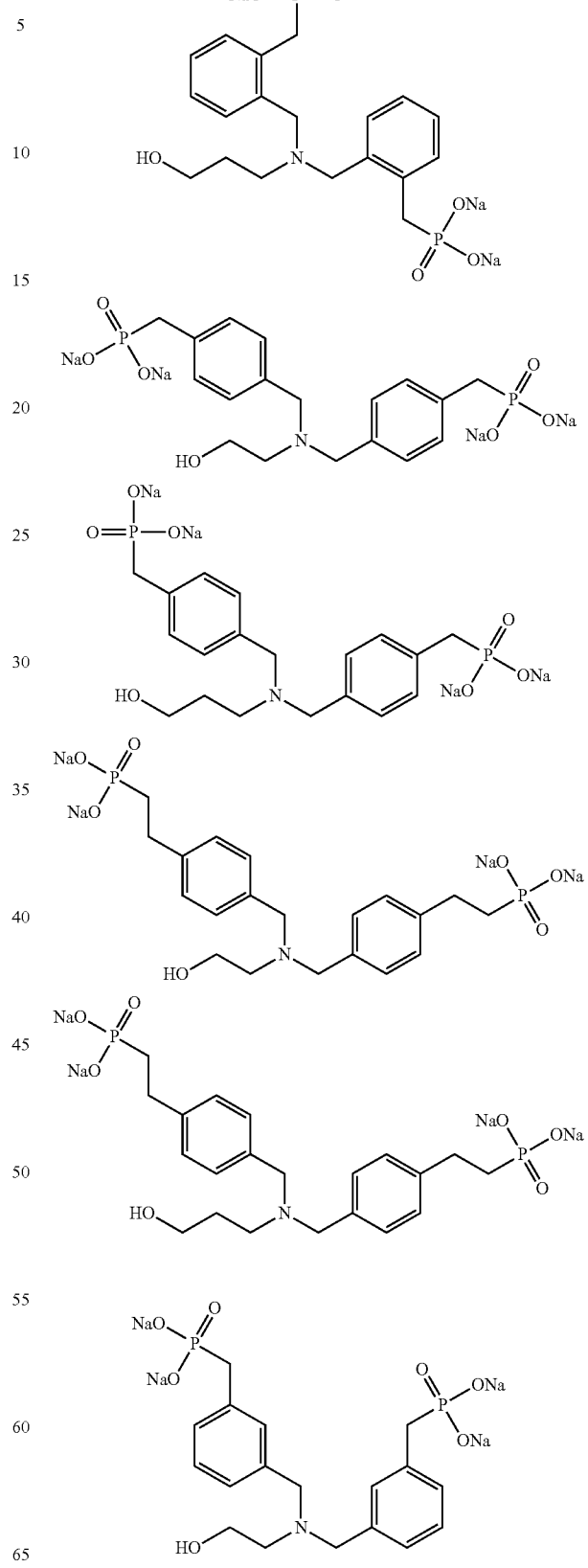

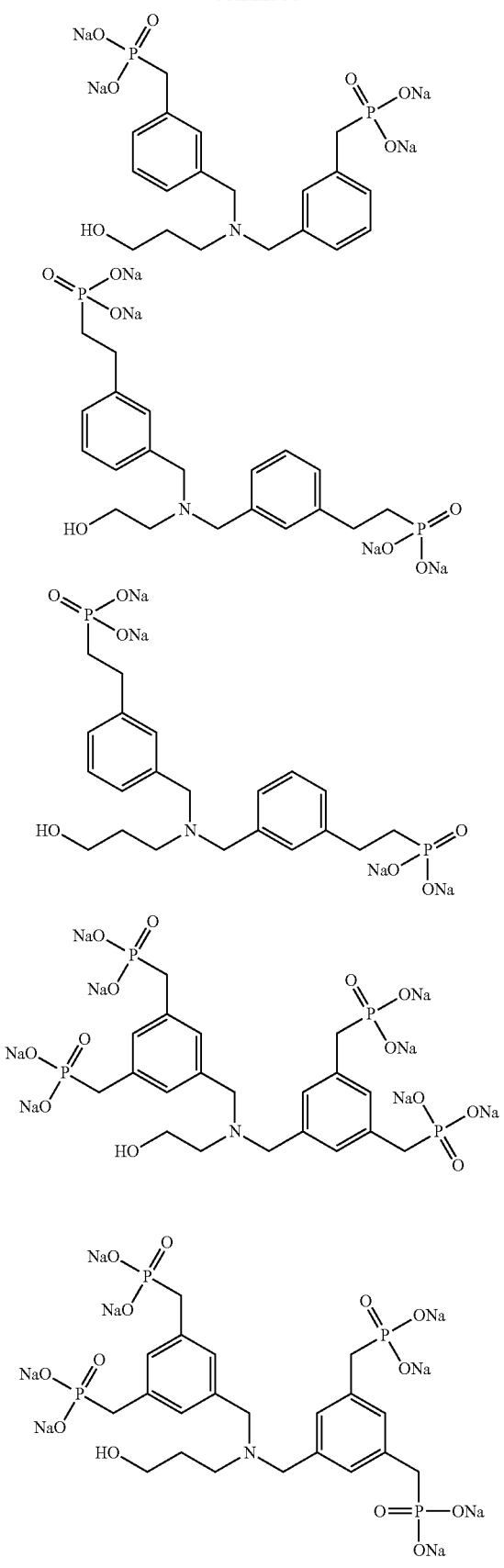
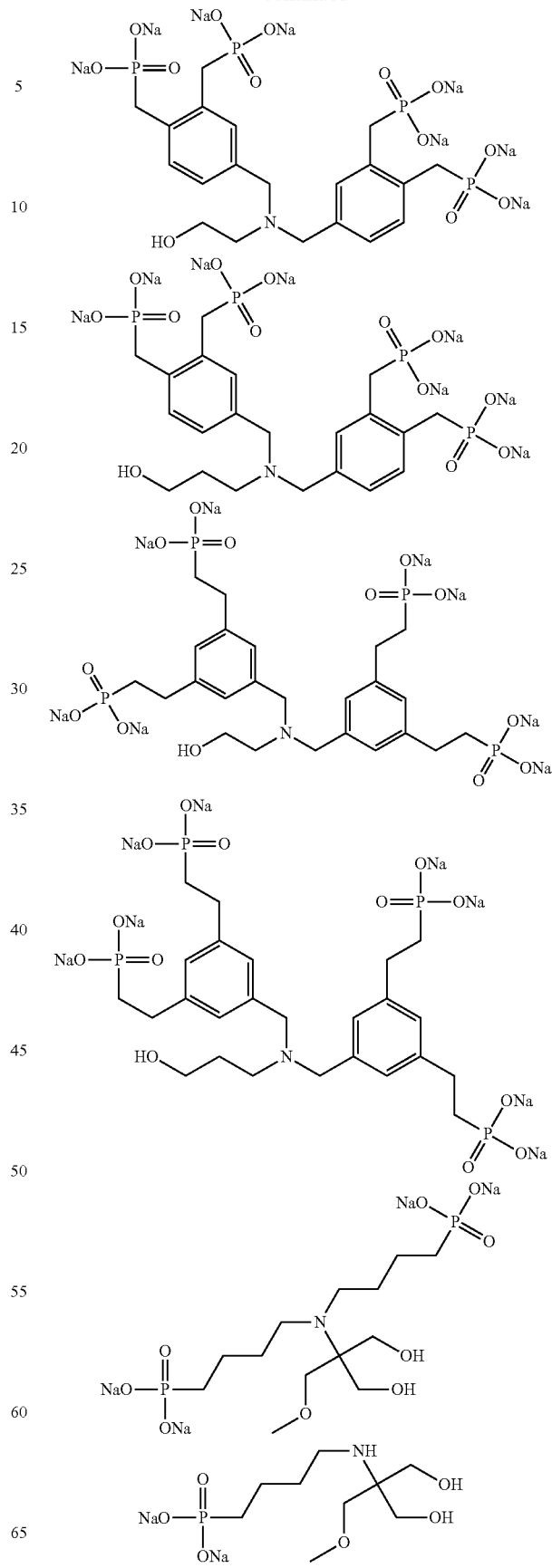

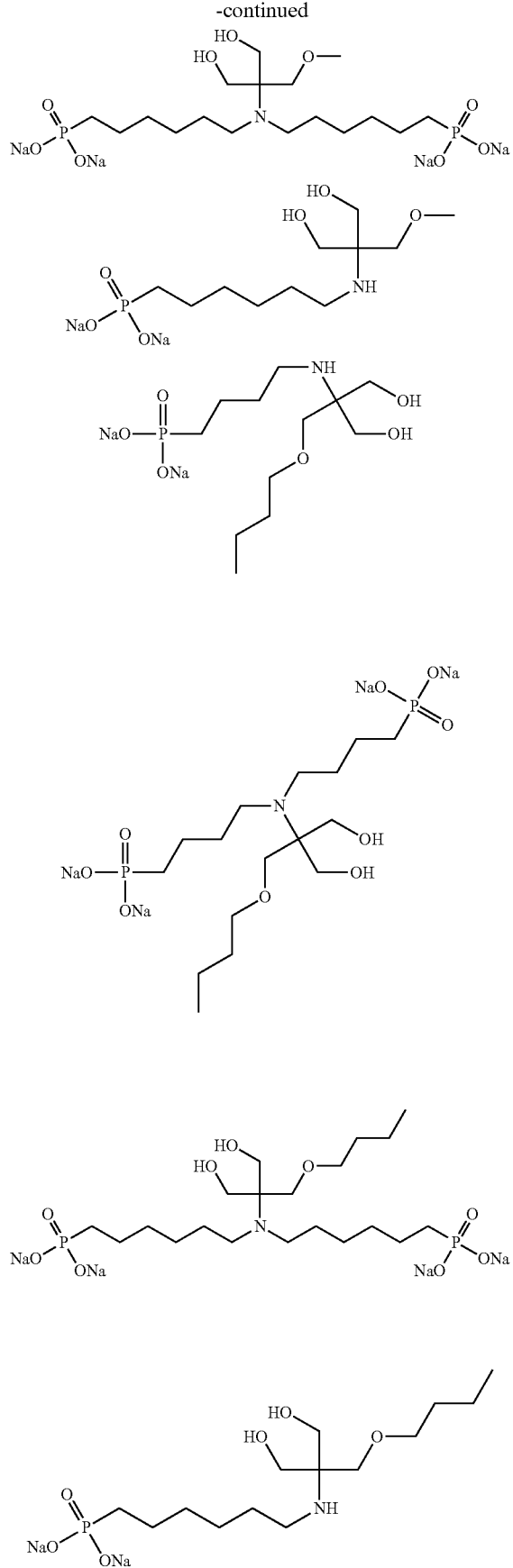
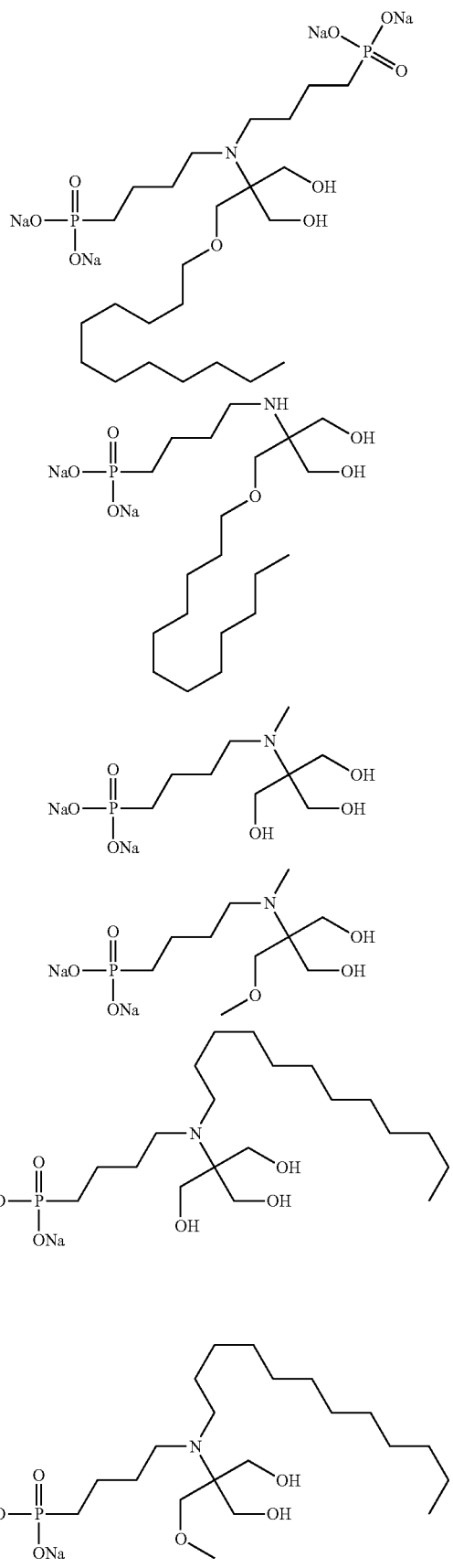

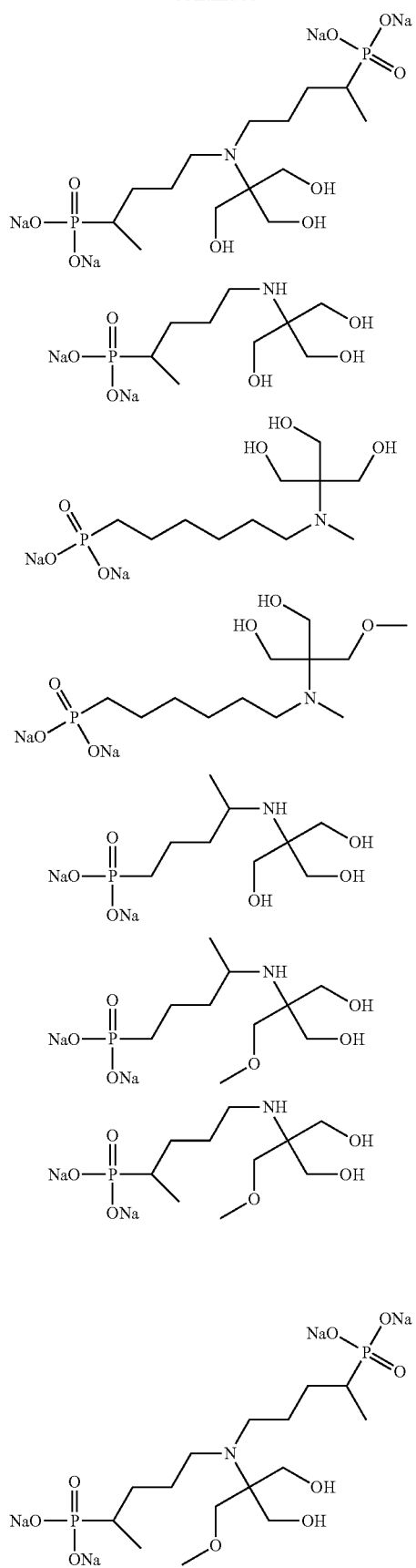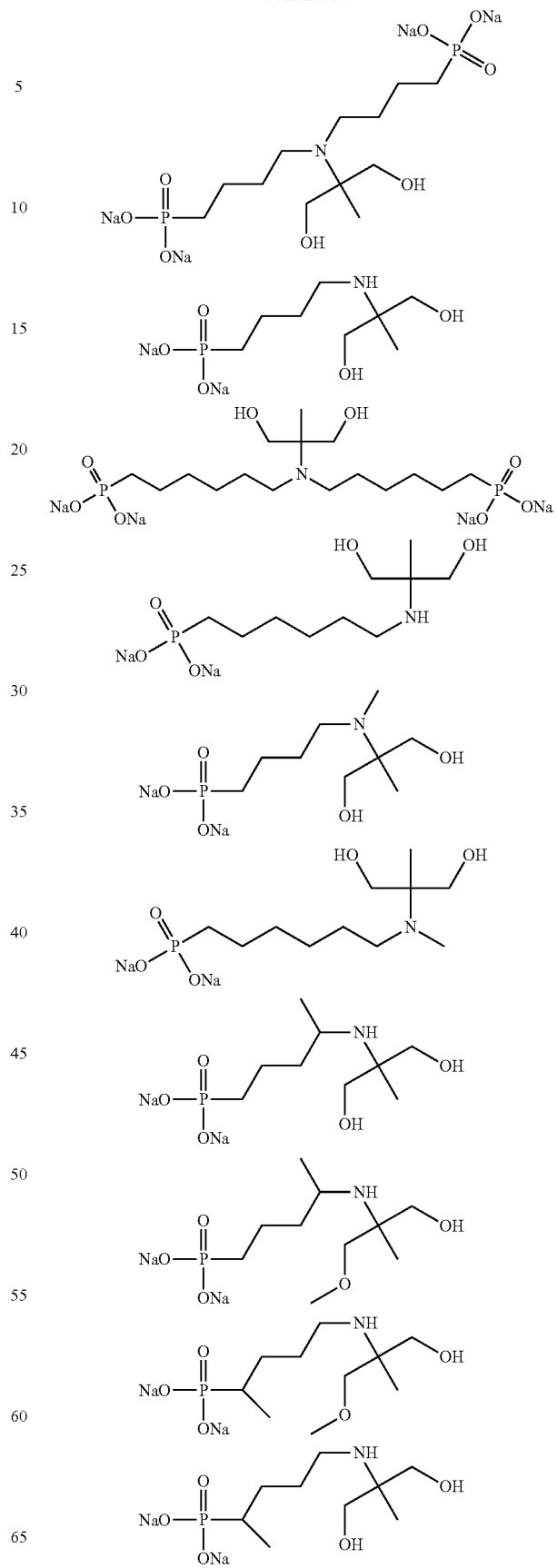

117
-continued
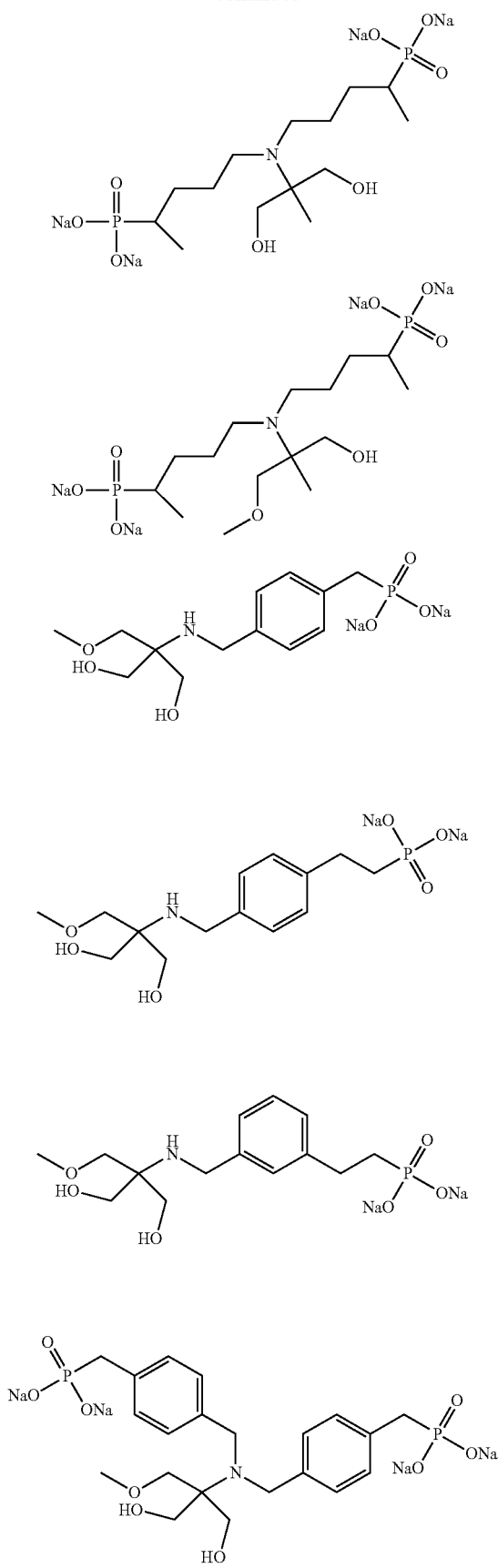
118
-continued
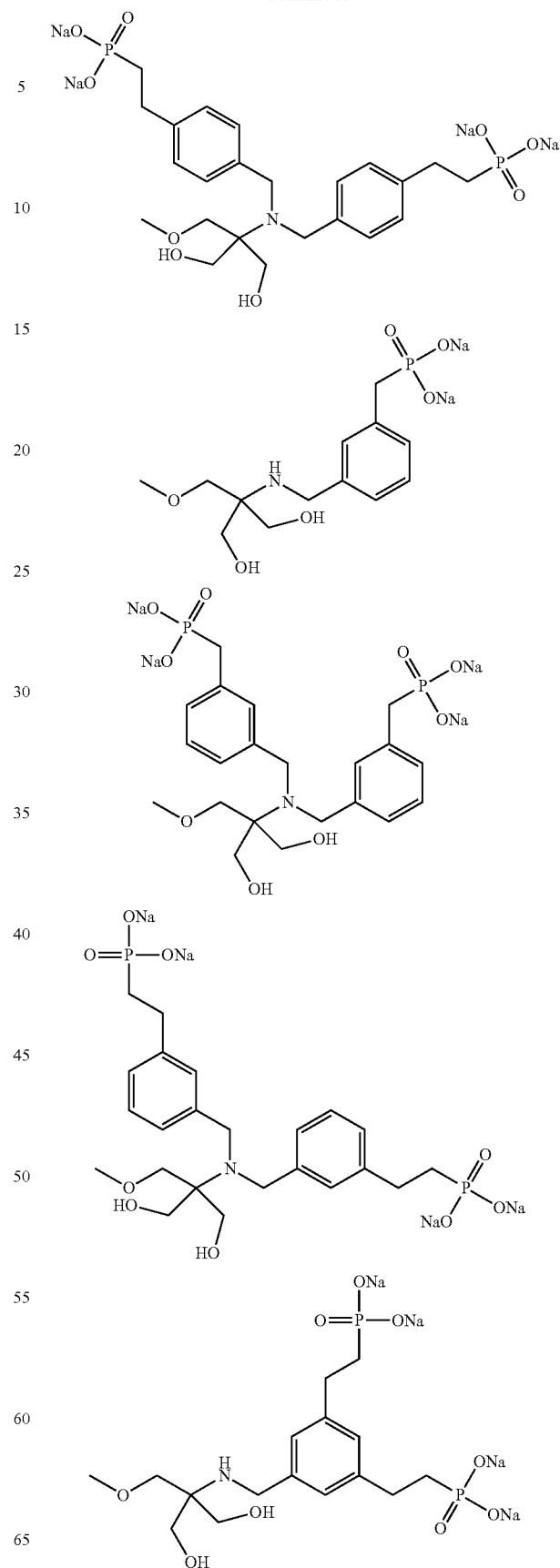

119
-continued
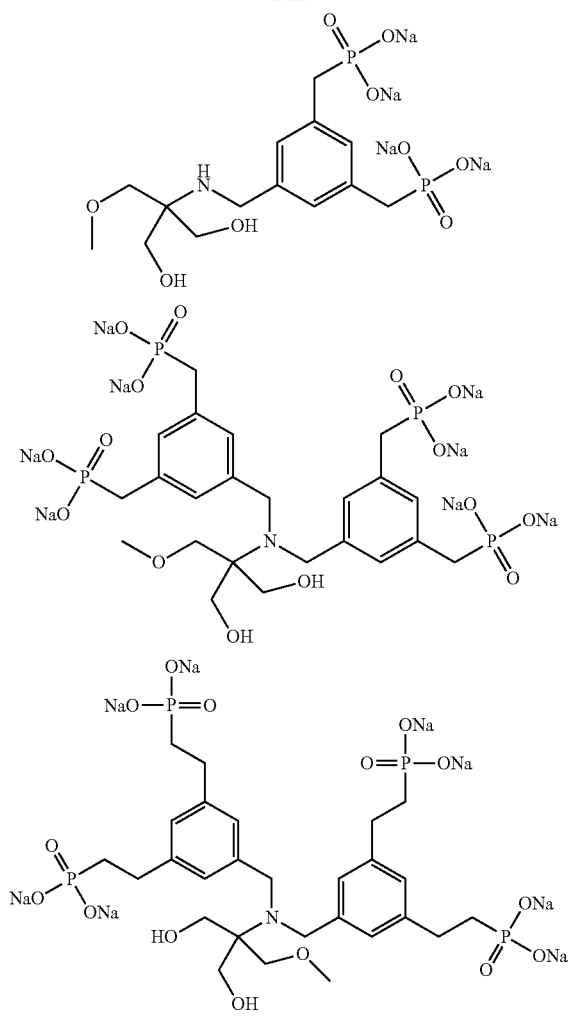
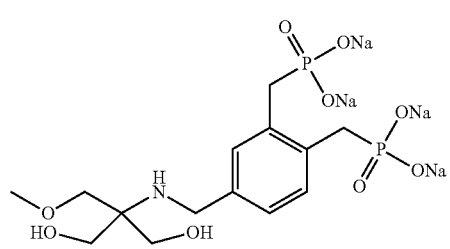
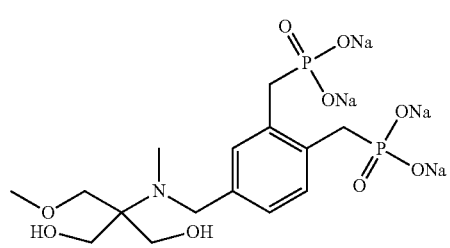
120
-continued
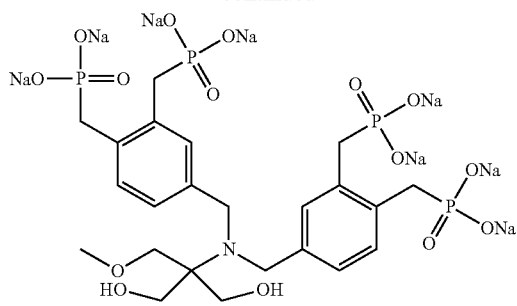
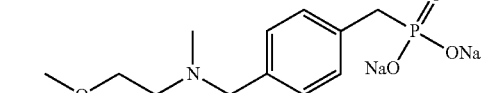
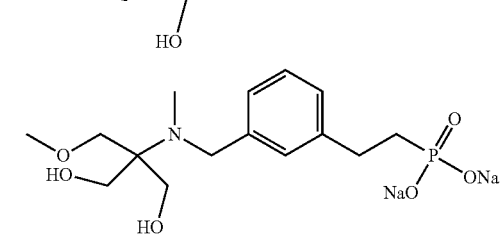
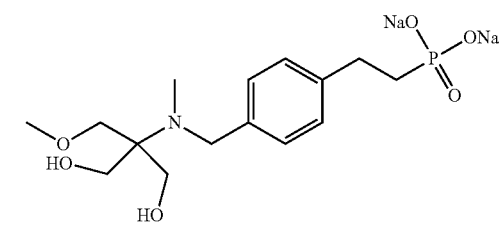
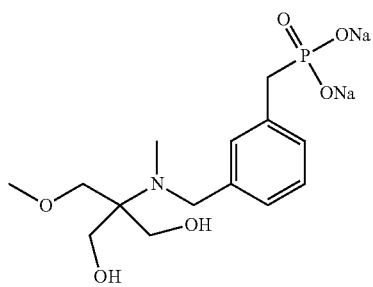
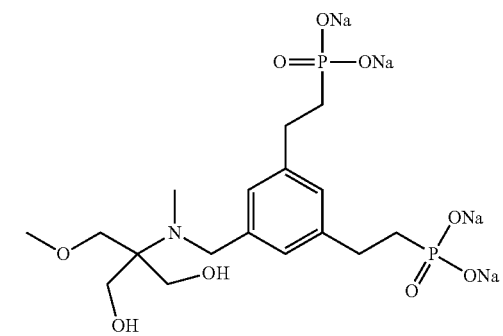

121
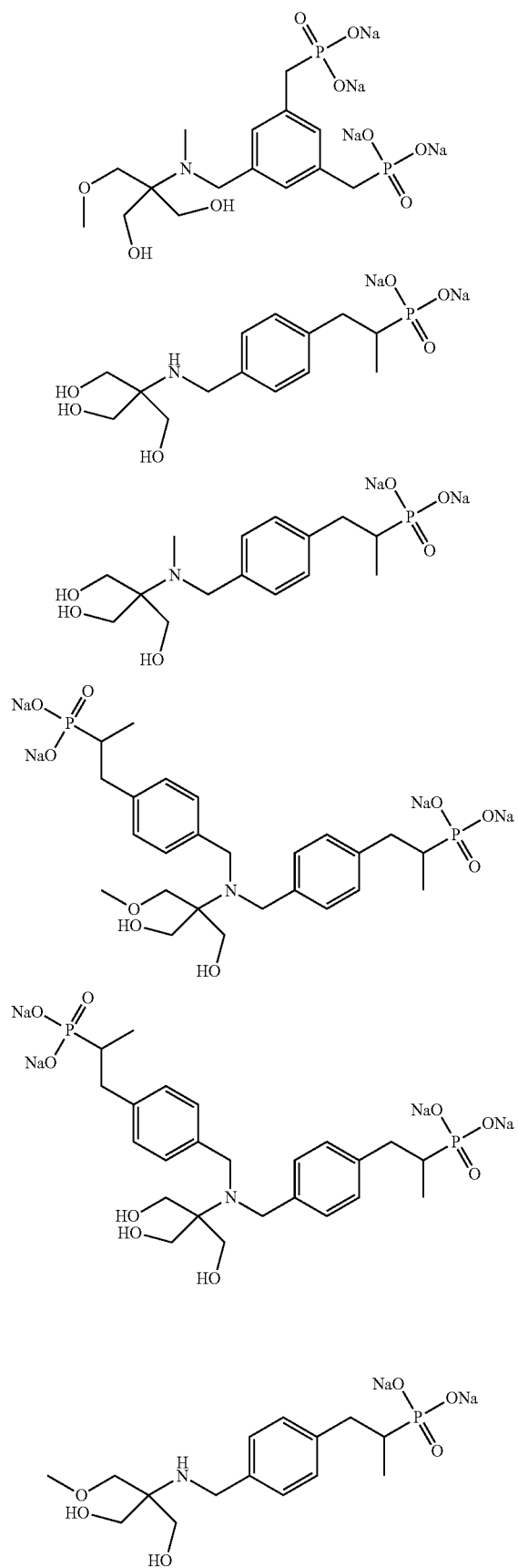
122
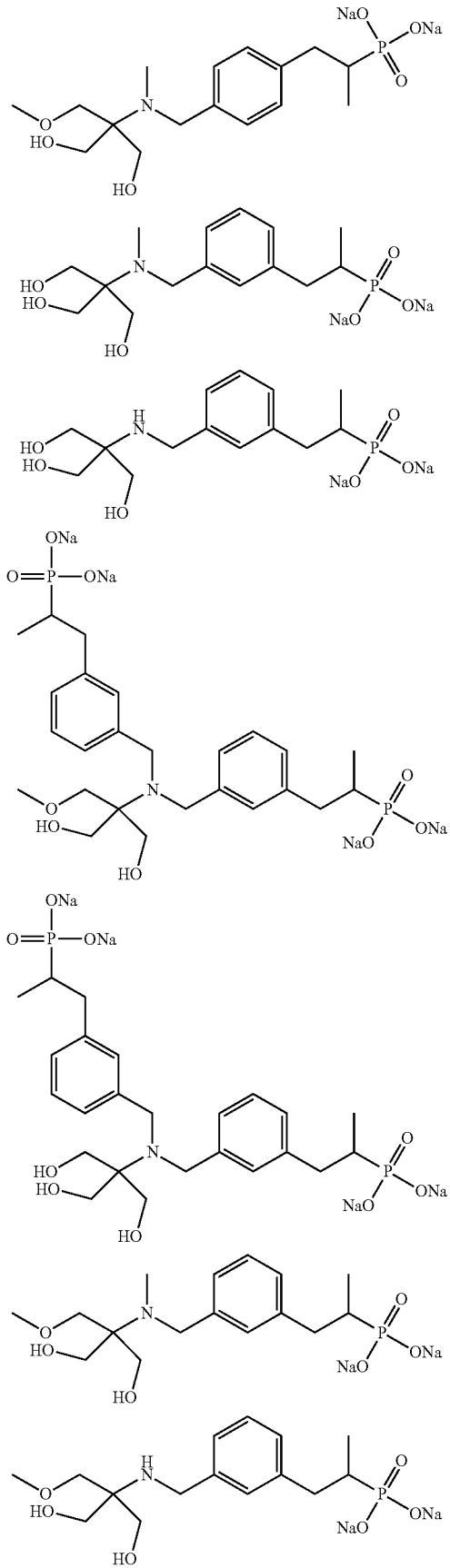

123
-continued
124
-continued
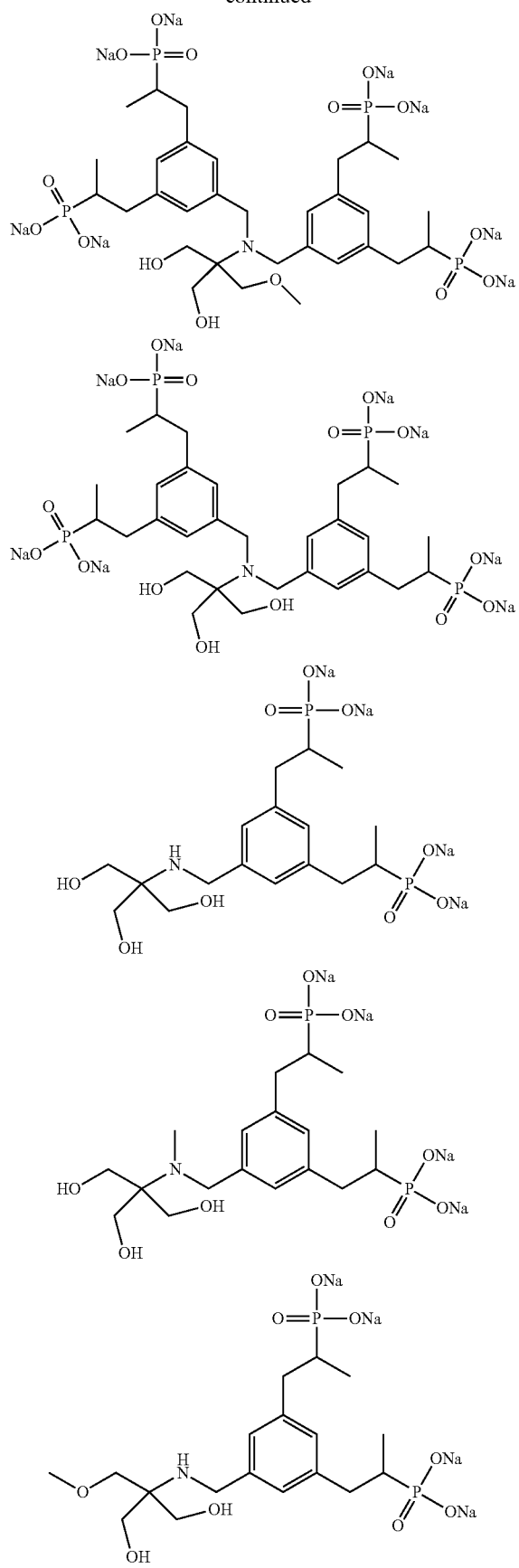

-continued
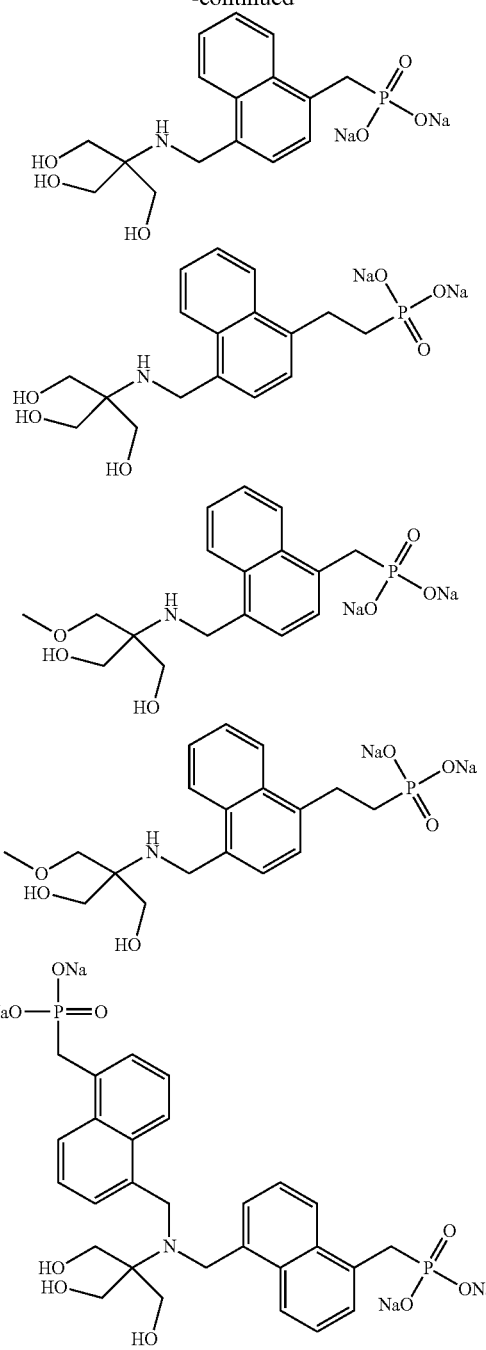
-continued
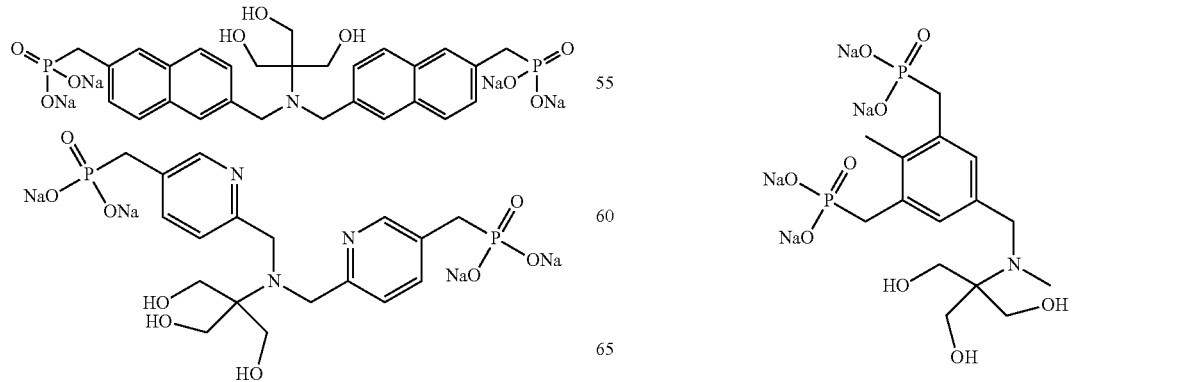

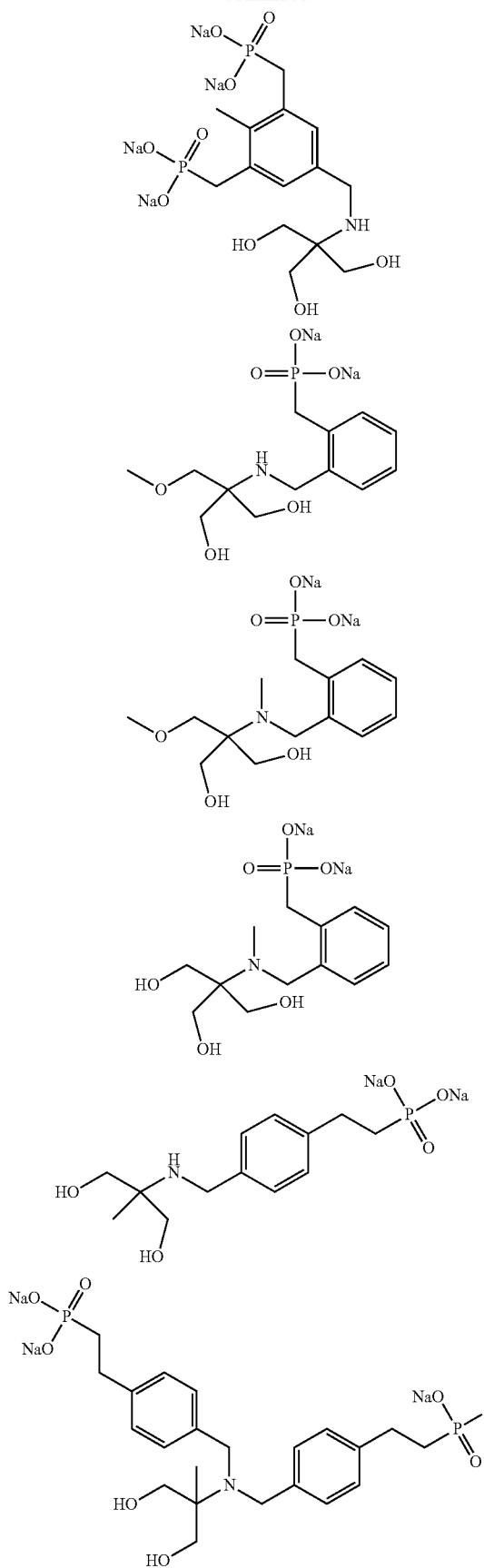
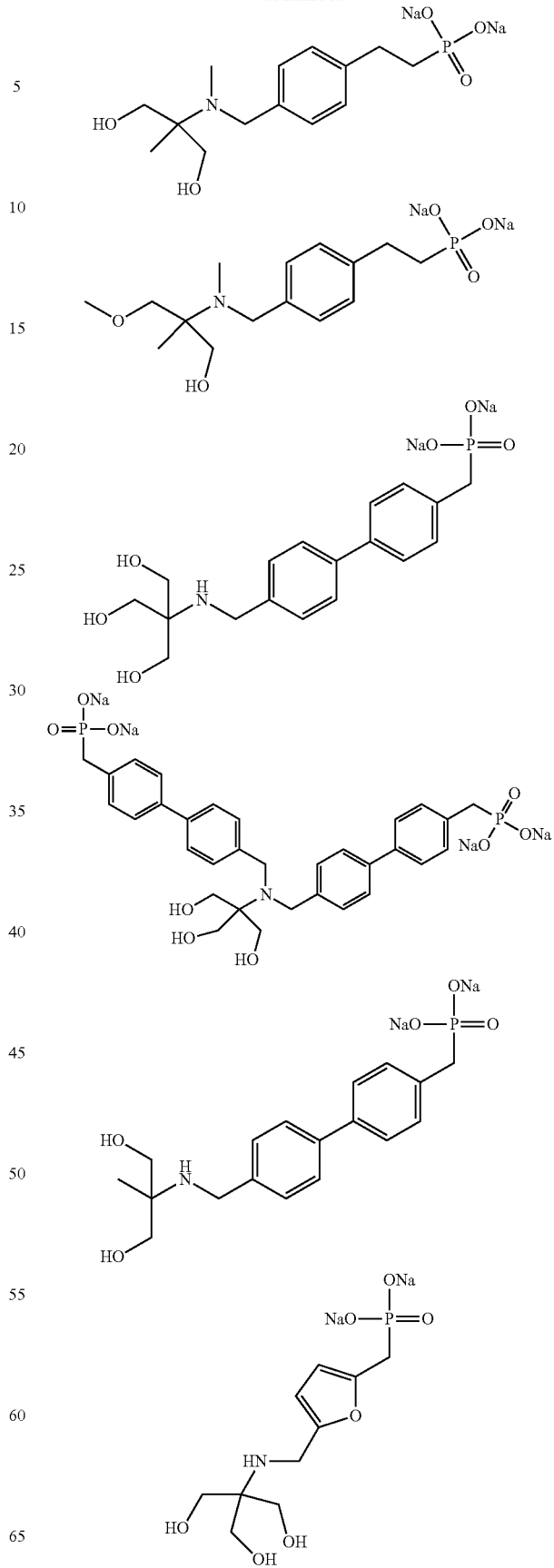

129
-continued
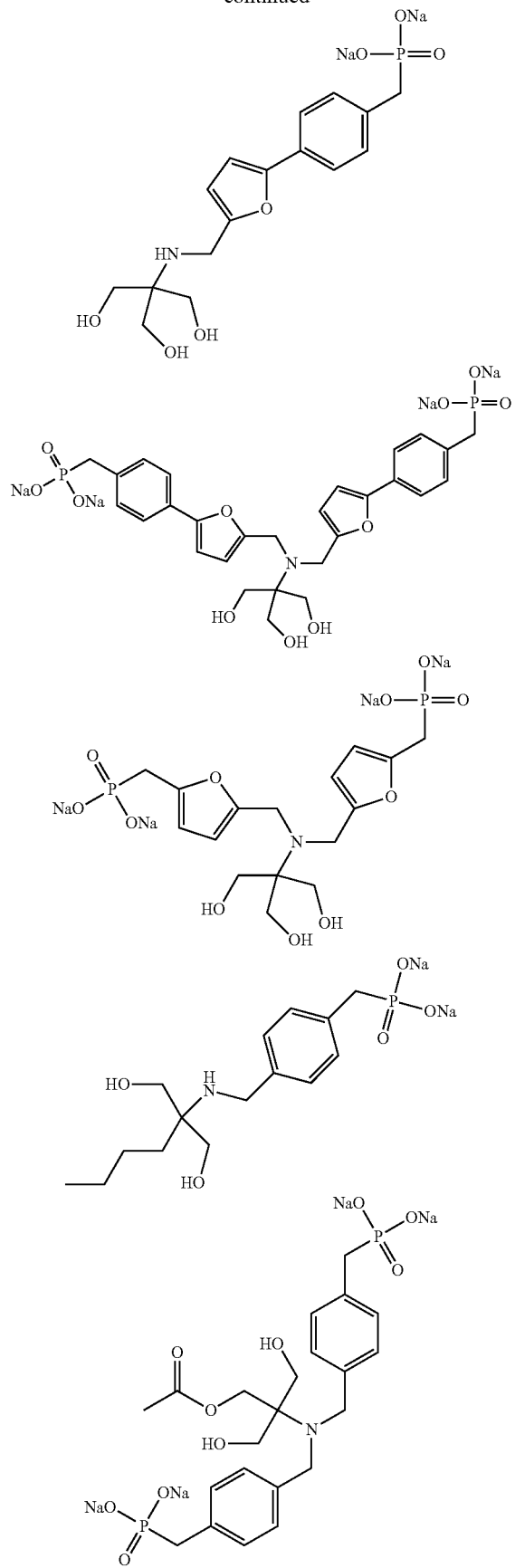
130
-continued
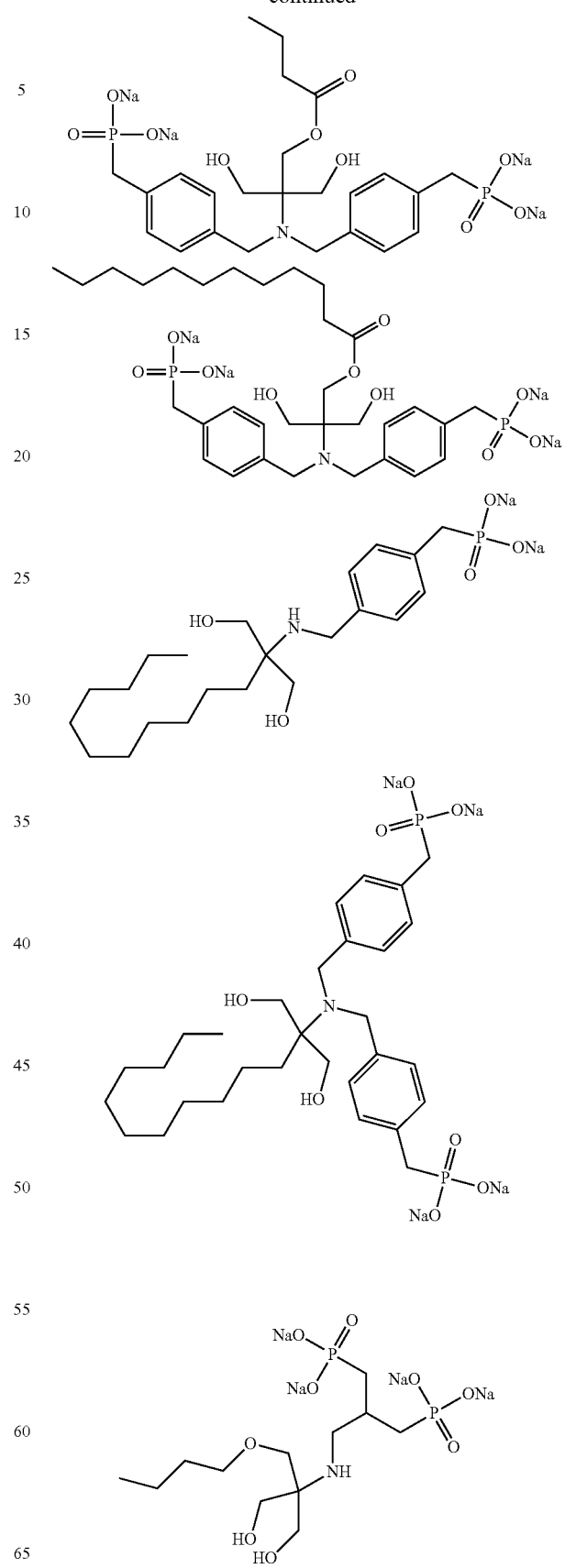

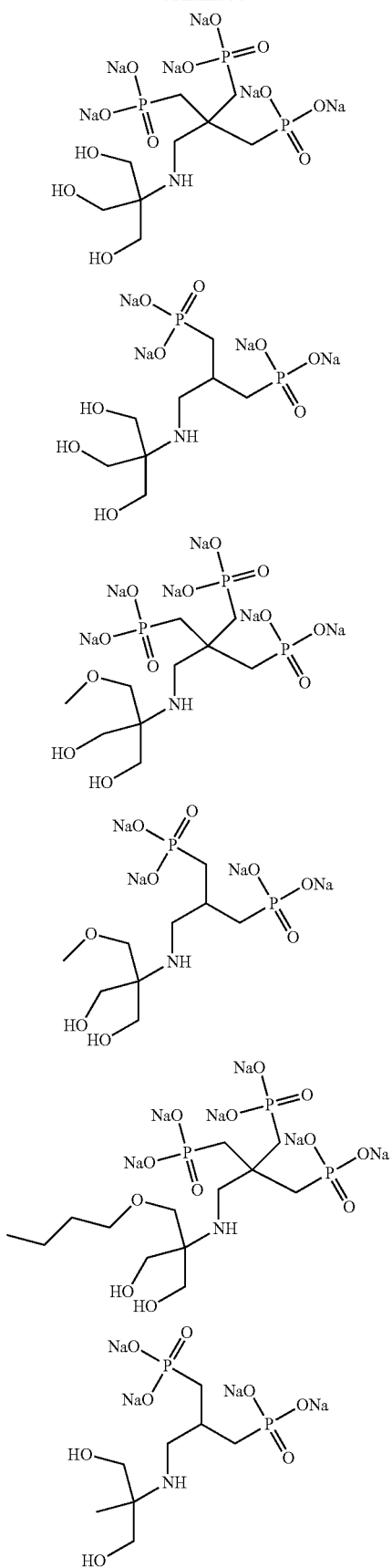
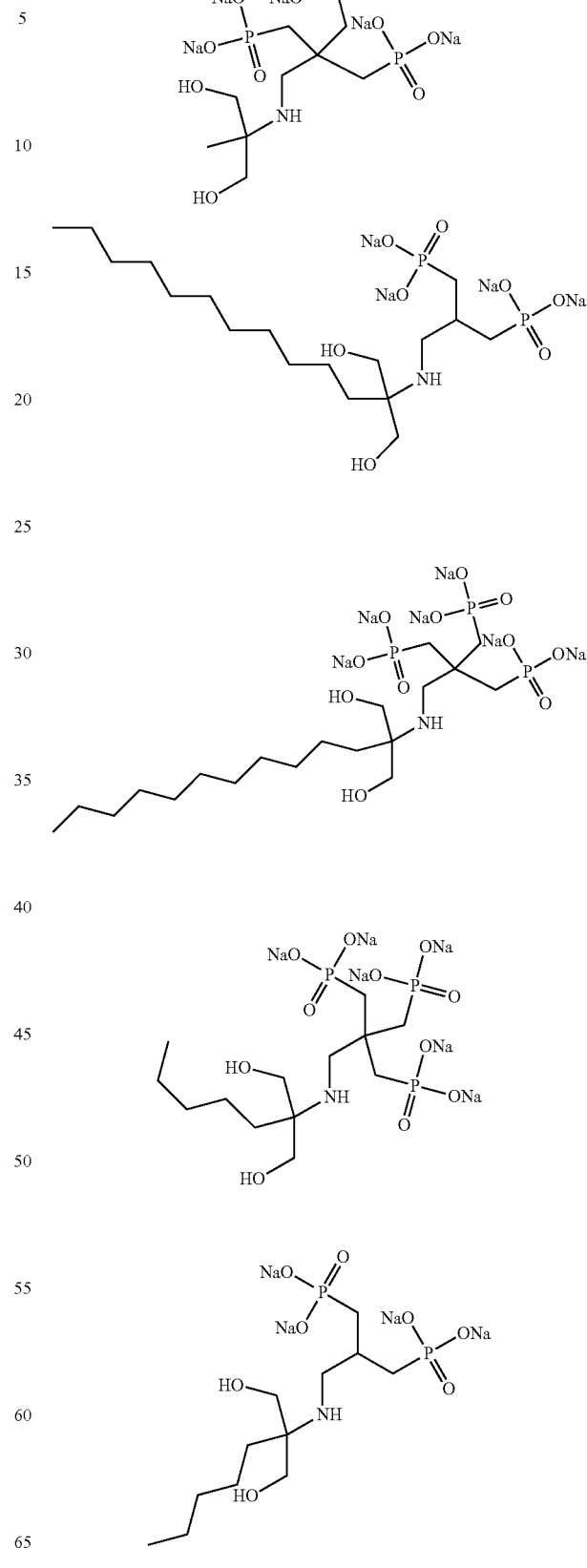

133
-continued
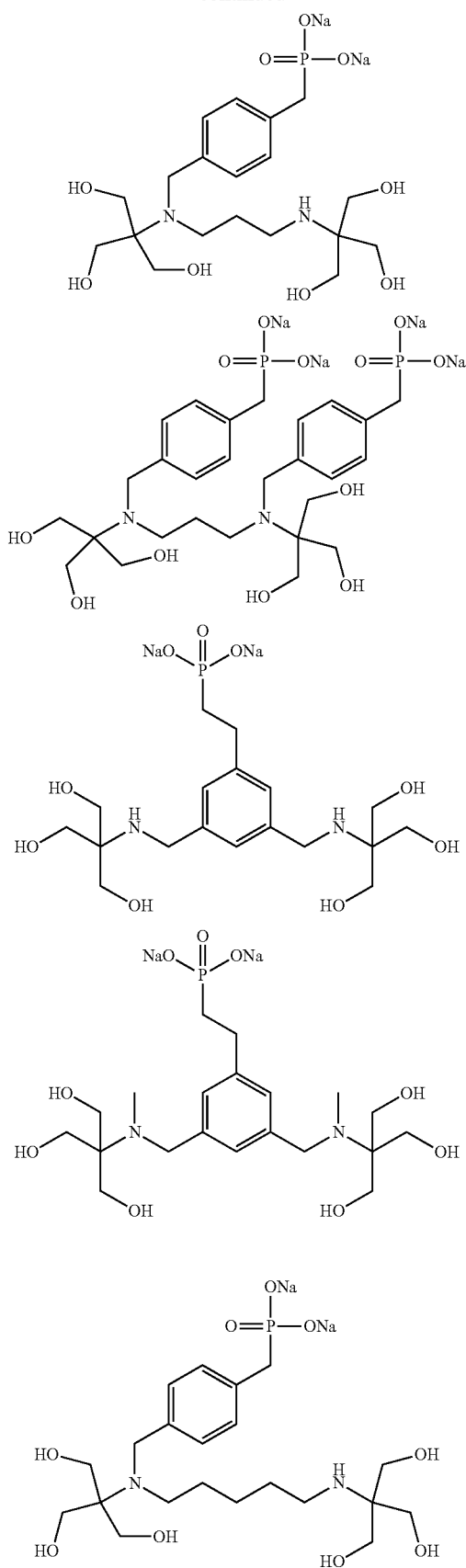
134
-continued
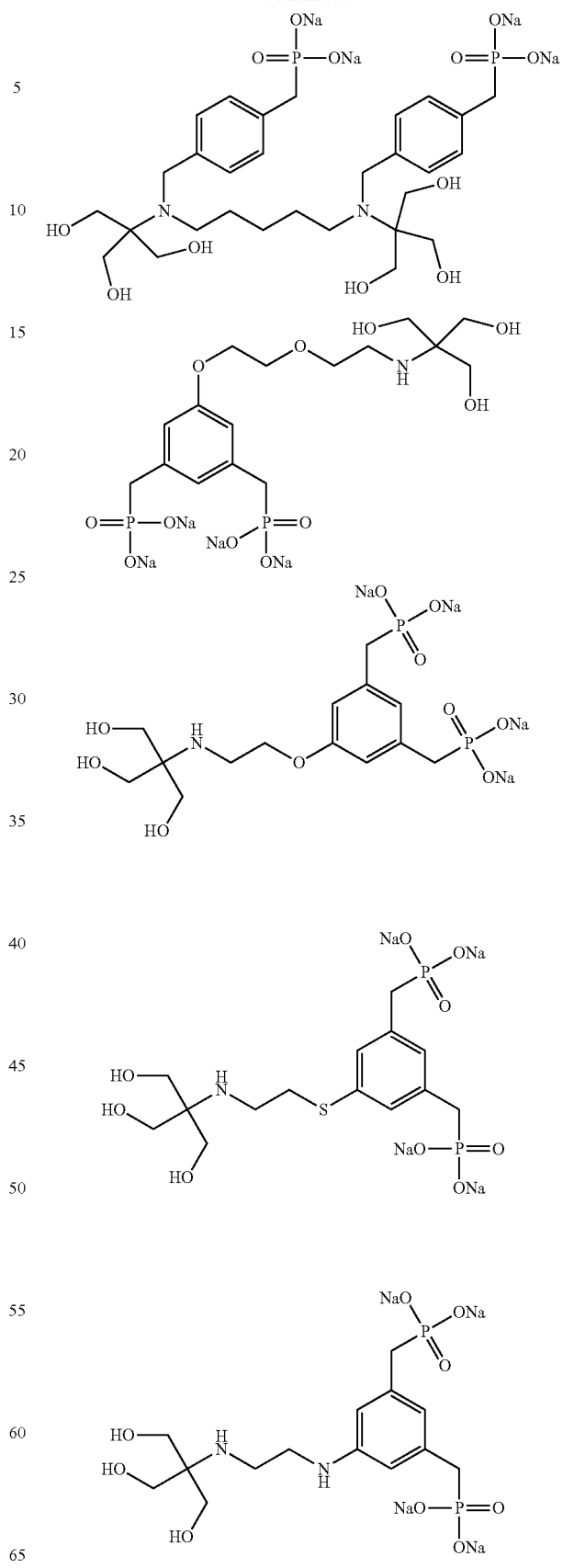

135
-continued
136
-continued
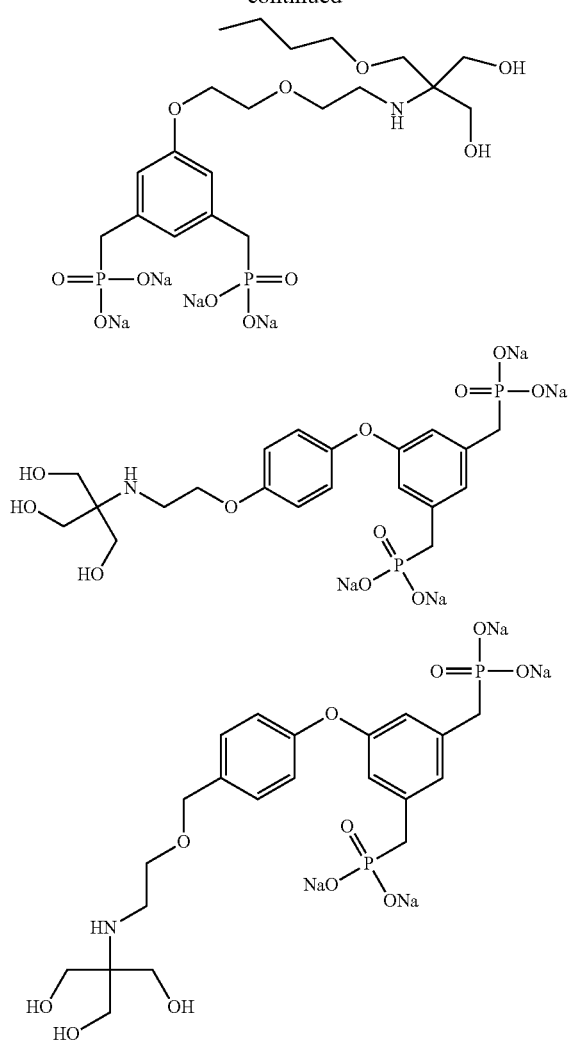
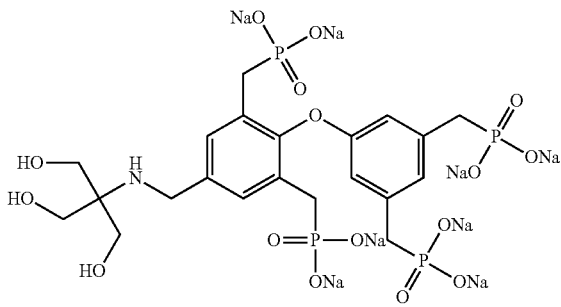

137
-continued
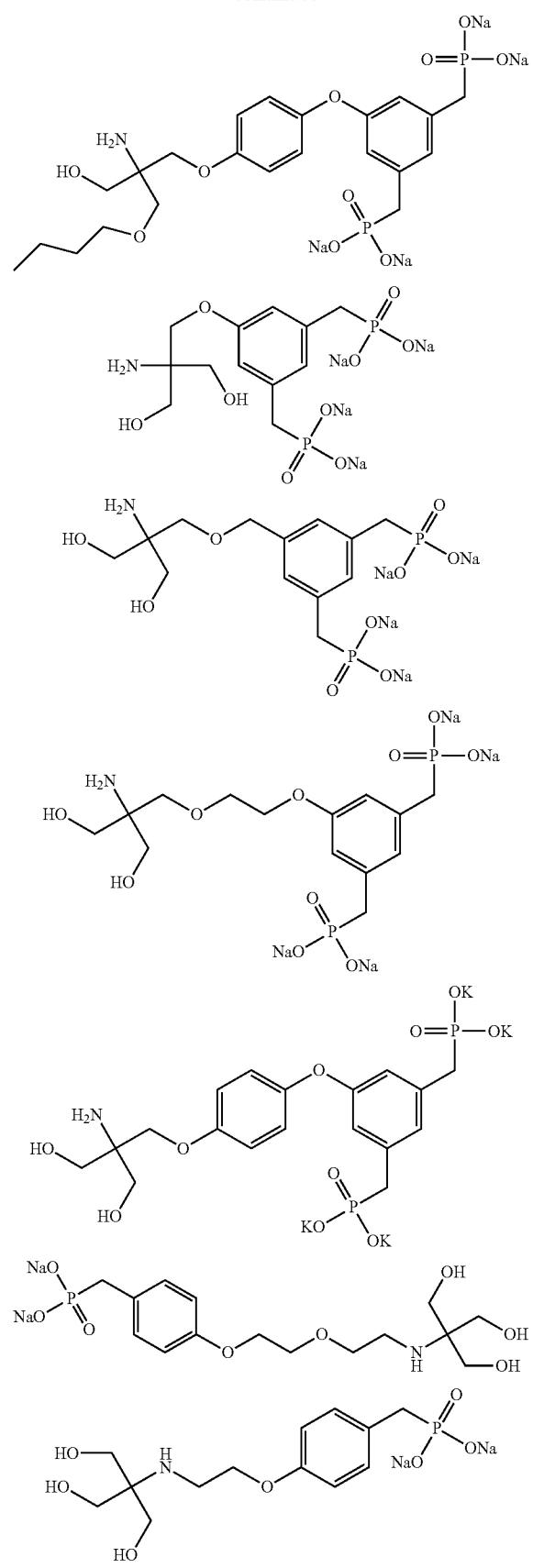
138
-continued
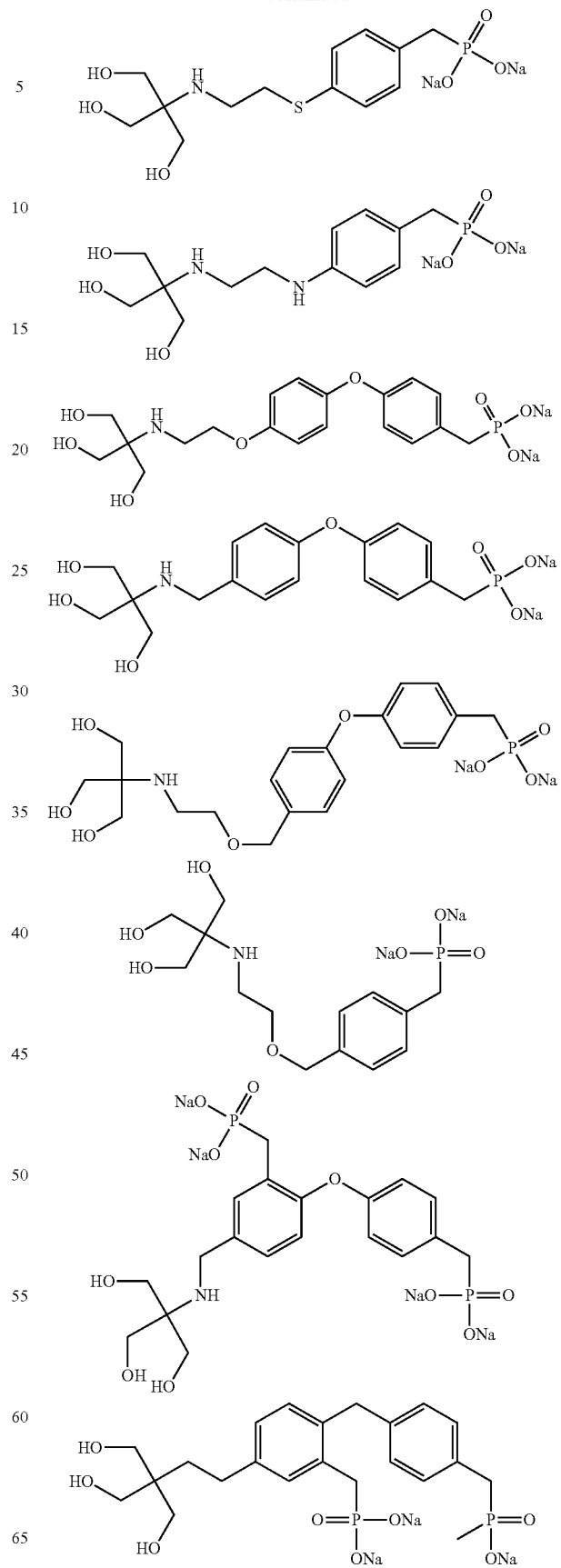

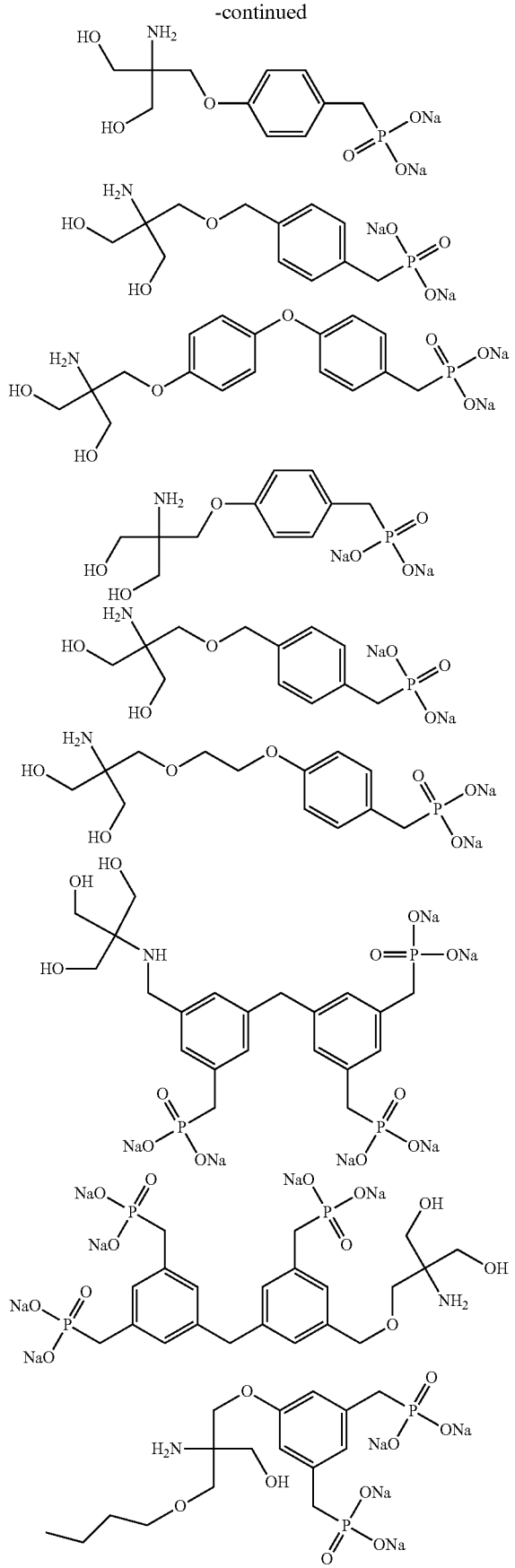
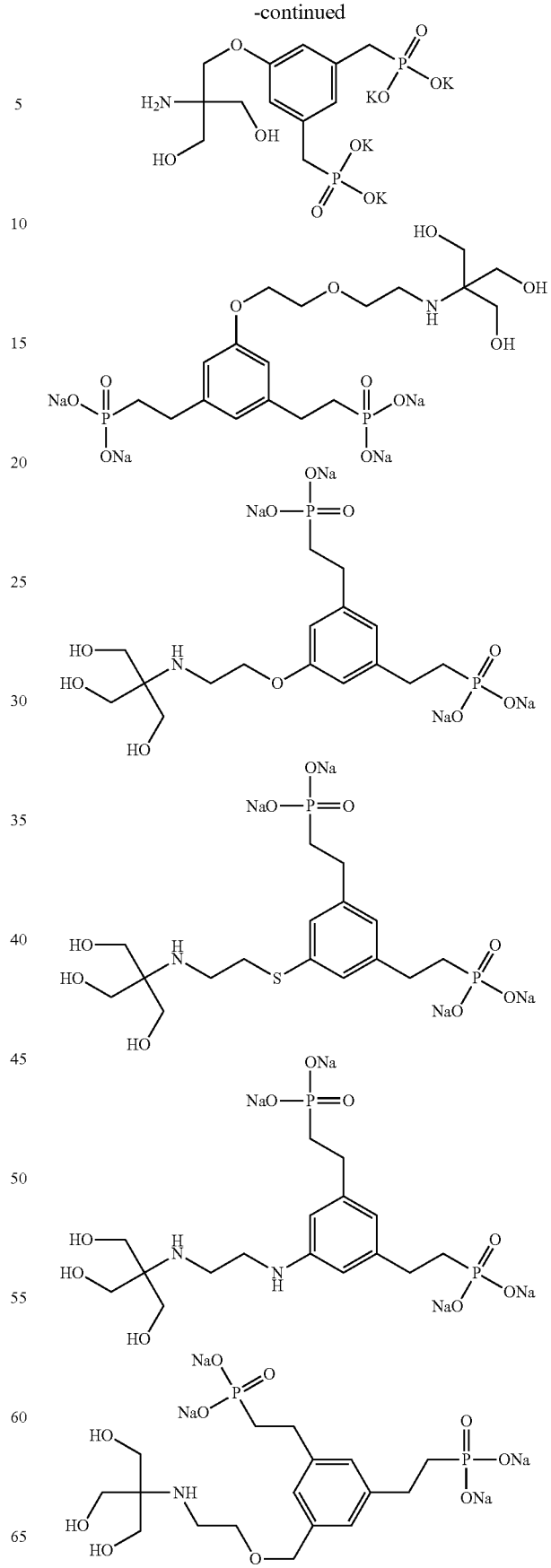

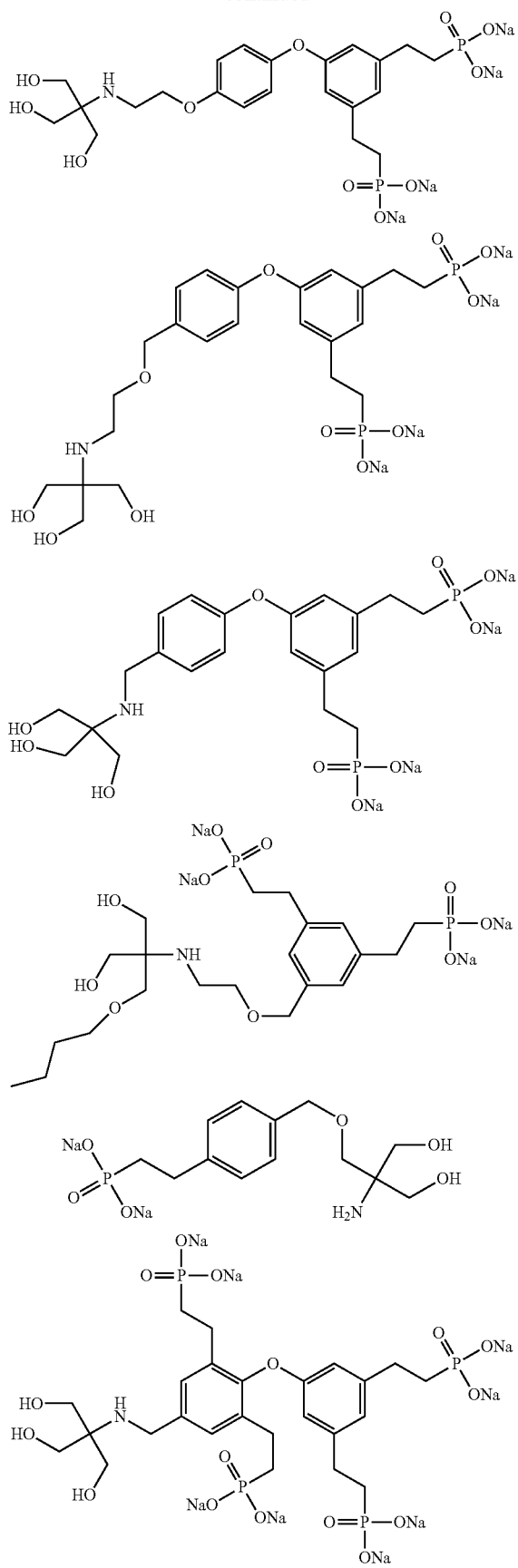
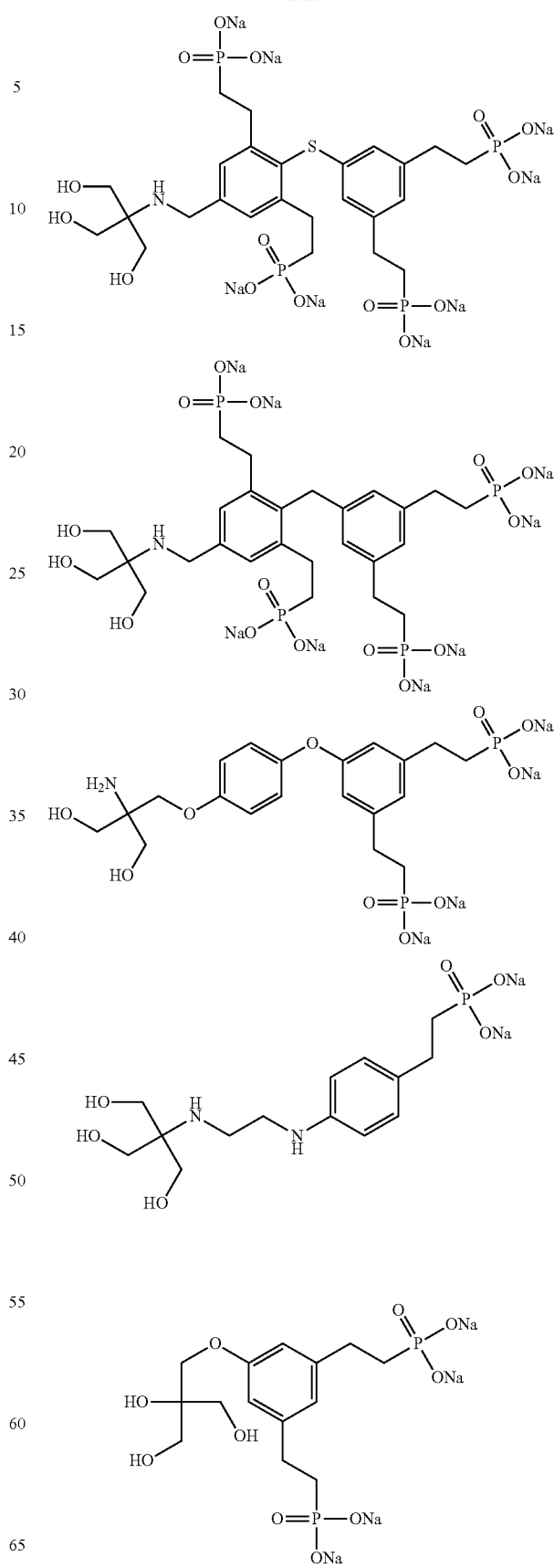

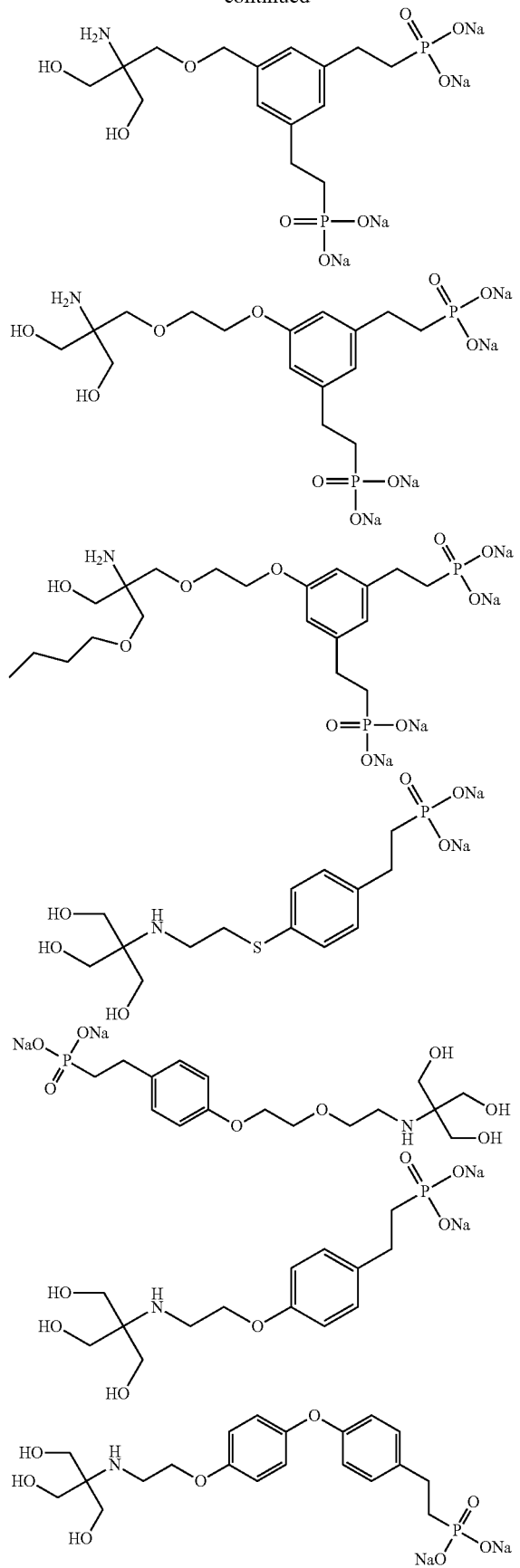
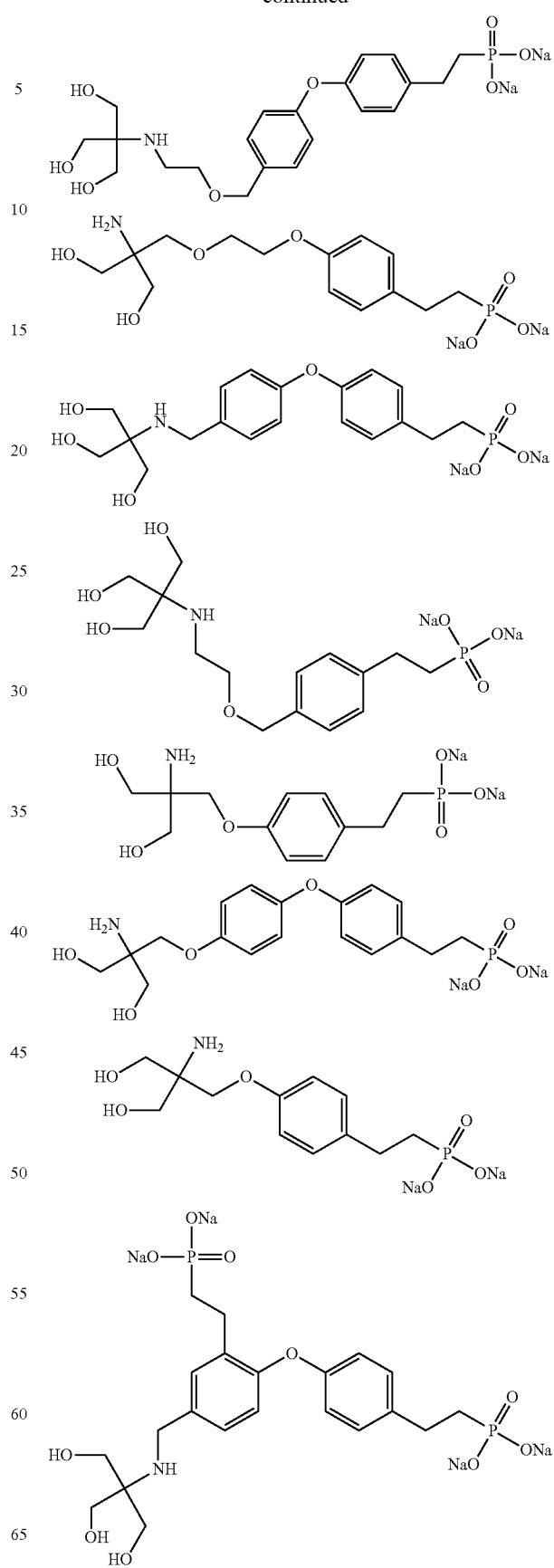

145
-continued
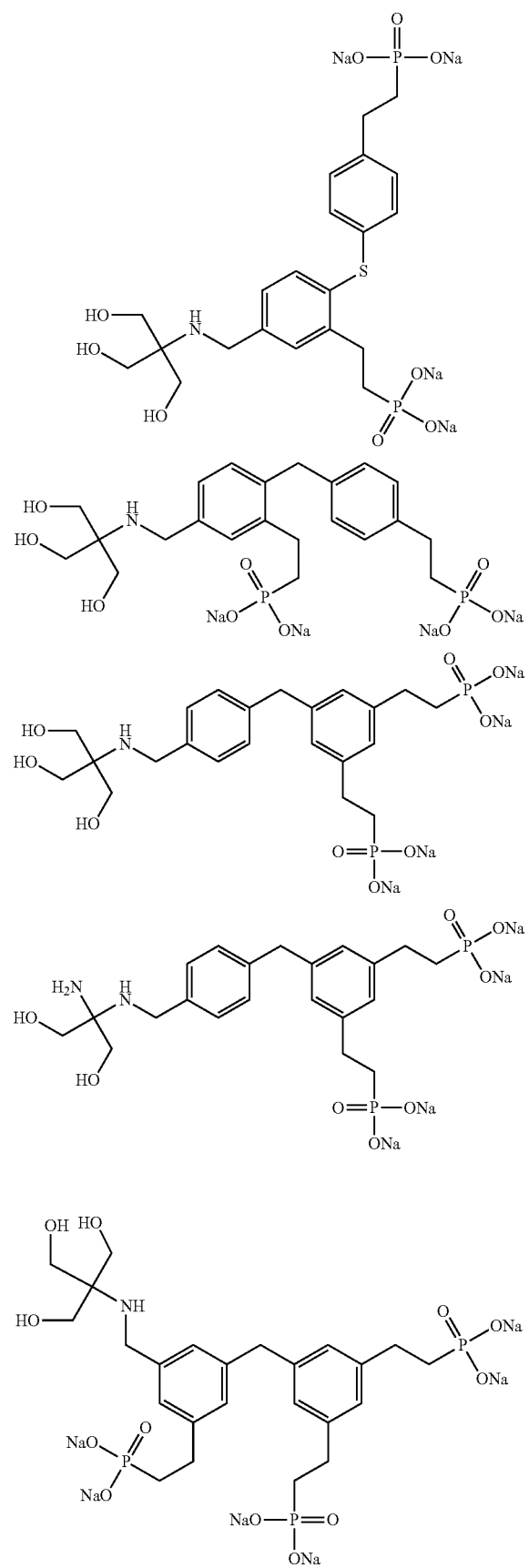
146
-continued
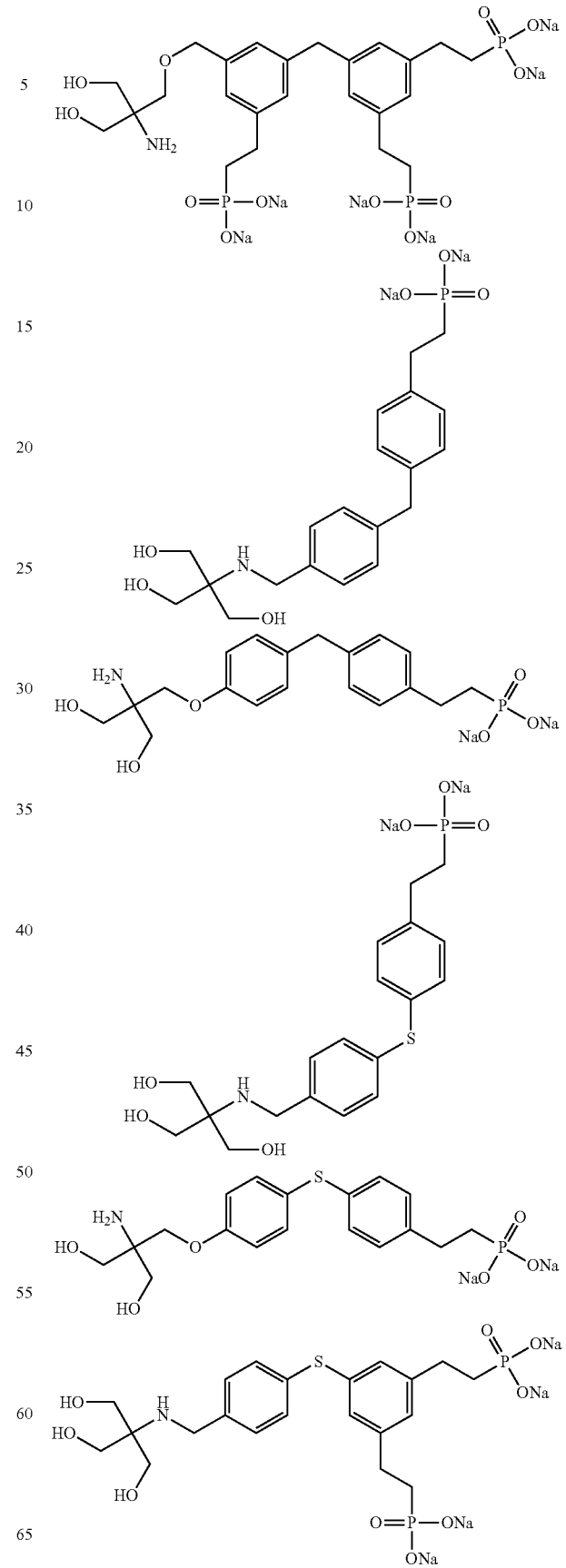

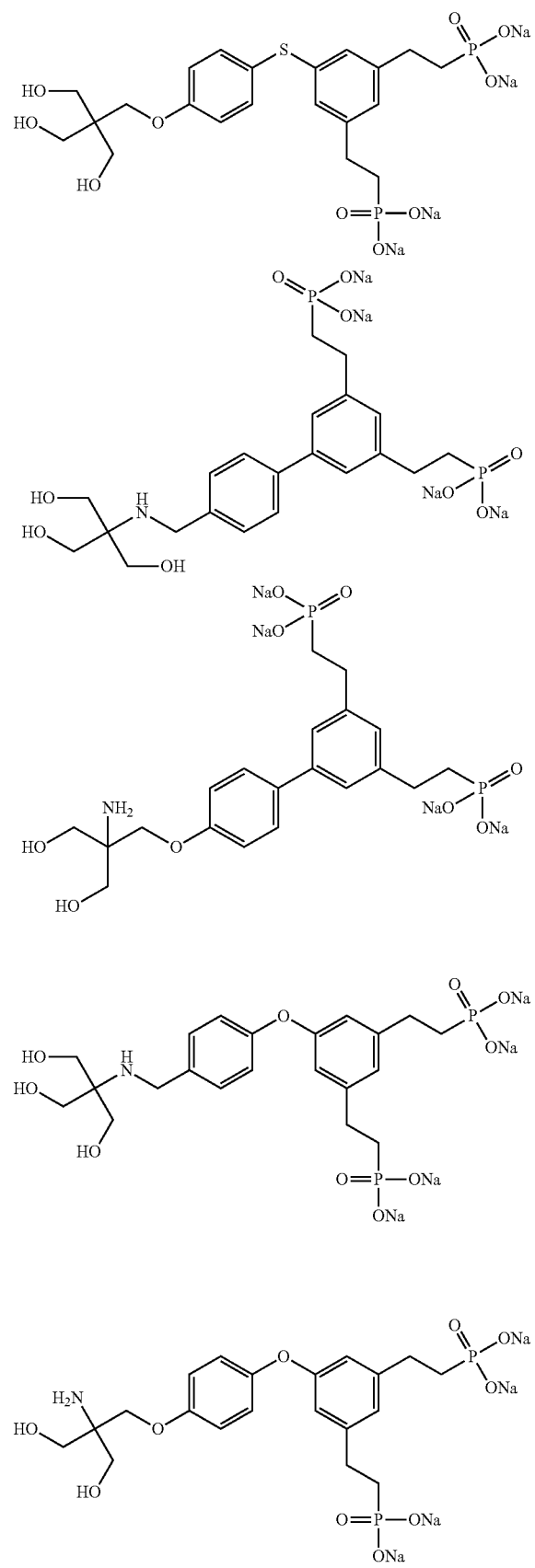
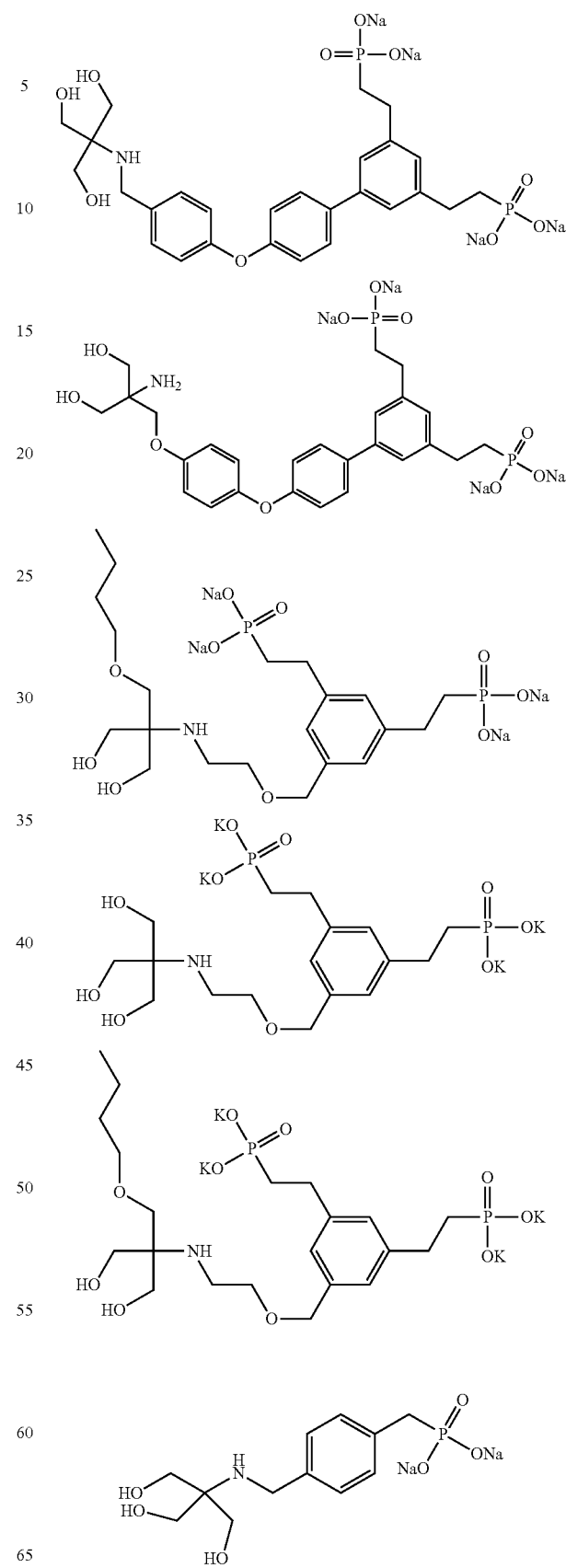

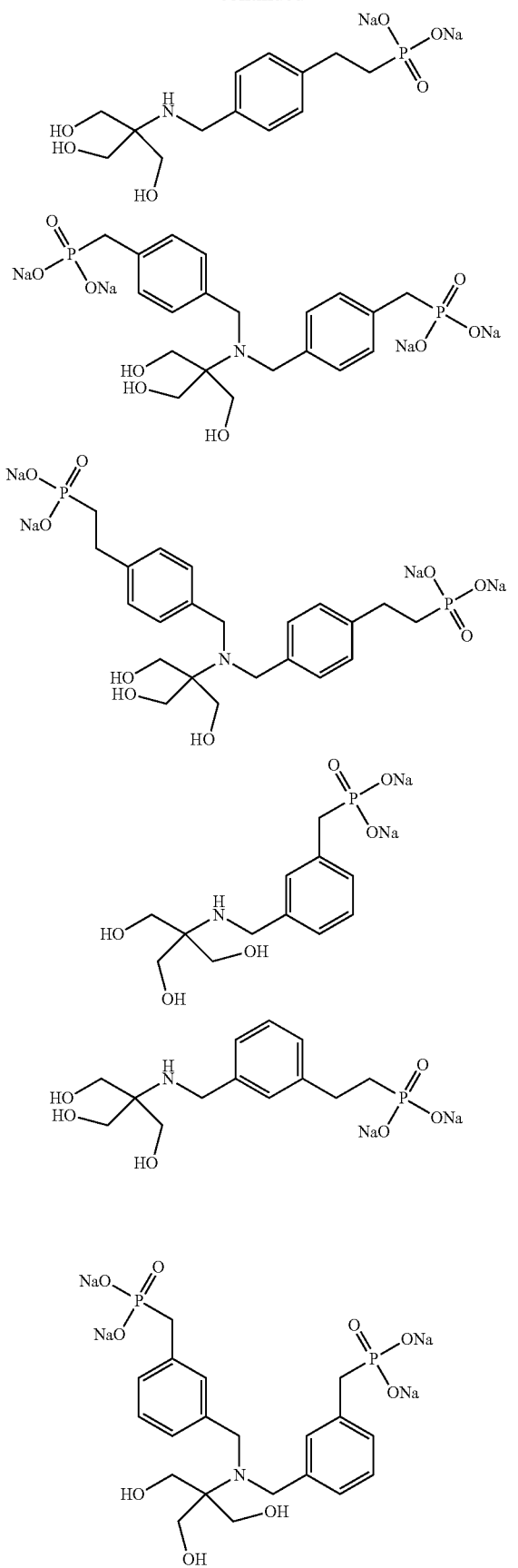
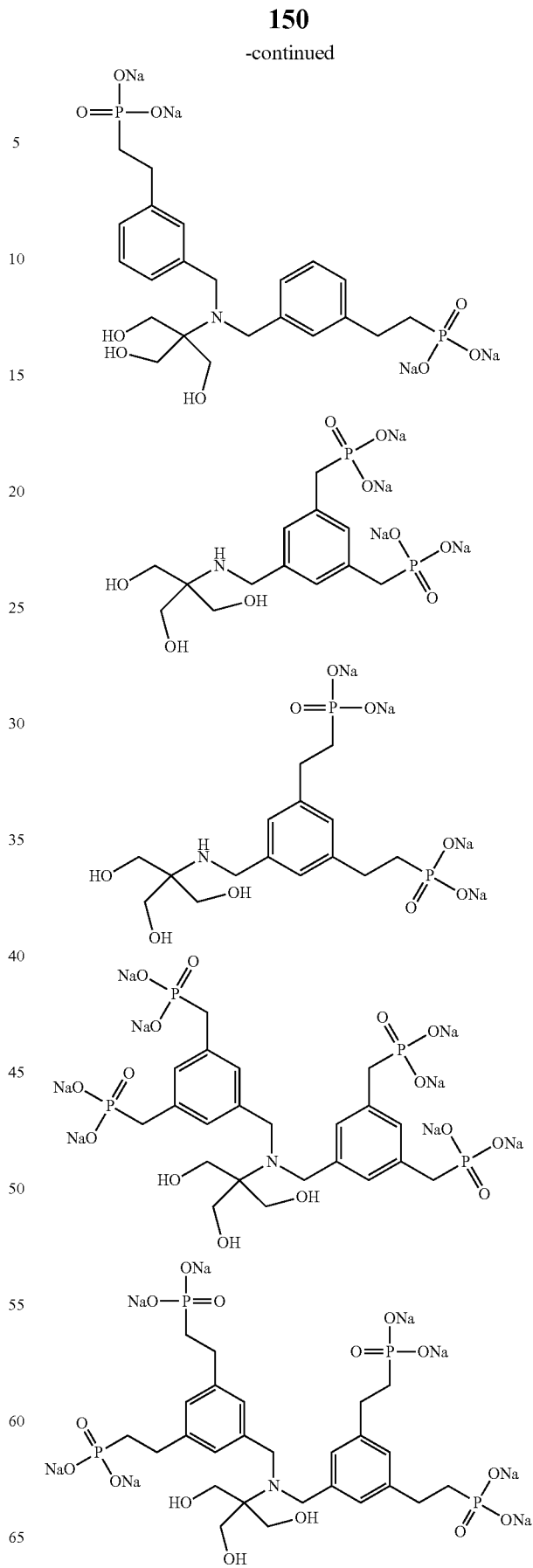

-continued
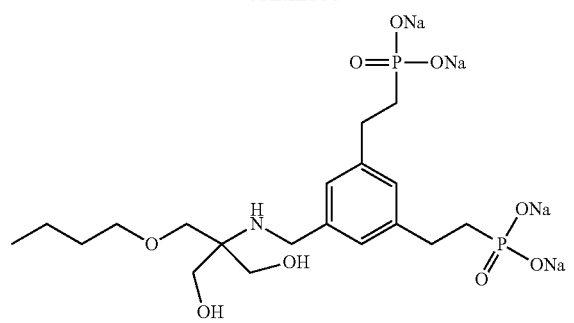
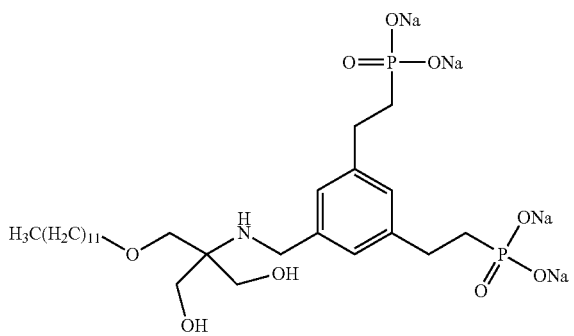
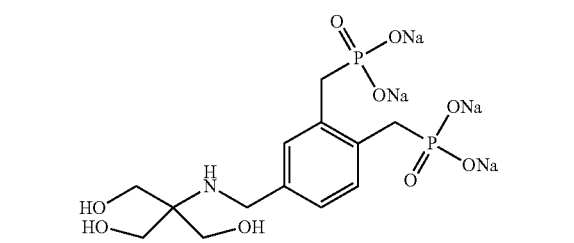
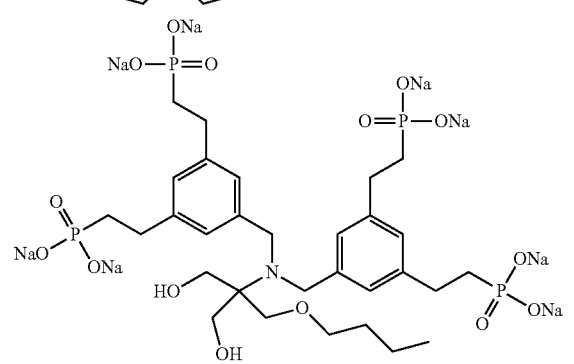
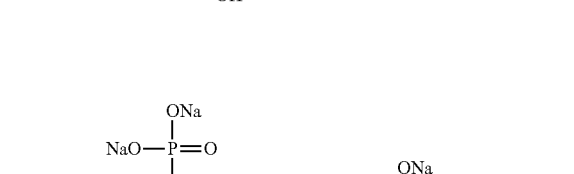
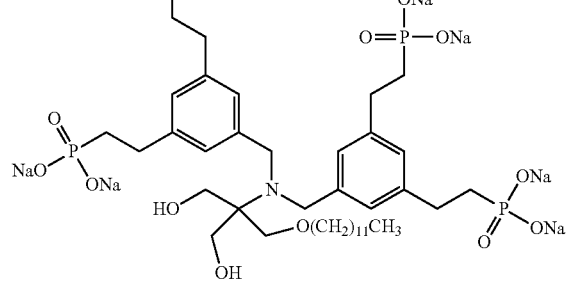
-continued
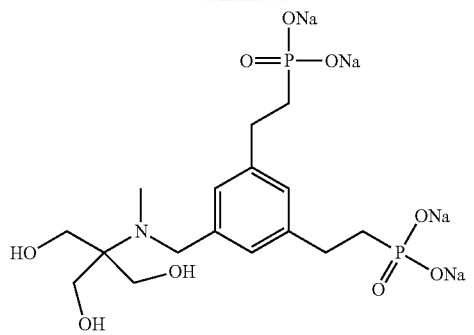
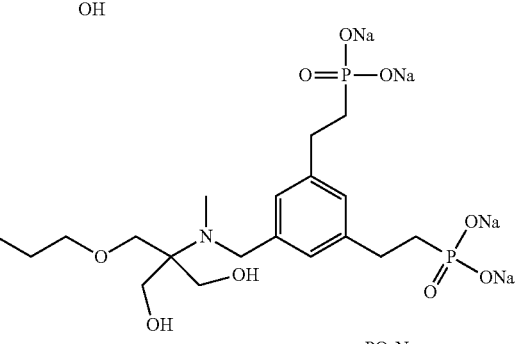
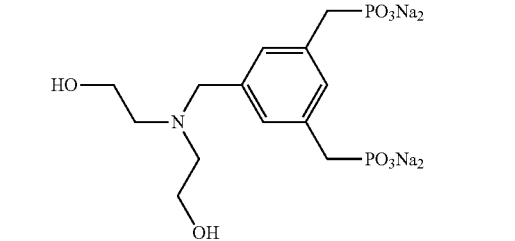
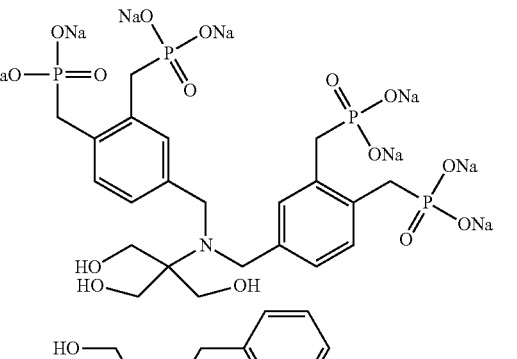
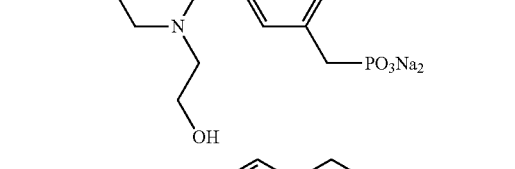
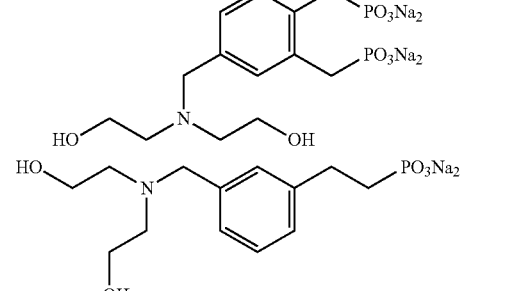

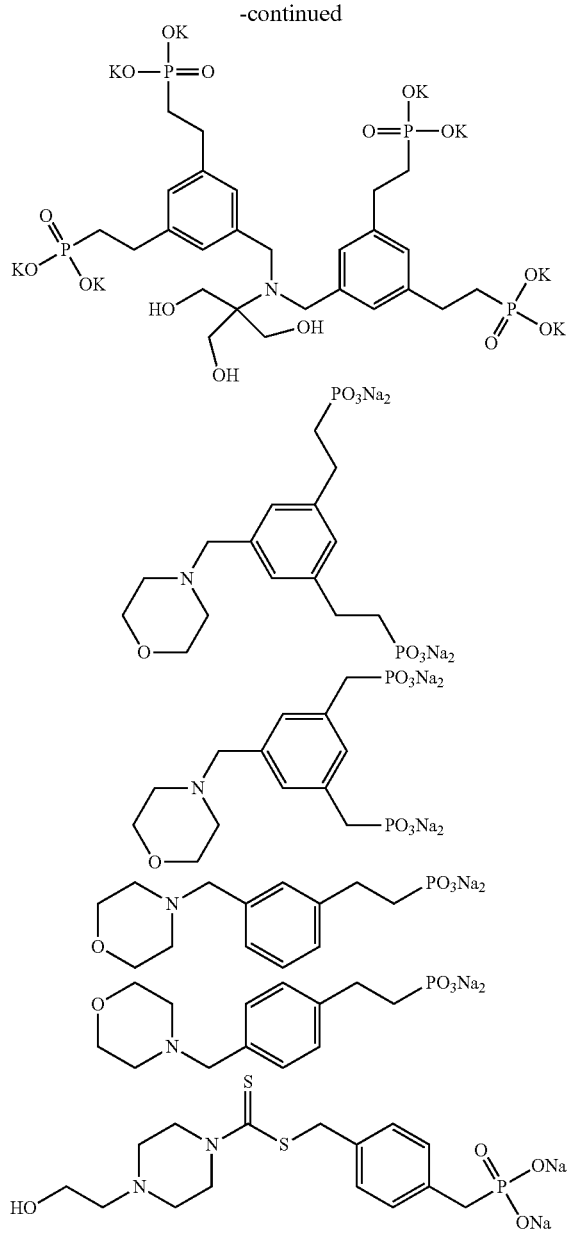

or the tautomer, mesomer, racemate, enantiomer, and diastereoisomer thereof, or the mixture form thereof, or the pharmaceutically acceptable salt thereof, or the prodrug molecule thereof.

6. A pharmaceutical composition, which comprises a therapeutically effective amount of the compound according to claim 1, or the tautomer, mesomer, racemate, enantiomer, and diastereoisomer thereof, or the mixture form thereof, or the pharmaceutically acceptable salt thereof, or the prodrug molecule thereof, and further comprises one or more pharmaceutically acceptable carriers, diluents, excipients.

7. A method of treating cancer in a subject in need thereof, comprising administering to the subject an effective amount of the compound according to claim 1, or the tautomer, mesomer, racemate, enantiomer, and diastereoisomer thereof, or the mixture form thereof, or the pharmaceutically acceptable salt thereof, or the prodrug molecule thereof, wherein the cancer is selected from the group consisting of liver cancer, prostate cancer, spleen cancer, intestine cancer, kidney cancer stomach cancer and pancreas cancer.

8. A method of inhibiting cancer metastasis in a subject in need thereof, comprising administering to the subject an effective amount of the compound according to claim 1, or the tautomer, mesomer, racemate, enantiomer, and diastereoisomer thereof, or the mixture form thereof, or the pharmaceutically acceptable salt thereof, or the prodrug molecule thereof, wherein the cancer is selected from the group consisting of liver cancer, spleen cancer, intestine cancer, kidney cancer stomach cancer and pancreas cancer.

9. A method of treating cancer and/or inhibiting cancer metastasis in a subject in need thereof, comprising administering to the subject an effective amount of the compound according to claim 1, or the tautomer, mesomer, racemate, enantiomer, and diastereoisomer thereof, or the mixture form thereof, or the pharmaceutically acceptable salt thereof, or the prodrug molecule thereof, in combination with at least one additional anticancer drug, wherein the cancer is selected from the group consisting of liver cancer, prostate cancer, spleen cancer, intestine cancer, kidney cancer stomach cancer and pancreas cancer.

10. A pharmaceutical composition, which comprises a therapeutically effective amount of the compound according to claim 5, or the tautomer, mesomer, racemate, enantiomer, and diastereoisomer thereof, or the mixture form thereof, or the pharmaceutically acceptable salt thereof, or the prodrug molecule thereof, and further comprises one or more pharmaceutically acceptable carriers, diluents, excipients.

11. A method of treating cancer in a subject in need thereof, comprising administering to the subject an effective amount of the compound according to claim 5, or the tautomer, mesomer, racemate, enantiomer, and diastereoisomer thereof, or the mixture form thereof, or the pharmaceutically acceptable salt thereof, or the prodrug molecule thereof, wherein the cancer is selected from the group consisting of liver cancer, prostate cancer, spleen cancer, intestine cancer, kidney cancer stomach cancer and pancreas cancer.

12. A method of inhibiting cancer metastasis in a subject in need thereof comprising administering to the subject an effective amount of the compound according to claim 5, or the tautomer, mesomer, racemate, enantiomer, and diastereoisomer thereof, or the mixture form thereof, or the pharmaceutically acceptable salt thereof, or the prodrug molecule thereof, wherein the cancer is selected from the group consisting of liver cancer, spleen cancer, intestine cancer, kidney cancer stomach cancer and pancreas cancer.

13. A method of treating cancer and/or inhibiting cancer metastasis in a subject in need thereof, comprising administering to the subject an effective amount of the compound according to claim 5, or the tautomer, mesomer, racemate, enantiomer, and diastereoisomer thereof, or the mixture form thereof, or the pharmaceutically acceptable salt thereof, or the prodrug molecule thereof, in combination with at least one additional anticancer drug, wherein the cancer is selected from the group consisting of liver cancer, prostate cancer, spleen cancer, intestine cancer, kidney cancer stomach cancer and pancreas cancer.

\* \* \* \* \*